(12) United States Patent
Fujii

(10) Patent No.: US 10,514,602 B2
(45) Date of Patent: Dec. 24, 2019

(54) RESIST COMPOSITION AND METHOD FOR FORMING RESIST PATTERN

(71) Applicant: TOKYO OHKA KOGYO CO., LTD., Kawasaki-shi, Kanagawa-ken (JP)

(72) Inventor: Tatsuya Fujii, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 15/663,299

(22) Filed: Jul. 28, 2017

(65) Prior Publication Data

US 2018/0037534 A1 Feb. 8, 2018

(30) Foreign Application Priority Data

Aug. 3, 2016 (JP) ................. 2016-152997

(51) Int. Cl.
| | |
|---|---|
| *G03F 7/004* | (2006.01) |
| *G03F 7/039* | (2006.01) |
| *G03F 7/20* | (2006.01) |
| *C07C 67/14* | (2006.01) |
| *C07C 69/54* | (2006.01) |
| *C07D 307/93* | (2006.01) |
| *C07D 309/12* | (2006.01) |
| *C08F 12/24* | (2006.01) |
| *C08F 20/16* | (2006.01) |
| *C08F 244/00* | (2006.01) |

(52) U.S. Cl.
CPC ............ *G03F 7/0397* (2013.01); *C07C 67/14* (2013.01); *C07C 69/54* (2013.01); *C07D 307/93* (2013.01); *C07D 309/12* (2013.01); *C08F 12/24* (2013.01); *C08F 20/16* (2013.01); *C08F 244/00* (2013.01); *G03F 7/0045* (2013.01); *G03F 7/2004* (2013.01); *G03F 7/2006* (2013.01); *G03F 7/2041* (2013.01); *G03F 7/2059* (2013.01)

(58) Field of Classification Search
CPC .... G03F 7/0397; G03F 7/2004; G03F 7/2006; G03F 7/2041; G03F 7/2059; C08F 222/10; C08F 214/18; C08F 224/00; C08F 228/00

USPC .............. 430/270.1, 905, 907, 910; 562/281, 562/292.4, 313
See application file for complete search history.

(56) References Cited

U.S. PATENT DOCUMENTS

| 8,900,795 B2 * | 12/2014 | Utsumi | ................... G03F 7/004 430/270.1 |
| 8,986,919 B2 * | 3/2015 | Takaki | .................. C08F 220/22 430/281.1 |
| 2012/0258402 A1 | 10/2012 | Sato et al. | |

FOREIGN PATENT DOCUMENTS

| JP | A-2009-114381 | 5/2009 |
| JP | A-2012-220800 | 11/2012 |
| WO | WO 2010/095698 A1 | 8/2010 |
| WO | WO 2013/042694 A1 | 3/2013 |

\* cited by examiner

*Primary Examiner* — John S Chu
(74) *Attorney, Agent, or Firm* — Knobbe, Martens, Olson & Bear LLP

(57) ABSTRACT

A resist composition includes a base material component and a fluorine additive component. The fluorine additive component contains a fluororesin component having a structural unit containing a base dissociable group. The base material component contains a structural unit containing an acid-decomposable group in an amount of 30 mol % or more and an amount of 10 mol % or more of a resin component having a structural unit represented by formula (a10-1):

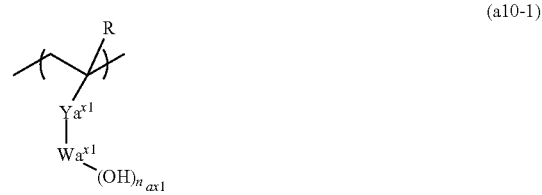

(a10-1)

where R is a hydrogen atom, an alkyl group having 1 to 5 carbon atoms, or a halogenated alkyl group having 1 to 5 carbon atoms, $Y_a^{x1}$ is a single bond or a divalent linking group, $W_a^{x1}$ is a ($n_{ax1}$+1) valent aromatic hydrocarbon group, and $na_{x1}$ is an integer of 1 to 3.

6 Claims, No Drawings

RESIST COMPOSITION AND METHOD FOR FORMING RESIST PATTERN

CROSS-REFERENCE TO RELATED APPLICATIONS

Priority is claimed on Japanese Patent Application No. 2016-152997, filed Aug. 3, 2016, the content of which is incorporated herein by reference.

BACKGROUND OF THE INVENTION

Field of the Invention

The present invention relates to a resist composition and a method for forming a resist pattern.

Background Art

A lithography technique includes steps of forming a resist film formed of a resist material on a substrate, selectively exposing the resist film, and performing a developing treatment, thereby forming a resist pattern having a predetermined shape. A resist material in which an exposed area of the resist film is dissolved in a developing solution is referred to as a positive-type resist material, and a resist material in which an exposed area of the resist film is not dissolved in a developing solution is referred to as a negative-type resist material.

In recent years, in the manufacturing of semiconductor devices and liquid crystal display elements, pattern miniaturization has been rapidly progressed in accordance with the progress of the lithography technique. As a miniaturization technique, generally, shortening the wavelength (realizing high energy) of an exposure light source has been performed. Specifically, ultraviolet rays represented by a g-line and an i-line was used in the related art, but KrF excimer laser or ArF excimer laser has been used for the mass production of semiconductor devices these days. In addition, studies regarding extreme ultraviolet rays (EUV) having a short wavelength (high energy) than an excimer laser, electron beams (EB), and an X-ray have been conducted.

Further, in recent years, in EUV lithography or EB lithography, a chemically amplified resist composition which has been proposed as a resist resin for KrF excimer laser or ArF excimer laser has been generally used as a resist material from the viewpoint of excellent lithography properties such as sensitivity with respect to EUV and EB, and resolution capable of forming minute resist pattern set as a target. Particularly, the chemically amplified resist composition containing an acrylic-based resin as a base resin is excellent in the lithography properties.

Particularly, in the EUV exposure, acid diffusion controllability was a problem in the resist material. In order to control the acid diffusion, changing an anion structure of an acid generator is generally used, and an acid generator having an anion structure with a short diffusion length is already employed.

In order to further control the acid diffusion, a method for variously changing the design of a polymer compound has been employed.

For example, Pamphlet of International Publication No. 2013/042694, Japanese Unexamined Patent Application, Publication No. 2009-114381, Japanese Unexamined Patent Application, Publication No. 2012-220800, and Pamphlet of International Publication No. 2010/095698 disclose a resist composition in which a polymer compound containing a specific acid dissociable functional group is applied to thereby improve the reactivity to an acid and contribute to improving the solubility in a developing solution.

SUMMARY OF THE INVENTION

Meanwhile, as the lithography technique further progresses and the miniaturization of the resist pattern progresses more and more, for example, a target of the lithography performed by an electron beam or EUV is to form fine resist patterns of several tens of nanometers.

As the miniaturization of the pattern progresses, the resist material is required to improve various lithography properties, and to suppress the occurrence of defects (surface defects).

Here, "defect" means, for example, general problems that are detected when the developed resist pattern is directly viewed from the above by using a surface defect observing apparatus (product name of "KLA") manufactured by KLA-Tencor Corporation. Examples of the defects include a defect relating to foreign matters and precipitates attached on the resist pattern surface such as scum after development (resist residue), bubbles, and dust; a defect relating to a pattern shape such as bridge between line patterns and filling of a hole having a contact hole pattern; and a defect of a color unevenness of the pattern.

The present invention has been made in consideration of the above circumstance, and an object thereof is to provide a resist composition in which the lithography properties are improved and generation of the defects is reduced.

According to a first aspect of the present invention, there is provided a resist composition which generates an acid upon exposure, and whose solubility in a developing solution changes under the action of an acid, the resist composition containing a base material component (A) whose solubility in the developing solution changes under the action of an acid, and a fluorine additive component (F) which exhibits the decomposability with respect to an alkali developing solution, in which the base material component (A) contains a resin component (A1) having a structural unit (a10) represented by general formula (a10-1) which is 10 mol % or more, and a structural unit (a1) which contains an acid-decomposable group having polarity increased under the action of the acid, and is 30 mol % or more, and the fluorine additive component (F) contains a fluororesin component (F1) having a structural unit (f1) containing a base dissociable group.

(a10-1)

In the formula, R is a hydrogen atom, an alkyl group having 1 to 5 carbon atoms, or a halogenated alkyl group having 1 to 5 carbon atoms. $Ya^{x1}$ is a single bond or a divalent linking group. $Wa^{x1}$ is a $(n_{ax1}+1)$ valent aromatic hydrocarbon group which may have a substituent. $na_{x1}$ is an integer of 1 to 3.

According to a second aspect of the present invention, there is provided a method for forming a resist pattern, including a step of forming a resist film on a support by using a resist composition according to the first aspect, a step of exposing the resist film, and a step of developing the exposed resist film to form a resist pattern.

According to the present invention, it is possible to provide a resist composition in which the lithography properties are improved and defects are reduced, and a method for forming a resist pattern using the same.

DETAILED DESCRIPTION OF THE INVENTION

In the specification and claims of the present application, "aliphatic" is a relative concept with respect to aromatics, and is defined as a group, a compound, or the like having no aromaticity.

"Alkyl group" is assumed to contain a linear, branched, or cyclic monovalent saturated hydrocarbon group unless otherwise noted. The same is true for an alkyl group in an alkoxy group.

"Alkylene group" is assumed to contain a linear, branched, and cyclic divalent saturated hydrocarbon group unless otherwise noted.

"Halogenated alkyl group" is a group obtained by substituting at least one hydrogen atom of an alkyl group with a halogen atom, and examples of the halogen atom include a fluorine atom, a chlorine atom, a bromine atom, and an iodine atom.

"Fluorinated alkyl group" or "fluorinated alkylene group" means a group obtained by substituting at least one hydrogen atom of an alkyl group or an alkylene group with a fluorine atom.

"Structural unit" means a monomer unit constituting a polymer compound (a resin, a polymer, or a copolymer).

The phrase "may have a substituent" means both the case of substituting a hydrogen atom (—H) with a monovalent group and the case of substituting a methylene group (—$CH_2$—) with a divalent group.

"Exposure" is a concept including radiation irradiation in general.

"Structural unit derived from acrylic ester" means a structural unit formed by cleavage of an ethylenic double bond of the acrylic ester.

"Acrylic ester" is a compound obtained by substituting a hydrogen atom at a carboxy group terminal of an acrylic acid ($CH_2$=CH—COOH) with an organic group.

The acrylic ester may be obtained by substituting a hydrogen atom bonded to an α-position carbon atom with a substituent. The substituent ($R^{\alpha 0}$) with which the hydrogen atom bonded to the α-position carbon atom is substituted is an atom other than the hydrogen atom or a group, and examples thereof include an alkyl group having 1 to 5 carbon atoms and a halogenated alkyl group having 1 to 5 carbon atoms. In addition, it is assumed that the acrylic ester includes itaconic acid diester obtained by substituting the substituent ($R^{\alpha 0}$) with a substituent containing an ester bond, and α-hydroxyacrylic ester obtained by substituting the substituent ($R^{\alpha 0}$) with a group modified with a hydroxyalkyl group or a hydroxyl group thereof. Note that, the α-position carbon atom of the acrylic ester is a carbon atom to which a carbonyl group of an acrylic acid is bonded unless otherwise noted.

Hereinafter, acrylic ester obtained by substituting the hydrogen atom bonded to an α-position carbon atom with a substituent may be referred to as α-substituted acrylic ester.

In addition, both of the acrylic ester and the α-substituted acrylic ester may be referred to as "(α-substituted) acrylic ester".

"Structural unit derived from acrylamide" means a structural unit formed by cleavage of an ethylenic double bond of the acrylamide.

The acrylamide may be obtained by substituting a hydrogen atom bonded to an α-position carbon atom with a substituent or may be obtained by substituting one or both of hydrogen atoms of an amino group of acrylamide with a substituent. Note that, the α-position carbon atom of the acrylamide is a carbon atom to which a carbonyl group of acrylamide is bonded unless otherwise noted.

As the substituent with which a hydrogen atom bonded to the α-position carbon atom of the acrylamide is substituted, the same substituent as that (substituent))($R^{\alpha 0}$) exemplified as an α-position substituent in the α-substituted acrylic ester can be used.

"Structural unit derived from hydroxystyrene" means a structural unit formed by cleavage of an ethylenic double bond of hydroxystyrene. "Structural unit derived from a hydroxystyrene derivative" means a structural unit formed by cleavage of an ethylenic double bond of a hydroxystyrene derivative.

"Hydroxystyrene derivative" includes those obtained by substituting an α-position hydrogen atom of hydroxystyrene with other substituents such as an alkyl group and a halogenated alkyl group, and derivatives thereof. Examples of the derivatives include a derivative obtained by substituting a hydrogen atom of a hydroxyl group of hydroxystyrene in which the α-position hydrogen atom may be substituted with a substituent with an organic group; and a derivative in which a substituent other than the hydroxyl group is bonded to a benzene ring of hydroxystyrene in which α-position hydrogen atom may be substituted with a substituent. Here, the α-position (α-position carbon atom) means a carbon atom to which a benzene ring is bonded unless otherwise noted.

As the substituent with which the α-position hydrogen atom of the hydroxystyrene is substituted, the same substituent as that exemplified as an α-position substituent in the α-substituted acrylic ester can be used.

"Structural unit derived from a vinylbenzoic acid or a vinylbenzoic acid derivative" means a structural unit formed by cleavage of an ethylenic double bond of a vinylbenzoic acid or a vinylbenzoic acid derivative.

"Vinylbenzoic acid derivative" includes those obtained by substituting an α-position hydrogen atom of a vinylbenzoic acid with other substituents such as an alkyl group and a halogenated alkyl group, and derivatives thereof. Examples of the derivatives include a derivative obtained by substituting a hydrogen atom of a carboxy group of the vinylbenzoic acid in which the α-position hydrogen atom may be substituted with a substituent with an organic group; and a derivative in which a substituent other than the hydroxyl group and the carboxy group is bonded to a benzene ring of the vinylbenzoic acid in which α-position hydrogen atom may be substituted with a substituent. Here, the α-position (α-position carbon atom) means a carbon atom to which a benzene ring is bonded unless otherwise noted.

"Styrene" is a concept including styrene and those obtained by substituting an α-position hydrogen atom of the styrene with other substituents such as an alkyl group and a halogenated alkyl group.

"Styrene derivative" is a concept including those obtained by substituting the α-position hydrogen atom of the styrene with other substituents such as an alkyl group and a halogenated alkyl group, and the derivatives thereof. Examples of the derivatives include a derivative in which a substituent is bonded to a benzene ring of hydroxystyrene in which the α-position hydrogen atom may be substituted with a substituent. Here, the α-position (α-position carbon atom) means a carbon atom to which a benzene ring is bonded unless otherwise noted.

"Structural unit derived from the styrene" and "structural unit derived from the styrene derivative" mean structural units formed by cleavage of an ethylenic double bond of the styrene or the styrene derivative.

The alkyl group as the α-position substituent is preferably a linear or branched alkyl group, and specifically, examples thereof include an alkyl group having 1 to 5 carbon atoms (a methyl group, an ethyl group, a propyl group, an isopropyl group, an n-butyl group, an isobutyl group, a tert-butyl group, a pentyl group, an isopentyl group, and a neopentyl group).

In addition, specific examples of the halogenated alkyl group as the α-position substituent include a group obtained by substituting at least one hydrogen atom of "the alkyl group as the α-position substituent" with a halogen atom. Examples of the halogen atom include a fluorine atom, a chlorine atom, a bromine atom, and an iodine atom, and particularly, a fluorine atom is preferable.

Further, specific examples of the hydroxyalkyl group as the α-position substituent include a group obtained by substituting at least one hydrogen atom of the "alkyl group as the α-position substituent" with a hydroxyl group. The number of the hydroxyl groups in the hydroxyalkyl group is preferably 1 to 5, and is most preferably 1.

Resist Composition

The resist composition according to the first aspect of the present invention is a resist composition which generates an acid upon exposure and whose solubility in a developing solution changes under the action of an acid, and includes a base material component (A) (hereinafter, also referred to as "(A) component" in some cases) whose solubility in the developing solution changes under the action of the acid, and a fluorine additive component (F) (hereinafter, "(F) component" in some cases) which exhibits the decomposability with respect to the alkali developing solution, in which the base material component (A) contains a resin component (A1) having a structural unit (a10) represented by general formula (a10-1) which is 10 mol % or more, and a structural unit (a1) which contains an acid-decomposable group having polarity increased under the action of the acid, and is 30 mol % or more, and the fluorine additive component (F) contains a fluororesin component (F1) having a structural unit (f1) containing a base dissociable group.

In the present invention, the (A) component may consist of a polymer compound, or may consist of a plurality of polymer compounds.

When a resist film is formed by using the resist composition, and the resist film is selectively exposed to the light, an acid is generated in the exposed area, and the solubility of the (A) component in the developing solution changes under the action of the acid; on the other hand, the solubility of the (A) component with respect to the developing solution is not changed in the unexposed area. Therefore, a difference in the solubility with respect to the developing solution occurs between the exposed area and the unexposed area. For this reason, when the resist film is developed, in a case where the resist composition is a positive-type, the exposed area is dissolved and removed so as to form a positive-type resist pattern, and in a case where the resist composition is a negative-type, the unexposed area is dissolved and removed so as to form a negative-type resist pattern.

In the present specification, such a resist composition that the exposed area is dissolved and removed to form the positive-type resist pattern is referred to as a positive-type resist composition, and such a resist composition that the unexposed area is dissolved and removed to form a negative-type resist pattern is referred to as a negative-type resist composition.

The resist composition of the present invention may be a positive-type resist composition, or may be a negative-type resist composition.

Further, the resist composition of the present invention may be used for an alkali developing process in which an alkali developing solution is used for a developing treatment at the time of forming a resist pattern, or may be used for a solvent developing process in which a developing solution (an organic developing solution) containing an organic solvent is used for the developing treatment. Here, the resist composition of the present invention is preferably used for the alkali developing process.

In the present invention, the resist composition has an acid generating ability to generate an acid upon exposure, and the (A) component may generate an acid upon exposure, and an additive component compounded separately from the (A) component may generate an acid upon exposure.

Specifically, the resist composition of the present invention may be (1) a composition containing an acid generator component (B) (hereinafter, referred to as "(B) component") which generates an acid upon exposure, (2) the (A) component may be a component which generates an acid upon exposure, and (3) the (A) component may be the component which generates an acid upon exposure, and may further contain the (B) component is further included.

That is, in cases of the above descriptions (2) and (3), the (A) component is "a base material component which generates an acid upon exposure and whose solubility in the developing solution changes under the action of the acid". In a case where the (A) component is the base material component which generates an acid upon exposure and whose solubility in the developing solution changes under the action of the acid, an (A1) component described below is preferably a polymer compound which generates an acid upon exposure and whose solubility in the developing solution changes under the action of the acid. Examples of such a polymer compound include a resin having a structural unit which generates an acid upon exposure. As the structural unit which generates an acid upon exposure, well-known structural units can be used.

In the present invention, the resist composition is particularly preferable to be in a case of the above (1).

(A) Component

The "base material component" in the present invention is an organic compound having film-forming ability, and is preferably an organic compound having the molecular weight of 500 or more. When the molecular weight of the organic compound is 500 or more, the film-forming ability is improved, and a photosensitive resin pattern at a nano level is easily formed.

The organic compound used as a base material component is generally classified into a non-polymer and a polymer.

Generally, a non-polymer having a molecular weight of 500 or more and less than 4,000 is used as the non-polymer. Hereinafter, a non-polymer having a molecular weight of 500 or more and less than 4,000 is referred to as "low molecule compound".

Generally, a polymer having a molecular weight of 1,000 or more is used. Hereinafter, a polymer having a molecular weight of 1,000 or more is referred to as "resin".

As the molecular weight of the polymer, the mass average molecular weight expressed by gel permeation chromatography (GPC) in terms of polystyrene is used.

As the (A) component, a resin may be used, a low molecule compound may be used, and these may be used in combination.

The (A) component may be a component whose solubility with respect to a developing solution is increased under the action of an acid, or may be a component whose solubility with respect to a developing solution is decreased under the action of an acid.

In addition, the (A) component in the present invention may be a component which generates an acid upon exposure.

Structural Unit (a10)

A structural unit (a10) is a structural unit represented by general formula (a10-1).

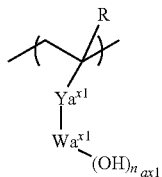

(a10-1)

In the formula, R is a hydrogen atom, an alkyl group having 1 to 5 carbon atoms, or a halogenated alkyl group having 1 to 5 carbon atoms. $Ya^{x1}$ is a single bond or a divalent linking group. $Wa^{x1}$ is a $(n_{ax1}+1)$ valent aromatic hydrocarbon group which may have a substituent. $na_{x1}$ is an integer of 1 to 3.

In general formula (a10-1), an alkyl group having 1 to 5 carbon atoms for R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. A halogenated alkyl group having 1 to 5 carbon atoms is a group obtained by substituting at least one hydrogen atom of an alkyl group having 1 to 5 carbon atoms with a halogen atom. Examples of the halogen atom include a fluorine atom, a chlorine atom, a bromine atom, and an iodine atom, and the fluorine atom is particularly preferable.

R is preferably a hydrogen atom, an alkyl group having 1 to 5 carbon atoms, or a fluorinated alkyl group having 1 to 5 carbon atoms, and a hydrogen atom or a methyl group is most preferable in terms of industrial availability.

In general formula (a10-1), examples of the divalent linking group for $Ya^{x1}$ include the same divalent linking group for $Ya^{21}$ in general formula (a2-1). $Ya^{x1}$ is preferably a single bond.

Examples of the aromatic hydrocarbon group for $Wa^{x1}$ include a group obtained by removing $(n_{ax1}+1)$ hydrogen atoms from the aromatic ring. Here, the aromatic ring is not particularly limited as long as it is a cyclic conjugated system having $(4n+2)$ π-electrons, and it may be monocyclic or polycyclic. The number of carbon atoms of the aromatic ring is preferably 5 to 30, is further preferably 5 to 20, is still further preferably 6 to 15, and is particularlypreferably 6 to 12. Specific examples of the aromatic ring include an aromatic hydrocarbon ring such as benzene, naphthalene, anthracene, and phenanthrene; and aromatic heterocycle in which a portion of carbon atoms forming the aromatic hydrocarbon ring is substituted with a heteroatom. Examples of the heteroatom in the aromatic heterocycle include an oxygen atom, a sulfur atom, and a nitrogen atom. Specific examples of the aromatic heterocycle include a pyridine ring and a thiophene ring.

In general formula (a10-1), $n_{ax1}$ is an integer of 1 to 3, is preferably 1 or 2, and is further preferably 1.

Specific examples of the structural unit represented by general formula (a10-1) are described below. In the formula, $R^{\alpha}$ represents a hydrogen atom, a methyl group, or a trifluoromethyl group.

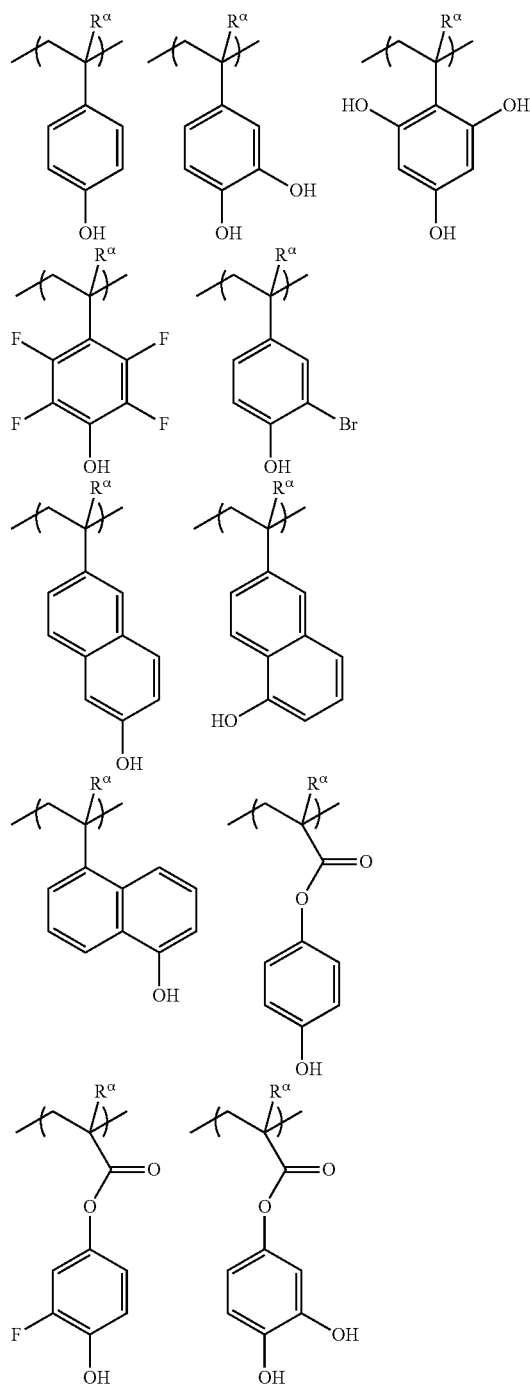

-continued

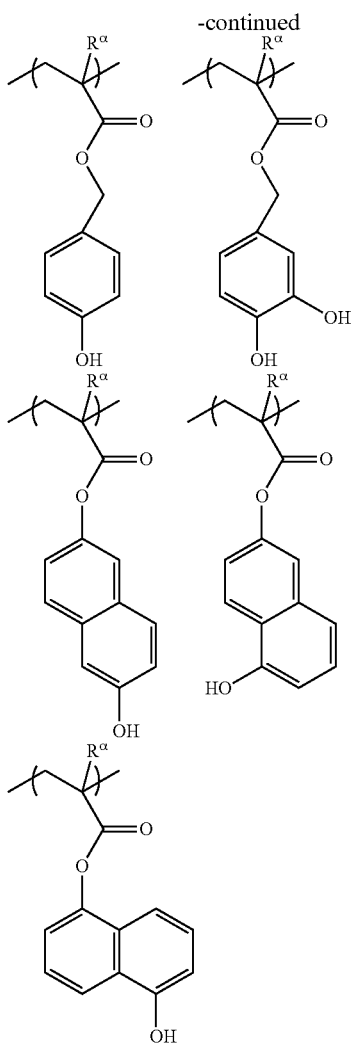

The structural unit (a10) contained in the (A1) component may be used alone, or two or more kinds thereof may be used in combination.

Among them, the structural unit (a10) is preferably a structural unit containing a hydroxystyrene skeleton, and for example, a structural unit represented by general formula (a10-1-1) is particularly preferable.

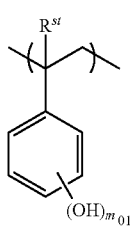

(a10-1-1)

In the formula, $R^{st}$ represents a hydrogen atom or a methyl group. $m_{01}$ represents an integer of 1 to 3.

The ratio of the structural unit (a10) in the (A1) component is equal to or greater than 10 mol %, and is further preferably equal to or greater than 20 mol % with respect to the total (100 mol %) of the structural units for constituting the (A1) component.

The upper limit value of the ratio of the structural unit (a10) is not particularly limited, and is preferably equal to or lower than 70 mol %, is further preferably equal to or lower than 65 mol %, and is particularly preferably equal to or lower than 60 mol %.

When the ratio of the structural unit (a10) is set to be equal to or greater than the lower limit value, the lithography properties such as the sensitivity, the resolution, and EL margin are improved, on the other hand, when the ratio of the structural unit (a10) is set to be equal to or lower than the upper limit value, it becomes easier to take balance with other structural units.

Structural Unit (a1)

The structural unit (a1) is a structural unit containing an acid-decomposable group in which the polarity is increased under the action of the acid.

"Acid-decomposable group" is a group having the acid decomposability with which at least a portion of the bonds in the structure of the acid-decomposable group can be cleaved under the action of the acid.

Examples of the acid-decomposable group in which the polarity is increased under the action of the acid include a group which is decomposed by the action of the acid to generate a polar group.

Examples of the polar group include a carboxy group, a hydroxyl group, an amino group, and a sulfo group ($—SO_3H$). Among them, a polar group containing —OH in the structure (hereinafter, referred to as "OH-containing polar group") is preferable, a carboxy group or a hydroxyl group is further preferable, and a carboxy group is particularly preferable.

More specifically, examples of the acid-decomposable group include a group in which the polar group is protected by an acid dissociable group (for example, a group in which a hydrogen atom of an OH-containing polar group is protected by the acid dissociable group).

Here, the "acid dissociable group" means both (i) a group having the acid dissociablility with which the bond between the acid dissociable group and the atom adjacent to the acid dissociable group can be cleaved under the action of the acid, and (ii) a group in which the bond between the acid dissociable group and the atom adjacent to the acid dissociable group can be cleaved due to decarboxylation after a portion of the bond is cleaved under the action of the acid.

The acid dissociable group for constituting an acid-decomposable group is required to be a group having the lower polarity than that of the polar group generated by dissociation of the acid dissociable group, and with this, when the acid dissociable group is dissociated under the action of the acid, a polar group having the higher polarity than that of the acid dissociable group is generated, and thereby the polarity is increased. As a result, the polarity of the entire components (A1) is increased. As the polarity is increased, the solubility in the developing solution is relatively changed, and in the case where the developing solution is an alkali developing solution, the solubility is increased; whereas, in the case where the developing solution is an organic developing solution, the solubility is decreased.

Examples of the acid dissociable group include a group which has been proposed as an acid dissociable group for a base resin for chemically amplified resist composition.

Specific examples of the group which has been proposed as an acid dissociable group of a base resin for chemically amplified resist composition include an "acetal-type acid dissociable group", a "tertiary alkyl ester-type acid dissociable group", and a "tertiary alkyloxycarbonyl acid dissociable group" which are described as follows.

Acetal-Type Acid Dissociable Group:

Among the polar groups, examples of the acid dissociable group which protects a carboxy group or a hydroxyl group include an acid dissociable group (hereinafter, referred to as the "acetal-type acid dissociable group" in some cases) represented by general formula (a1-r-1).

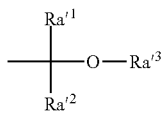

(a1-r-1)

In the formula, $Ra'^1$ and $Ra'^2$ are a hydrogen atom or an alkyl group, $Ra'^3$ is a hydrocarbon group, and $Ra'^3$ may form a ring by bonding to any of $Ra'^1$ and $Ra'^2$.

In general formula (a1-r-1), it is preferable that at least one of $Ra'^1$ and $Ra'^2$ is a hydrogen atom, and it is further preferable that both of them are a hydrogen atom.

In the case where $Ra'^1$ or $Ra'^2$ is an alkyl group, examples of the alkyl group include the same alkyl group as that exemplified as a substituent which may be bonded to the α-position carbon atom in the description of the α-substituted acrylic ester, and an alkyl group having 1 to 5 carbon atoms is preferable. Specifically, a linear or branched alkyl group is preferable. More specifically, examples thereof include a methyl group, an ethyl group, a propyl group, an isopropyl group, an n-butyl group, an isobutyl group, a tert-butyl group, a pentyl group, an isopentyl group, and a neopentyl group, and among them, the methyl group or the ethyl group is further preferable, and the methyl group is particularly preferable.

In general formula (a1-r-1), examples of the hydrocarbon group for $Ra'^3$ include a linear or branched alkyl group, and a cyclic hydrocarbon group.

The number of the carbon atoms of the linear alkyl group is preferably 1 to 5, is further preferably 1 to 4, and is still further preferably 1 or 2. Specific examples thereof include a methyl group, an ethyl group, an n-propyl group, an n-butyl group, and an n-pentyl group. Among them, the methyl group, the ethyl group, or the n-butyl group is preferable, and the methyl group or the ethyl group is further preferable.

The number of the carbon atoms of the branched alkyl group is preferably 3 to 10, and is further preferably 3 to 5. Specific examples thereof include an isopropyl group, an isobutyl group, a tert-butyl group, an isopentyl group, a neopentyl group, a 1,1-diethyl propyl group, and a 2,2-dimethyl butyl group, and among them, the isopropyl group is preferable.

In the case where $Ra'^3$ is a cyclic hydrocarbon group, the hydrocarbon group may be an aliphatic hydrocarbon group or an aromatic hydrocarbon group, and may be a polycyclic group or a monocyclic group.

The aliphatic hydrocarbon group which is a monocyclic group is preferably a group obtained by removing one hydrogen atom from monocycloalkane. The number of carbon atoms of the monocycloalkane is preferably 3 to 6, and specific examples thereof include cyclopentane and cyclohexane.

Preferred examples of the aliphatic hydrocarbon group which is the polycyclic group include a group obtained by removing one hydrogen atom from polycycloalkane. The number of the carbon atoms of polycycloalkane is preferably 7 to 12, and specific examples thereof include adamantane, norbornane, isobornane, tricyclodecane, and tetracyclododecane.

In the case where the cyclic hydrocarbon group for $Ra'^3$ is an aromatic hydrocarbon group, the aromatic hydrocarbon group is a hydrocarbon group having at least one aromatic ring.

The aromatic ring is not particularly limited as long as it is a cyclic conjugated system having (4n+2) π-electrons, and it may be monocyclic or polycyclic. The number of the carbon atoms of the aromatic ring is preferably 5 to 30, is further preferably 5 to 20, is still further preferably 6 to 15, and is particularly preferably 6 to 12.

Specific examples of the aromatic ring include an aromatic hydrocarbon ring such as benzene, naphthalene, anthracene, and phenanthrene; and aromatic heterocycle in which a portion of carbon atoms forming the aromatic hydrocarbon ring is substituted with a heteroatom. Examples of the heteroatom in the aromatic heterocycle include an oxygen atom, a sulfur atom, and a nitrogen atom. Specific examples of the aromatic heterocycle include a pyridine ring and a thiophene ring.

Specific examples of the aromatic hydrocarbon group for $Ra'^3$ include a group (an aryl group or a heteroaryl group) obtained by removing one hydrogen atom from an aromatic hydrocarbon ring or an aromatic heterocycle; a group obtained by removing one hydrogen atom from an aromatic compound (for example, biphenyl and fluorene) containing two or more aromatic rings; and a group (for example, an aryl alkyl group such as a benzyl group, a phenethyl group, a 1-naphthyl methyl group, a 2-naphthyl methyl group, a 1-naphthyl ethyl group, and a 2-naphthyl ethyl group) obtained by substituting one hydrogen atom of the aromatic hydrocarbon ring or the aromatic heterocycle with an alkylene group. The number of the carbon atoms of the alkylene group which is bonded to the aromatic hydrocarbon ring or the aromatic heterocycle is preferably 1 to 4, is further preferably 1 to 2, and is particularly preferably 1.

The cyclic hydrocarbon group for $Ra'^3$ may have a substituent. Examples thereof include $—R^{P1}$, $—R^{P2}—O—R^{P1}$, $—R^{P2}—CO—R^{P1}$, $—R^{P2}—CO—OR^{P1}$, $—R^{P2}—O—CO—R^{P1}$, $—R^{P2}—OH$, $—R^{P2}—CN$ or $—R^{P2}—COOH$ (hereinafter, these substituents are collectively referred to "$Ra^{05}$").

Here, $R^{P1}$ is a monovalent chain saturated hydrocarbon group having 1 to 10 carbon atoms, monovalent aliphatic cyclic saturated hydrocarbon group having 3 to 20 carbon atoms, or monovalent aromatic hydrocarbon group having 6 to 30 carbon atoms. In addition, $R^{P2}$ is a single bond, a divalent chain saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms.

Here, at least one hydrogen atom of the chain saturated hydrocarbon group, the aliphatic cyclic saturated hydrocarbon group, or the aromatic hydrocarbon group for $R^{P1}$ and $R^{P2}$ may be substituted with a fluorine atom. The aliphatic cyclic saturated hydrocarbon group may have one or more same kinds of substituents described above, or may have one or more different kinds of substituents described above.

Examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; polycyclic aliphatic saturated hydrocarbon group such as a bicyclo [2.2.2] octanyl group, a tricyclo [5.2.1.0$^{2,6}$] decanyl group, a tricyclo [3.3.1.1$^{3,7}$] decanyl group, a tetracyclo [6.2.1.1$^{3,6}$ 0.0$^{2,7}$] dodecanyl group, and an adamantyl group.

Examples of the monovalent aromatic hydrocarbon group having 6 to 30 carbon atoms include a group obtained by removing one hydrogen atom from the aromatic hydrocarbon ring such as benzene, biphenyl, fluorene, naphthalene, anthracene, and phenanthrene.

In the case where $Ra'^3$ forms a ring by bonding to any one of $Ra'^1$ and $Ra'^2$, the cyclic group is preferably a group of 4- to 7-membered rings, and is further preferably a group of 4- to 6-membered rings. Specific examples of the cyclic group include a tetrahydropyranyl group and a tetrahydrofuranyl group.

Tertiary Alkyl Ester-Type Acid Dissociable Group:

Among the polar groups, examples of the acid dissociable group which protects a carboxy group include an acid dissociable group represented by general formula (a1-r-2).

Note that, among acid dissociable groups represented by the following formula (a1-r-2), an acid dissociable group which is composed of an alkyl group is referred to as "tertiary alkyl ester-type acid dissociable group" in some cases for the sake of convenience.

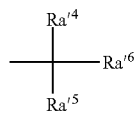

(a1-r-2)

In the formula, $Ra'^4$ to $Ra'^6$ each independently represent a hydrocarbon group, and $Ra'^3$ and $Ra'^6$ may be bonded to each other so as to form a ring.

Examples of the hydrocarbon group for $Ra'^4$ include a linear or branched alkyl group, a chain or cyclic alkenyl group, and a cyclic hydrocarbon group.

Examples of the linear or branched alkyl group, and the cyclic hydrocarbon group (an aliphatic hydrocarbon group which is a monocyclic group, an aliphatic hydrocarbon group which is a polycyclic group, and an aromatic hydrocarbon group) for $Ra'^4$ are the same as those for $Ra'^3$.

The chain or cyclic alkenyl group for $Ra'^4$ is preferably an alkenyl group having 2 to 10 carbon atoms.

Examples of the hydrocarbon group for $Ra'^3$ and $Ra'^6$ are the same as those for $Ra'^3$.

In the case where $Ra'^3$ and $Ra'^6$ are bonded to each other so as to form a ring, a group represented by general formula (a1-r2-1), a group represented by general formula (a1-r2-2), and a group represented by general formula (a1-r2-3) are suitably exemplified.

On the other hand, in the case where $Ra'^4$ to $Ra'^6$ are not bonded to each other, and are each independently a hydrocarbon group, a group represented by general formula (a1-r2-4) can be exemplified.

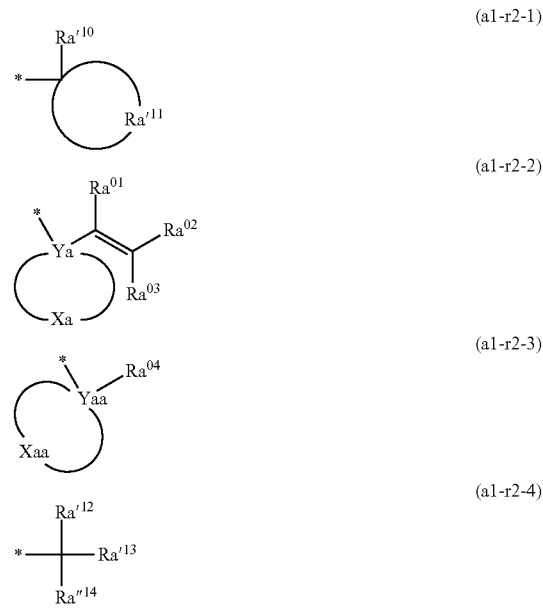

In general formula (a1-r2-1), $Ra'^{10}$ represents an alkyl group having 1 to 10 carbon atoms, and $Ra'^{11}$ represents a group which forms an aliphatic cyclic group together with a carbon atom to which $Ra'^{10}$ is bonded.

In general formula (a1-r2-2), Ya is a carbon atom. Xa is a group forming a cyclic hydrocarbon group together with Ya. At least one hydrogen atom contained in the cyclic hydrocarbon group may be substituted. $Ra^{01}$ to $Ra^{03}$ each independently represent, a hydrogen atom, a monovalent chain saturated hydrocarbon group having 1 to 10 carbon atoms, or a monovalent aliphatic cyclic saturated hydrocarbon group having 3 to 20 carbon atoms. At least one hydrogen atom contained in the chain saturated hydrocarbon group and the aliphatic cyclic saturated hydrocarbon group may be substituted. Two or more of $Ra^{01}$ to $Ra^{03}$ may be bonded to each other to form a cyclic structure. A symbol of * represents a bond.

In general formula (a1-r2-3), Yaa is a carbon atom. Xaa is a group forming an aliphatic cyclic group together with Yaa. $Ra^{04}$ is an aromatic hydrocarbon group which may have a substituent. A symbol of * represents a bond.

In general formula (a1-r2-4), $Ra'^{12}$ and $Ra'^{13}$ each independently represent a monovalent chain saturated hydrocarbon group having 1 to 10 carbon atoms or a hydrogen atom. At least one hydrogen atom of the chain saturated hydrocarbon group may be substituted. $Ra'^{14}$ is an aromatic hydrocarbon group which may have a substituent. * represents a bond (the same applies to the present specification).

In general formula (a1-r2-1), the alkyl group having 1 to 10 carbon atoms in $Ra'^{10}$ is preferably a group exemplified by a linear or branched alkyl group for $Ra'^3$ in general formula (a1-r-1).

$Ra'^{10}$ is preferably an alkyl group having 1 to 5 carbon atoms.

In general formula (a1-r2-1), an aliphatic cyclic group which is formed of $Ra'^{11}$ together with the carbon atom to which $Ra'^{10}$ is bonded is preferably a group exemplified as an aliphatic hydrocarbon group which is a monocyclic group or a polycyclic group for $Ra'^3$ in general formula (a1-r-1).

In general formula (a1-r2-2), as a cyclic hydrocarbon group which is formed of Xa together with Ya, a group obtained by removing one or more hydrogen atoms from the cyclic monovalent hydrocarbon group (an aliphatic hydrocarbon group and an aromatic hydrocarbon group) in $Ra'^3$ in general formula (a1-r-1).

The cyclic hydrocarbon group which is formed of Xa together with Ya may have a substituent. Examples of the substituent include same groups as the substituents that the cyclic hydrocarbon group for $Ra'^3$ may have.

In general formula (a1-r2-2), with respect to $Ra^{o1}$ to $Ra^{o3}$, examples of the monovalent chain saturated hydrocarbon group having 1 to 10 carbon atoms include a methyl group, an ethyl group, a propyl group, a butyl group, a pentyl group, a hexyl group, a heptyl group, an octyl group, and a decyl group.

In $Ra^{o1}$ to $Ra^{o3}$, examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, and a cyclododecyl group; a polycyclic aliphatic saturated hydrocarbon group such as a bicyclo [2.2.2] octanyl group, a tricyclo $[5.2.1.0^{2,6}]$ decanyl group, a tricyclo $[3.3.1.1^{3,7}]$ decanyl group, a tetracyclo $[6.2.1.1^{3,6}0^{2,7}]$ dodecanyl group, and an adamantyl group.

Among them, from the viewpoint of the ease of synthesis of the monomer compound which derives the structural unit (a1), $Ra^{o1}$ to $Ra^{o3}$ is preferably a hydrogen atom and a monovalent chain saturated hydrocarbon group having 1 to 10 carbon atoms, and among them, a hydrogen atom, a methyl group, and an ethyl group are still preferable, and a hydrogen atom is particularly preferable.

Examples of the chain saturated hydrocarbon group represented by $Ra^{o1}$ to $Ra^{o3}$, or the substituent having an aliphatic cyclic saturated hydrocarbon group include a group which is the same as $Ra^{o5}$.

Examples of the group containing a carbon-carbon double bond which is generated by forming a cyclic structure in which two or more of $Ra^{o1}$ to $Ra^{o3}$ are bonded to each other include a cyclopentenyl group, a cyclohexenyl group, a methylcyclopentenyl group, a methyl cyclohexenyl group, a cyclopentylideneethenyl group, and a cyclohexylideneethenyl group. Among them, from the viewpoint of the ease of synthesis of the monomer compound which derives the structural unit (a1), a cyclopentenyl group, a cyclohexenyl group, and a cyclopentylideneethenyl group are preferable.

In general formula (a1-r2-3), an aliphatic cyclic group which is formed of Xaa together with Yaa is preferably a group exemplified as an aliphatic hydrocarbon group which is a monocyclic group or a polycyclic group for $Ra'^3$ in general formula (a1-r-1).

In general formula (a1-r2-3), examples of the aromatic hydrocarbon group for $Ra^{o4}$ include a group obtained by removing one or more hydrogen atoms from an aromatic hydrocarbon ring having 5 to 30 carbon atoms. Among them, $Ra^{o4}$ is preferably a group obtained by removing one or more hydrogen atoms from an aromatic hydrocarbon ring having 6 to 15 carbon atoms, a group obtained by removing one or more hydrogen atoms from benzene, naphthalene, anthracene, or phenanthrene is further preferable, a group obtained by removing one or more hydrogen atoms from benzene, naphthalene, or anthracene is still further preferable, a group obtained by removing one or more hydrogen atoms from benzene and naphthalene is particularly preferable, and a group obtained by removing one or more hydrogen atoms from benzene is most preferable.

Examples of the substituent that $Ra^{o4}$ in general formula (a1-r2-3) may have include a methyl group, an ethyl group, a propyl group, a hydroxyl group, a carboxyl group, a halogen atom (a fluorine atom, a chlorine atom, a bromine atom, or the like), an alkoxy group (a methoxy group, an ethoxy group, a propoxy group, a butoxy group, or the like), and an alkyloxycarbonyl group.

In general formula (a1-r2-4), $Ra'^{12}$ and $Ra'^{13}$ each independently represent a monovalent chain saturated hydrocarbon group having 1 to 10 carbon atoms or a hydrogen atom. With respect to $Ra'^{12}$ and $Ra'^{13}$, examples of the monovalent chain saturated hydrocarbon group having 1 to 10 carbon atoms include the same monovalent chain saturated hydrocarbon group having 1 to 10 carbon atoms as that for $Ra^{o1}$ to $Ra^{o3}$. At least one hydrogen atom of the chain saturated hydrocarbon group may be substituted.

Among them, as $Ra'^{12}$ and $Ra'^{13}$, a hydrogen atom and an alkyl group having 1 to 5 carbon atoms are preferable, an alkyl group having 1 to 5 carbon atoms is further preferable, a methyl group and an ethyl group are still further preferable, and a methyl group is particularly preferable.

In the case where the chain saturated hydrocarbon group represented by $Ra'^{12}$ and $Ra'^{13}$ is substituted, examples of the substituent include the same group as that of $Ra^{o5}$.

In general formula (a1-r2-4), $Ra'^{14}$ is an aromatic hydrocarbon group which may have a substituent. Examples of the aromatic hydrocarbon group for $Ra'^{14}$ include the same groups as those of the aromatic hydrocarbon group for $Ra^{o4}$. Among them, $Ra'^{14}$ is preferably a group obtained by removing one or more hydrogen atoms from an aromatic hydrocarbon ring having 6 to 15 carbon atoms, is further preferably a group obtained by removing one or more hydrogen atoms from benzene, naphthalene, anthracene, or phenanthrene, is still further preferably a group obtained by removing one or more hydrogen atoms from benzene, naphthalene, or anthracene, is particularly preferably a group obtained by removing one or more hydrogen atoms from naphthalene or anthracene, and is most preferably a group obtained by removing one or more hydrogen atoms from naphthalene.

Examples of the substituent that $Ra'^{14}$ may have include the same group as the substituent that $Ra^{o4}$ may have.

In the case where $Ra'^{14}$ in general formula (a1-r2-4) is a naphthyl group, a position which is bonded to a tertiary carbon atom in general formula (a1-r2-4) may 1-position and 2-position of a naphthyl group.

In the case where $Ra'^{14}$ in general formula (a1-r2-4) is an anthryl group, a position which is bonded to a tertiary carbon atom in general formula (a1-r2-4) may be 1-position, 2-position, or 9-position of an anthryl group.

Specific examples of the group represented by general formula (a1-r2-1) include as follows.

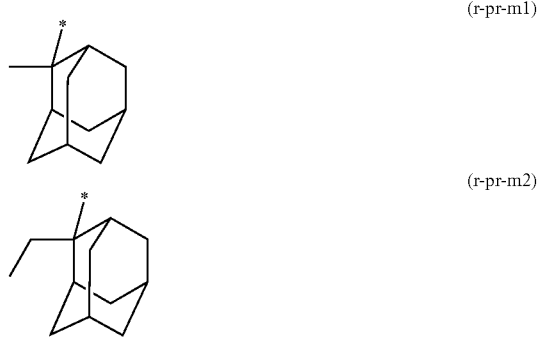

-continued
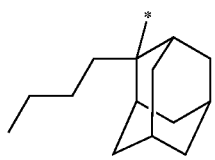
(r-pr-m3)
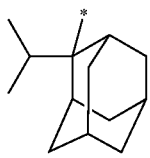
(r-pr-m4)
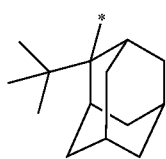
(r-pr-m5)
(r-pr-m6)
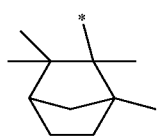
(r-pr-m7)
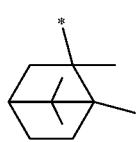
(r-pr-m8)
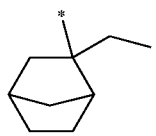
(r-pr-m9)
(r-pr-m10)
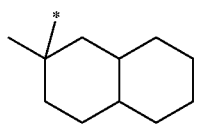
(r-pr-m11)
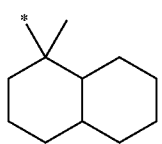
(r-pr-m12)
-continued
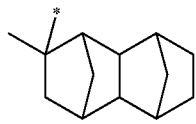
(r-pr-m13)
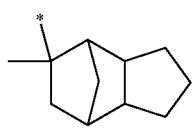
(r-pr-m14)
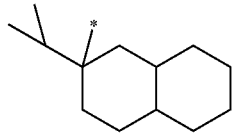
(r-pr-m15)
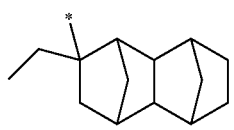
(r-pr-m16)
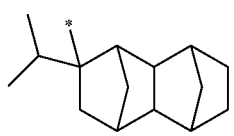
(r-pr-m17)
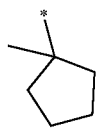
(r-pr-s1)
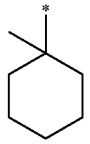
(r-pr-s2)
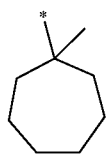
(r-pr-s3)
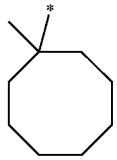
(r-pr-s4)
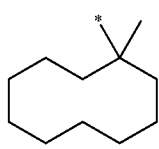
(r-pr-s5)

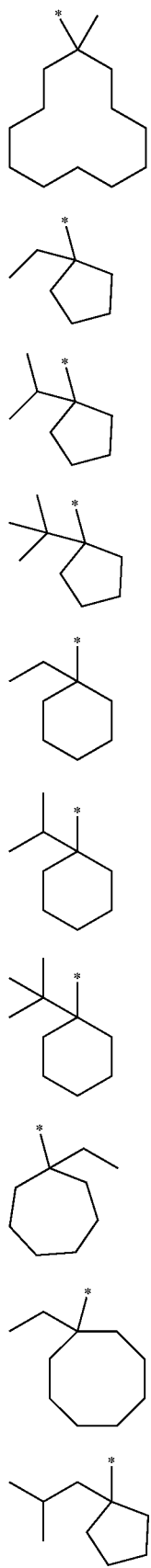
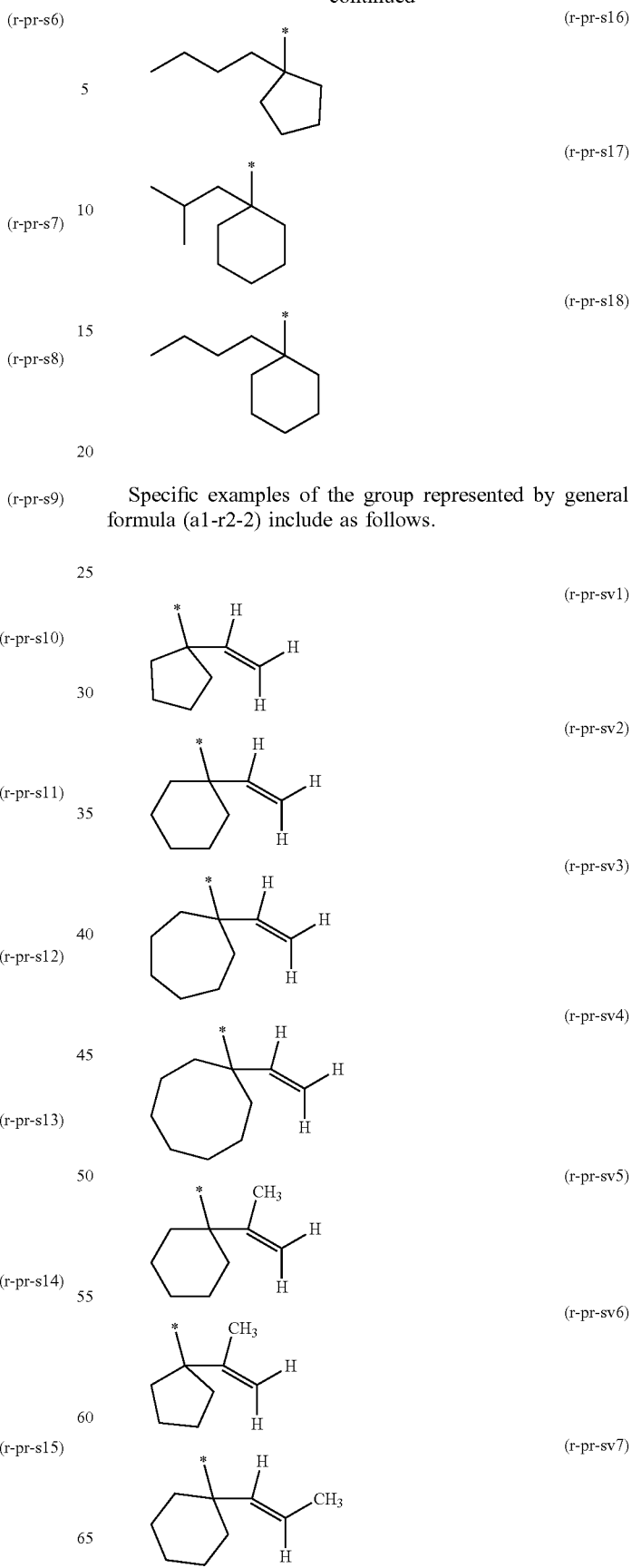
Specific examples of the group represented by general formula (a1-r2-2) include as follows.

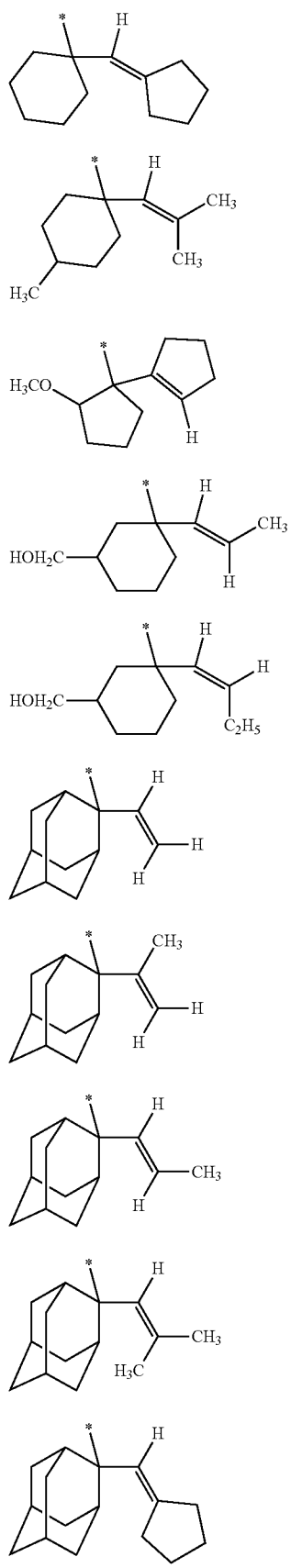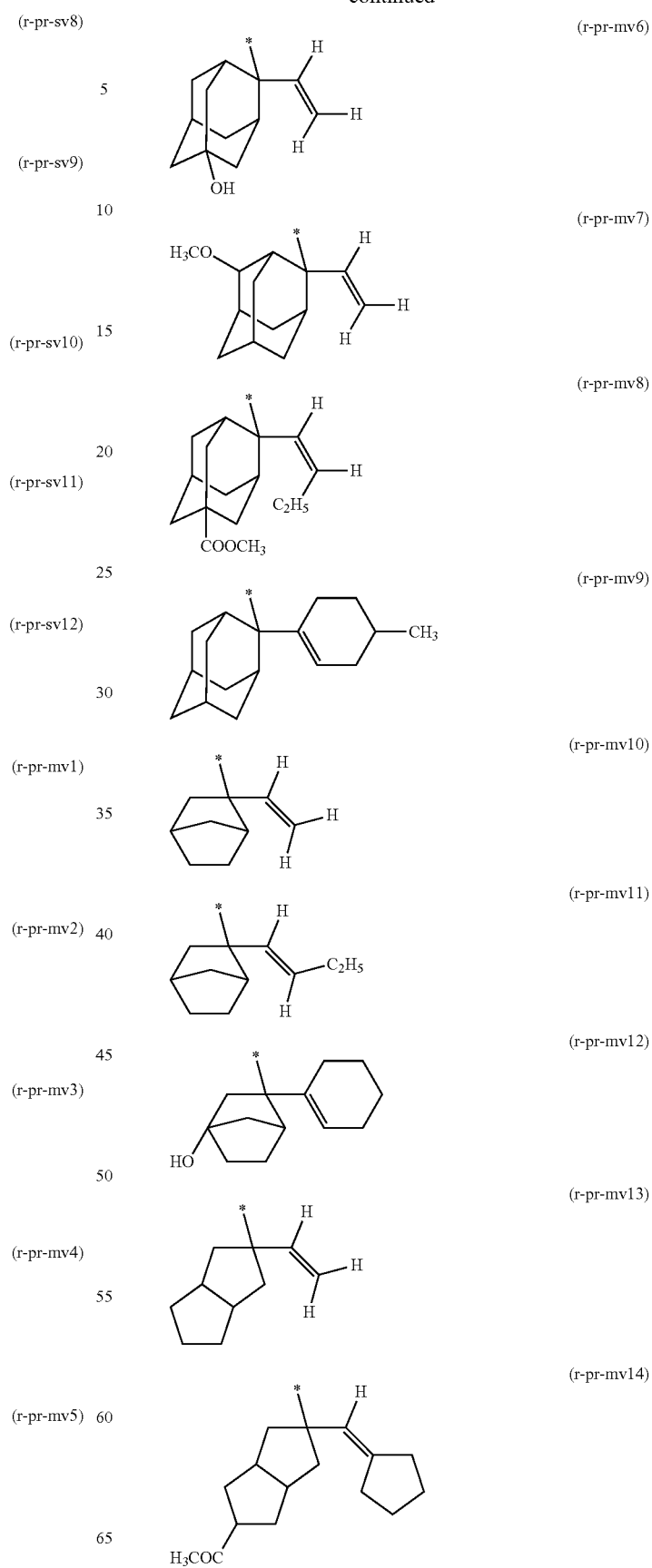

(r-pr-mv15)
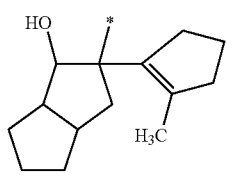
(r-pr-mv16)
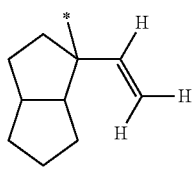
(r-pr-mv17)
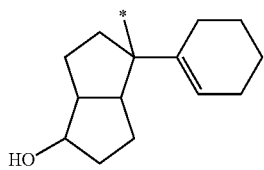
(r-pr-mv18)
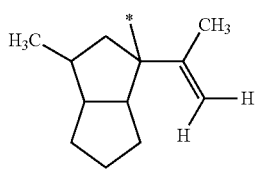
(r-pr-mv19)
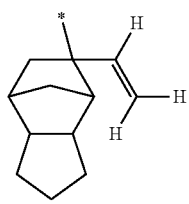
(r-pr-mv20)
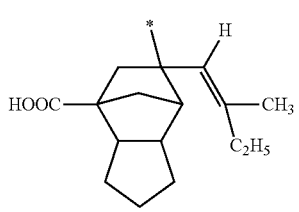
(r-pr-mv21)
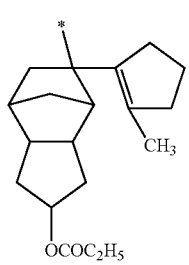
(r-pr-av1)
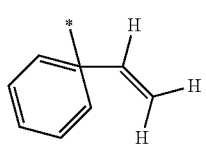
(r-pr-av2)
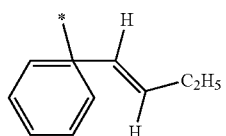
(r-pr-av3)
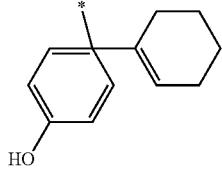
(r-pr-av4)
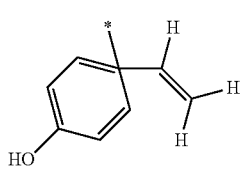
(r-pr-av5)
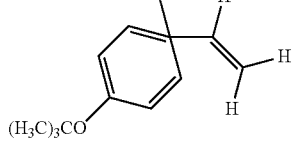
Specific examples of the group represented by general formula (a1-r2-3) include as follows.
(r-pr-sa1)
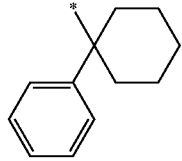
(r-pr-sa2)
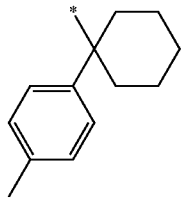
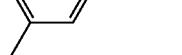
(r-pr-sa3)
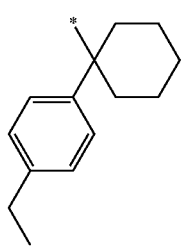
(r-pr-sa4)
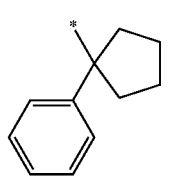

-continued (r-pr-sa5)
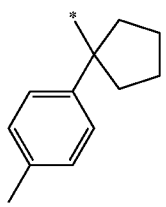

(r-pr-sa6)
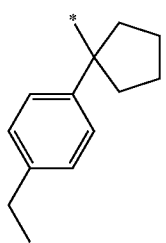

(r-pr-sa7)
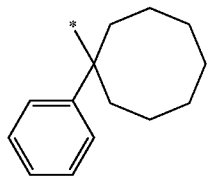

(r-pr-sa8)
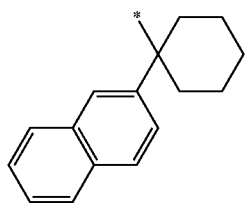

(r-pr-sa9)
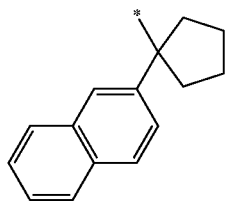

(r-pr-ma1)
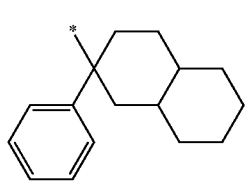

(r-pr-ma2)
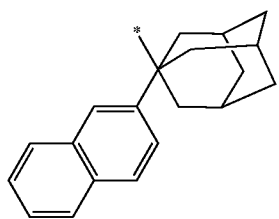

Specific examples of the group represented by general formula (a1-r2-4) include as follows.

(r-pr-cm1)
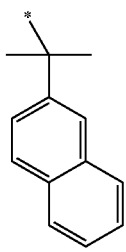

(r-pr-cm2)
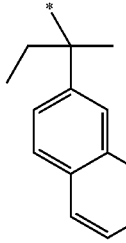

(r-pr-cm3)
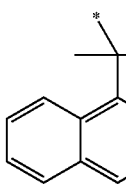

(r-pr-cm4)
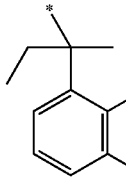

(r-pr-cs1)
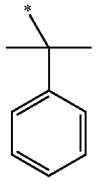

(r-pr-cs2)
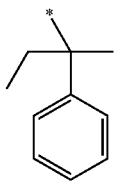

Tertiary Alkyloxycarbonyl Acid Dissociable Group:

Among the polar groups, examples of the acid dissociable group which protects a hydroxyl group include an acid dissociable group (hereinafter, referred to as "tertiary alkyloxycarbonyl acid dissociable group" for convenience) represented by general formula (a1-r-3).

(a1-r-3)

In the formula, $Ra'^7$ to $Ra'^9$ are each an alkyl group.

In general formula (a1-r-3), $Ra'^7$ to $Ra'^9$ each preferably represent an alkyl group having 1 to 5 carbon atoms, and further preferably 1 to 3.

In addition, a total number of carbon atoms of the respective alkyl groups is preferably 3 to 7, is further preferably 3 to 5, and is most preferably 3 and 4.

Examples of the structural unit (a1) include a structural unit derived from acrylic ester which may be obtained by substituting a hydrogen atom bonded to an α-position carbon atom with a substituent, a structural unit derived from acrylamide, a structural unit in which at least a portion of the hydrogen atoms of a hydroxyl group in the structural unit derived from a hydroxystyrene or a hydroxystyrene derivative is protected by a substituent containing the acid-decomposable group, and a structural unit in which at least a portion of the hydrogen atoms in —C(=O)—OH in the structural unit derived from a vinylbenzoic acid or a vinylbenzoic acid derivative is protected by a substituent containing the acid-decomposable group.

Among them, the structural unit (a1) is preferably the structural unit derived from acrylic ester which may be obtained by substituting a hydrogen atom bonded to an α-position carbon atom with a substituent.

Specific examples of the preferred structural unit (a1) include a structural unit represented by general formula (a1-1) or (a1-2).

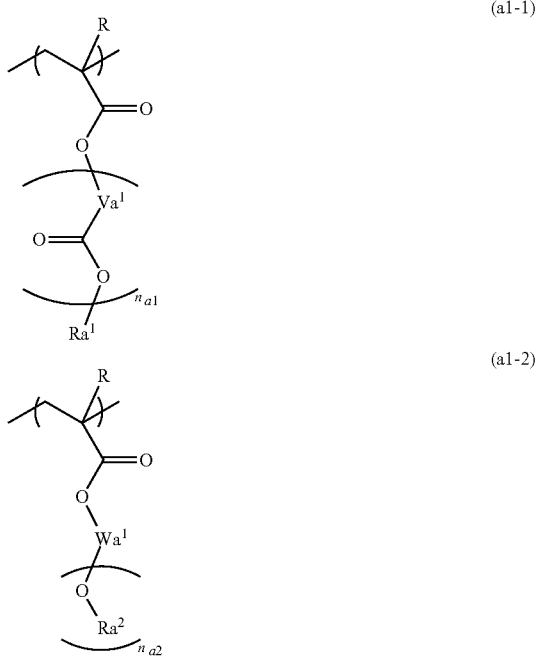

In the formulae, R is a hydrogen atom, an alkyl group having 1 to 5 carbon atoms, or a halogenated alkyl group having 1 to 5 carbon atoms. $Va^1$ is a divalent hydrocarbon group which may have an ether bond, $n_{a1}$ is an integer of 0 to 2, and $Ra^1$ is an acid dissociable group represented by general formula (a1-r-1) or (a1-r-2). $Wa^1$ is $(n_{a2}+1)$ valent hydrocarbon group, $n_{a2}$ is integer of 1 to 3, and $Ra^e$ is an acid dissociable group represented by general formula (a1-r-1) or (a1-r-3).

In general formula (a1-1), an alkyl group having 1 to 5 carbon atoms of R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. A halogenated alkyl group having 1 to 5 carbon atoms is a group obtained by substituting at least one hydrogen atom of an alkyl group having 1 to 5 carbon atoms with a halogen atom. Examples of the halogen atom include a fluorine atom, a chlorine atom, a bromine atom, and an iodine atom, and the fluorine atom is particularly preferable.

R is preferably a hydrogen atom, an alkyl group having 1 to 5 carbon atoms, or a fluorinated alkyl group having 1 to 5 carbon atoms, and a hydrogen atom or a methyl group is most preferable in terms of industrial availability.

In general formula (a1-1), the divalent hydrocarbon group for $Va^1$ may be an aliphatic hydrocarbon group, or an aromatic hydrocarbon group.

The aliphatic hydrocarbon group for $Va^1$ as the divalent hydrocarbon group may be saturated or unsaturated, and is usually preferably saturated.

Specific examples of the aliphatic hydrocarbon group include a linear or branched aliphatic hydrocarbon group, or an aliphatic hydrocarbon group including a ring in the structure.

The number of carbon atoms of the linear aliphatic hydrocarbon group is preferably 1 to 10, is further preferably 1 to 6, is further still preferably 1 to 4, and is most preferably 1 to 3.

As the linear aliphatic hydrocarbon group, the linear alkylene group is preferable, and specifically, a methylene group [—$CH_2$—], an ethylene group [—$(CH_2)_2$—], a trimethylene group [—$(CH_2)_3$—] a tetramethylene group [—$(CH_2)_4$—], and a pentamethylene group [—$(CH_2)_5$—].

The number of carbon atoms of the branched aliphatic hydrocarbon group is preferably 3 to 10, is still preferably 3 to 6, is still further preferably 3 or 4, and is most preferably 3.

As the branched aliphatic hydrocarbon group, a branched alkylene group is preferable. Specifically, examples thereof include an alkyl alkylene group such as an alkyl methylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an alkyl ethylene group such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; an alkyl trimethylene group such as —$CH(CH_3)CH_2CH_2$— and —$CH_2CH(CH_3)CH_2$—; an alkyl tetramethylene group such as —$CH(CH_3)CH_2CH_2CH_2$— and —$CH_2CH(CH_3)CH_2CH_2$—. The alkyl group in the alkyl alkylene group is preferably a linear alkyl group having 1 to 5 carbon atoms.

As the aliphatic hydrocarbon group containing a ring in the structure, an alicyclic hydrocarbon group (a group obtained by removing two hydrogen atoms from an aliphatic hydrocarbon ring), a group in which the alicyclic hydrocarbon group is bonded to a terminal of the linear or branched aliphatic hydrocarbon group, and a group in which the alicyclic hydrocarbon group is present in the middle of the linear or branched aliphatic hydrocarbon group. Examples of the linear or branched aliphatic hydrocarbon group include the same group as the linear aliphatic hydrocarbon group or the branched aliphatic hydrocarbon group described above.

The number of carbon atoms of the alicyclic hydrocarbon group is preferably 3 to 20, and is further preferably 3 to 12.

The alicyclic hydrocarbon group may be a polycyclic group, and may be a monocyclic group. The monocyclic alicyclic hydrocarbon group is preferably a group obtained by removing two hydrogen atoms from the monocycloalkane. The number of the carbon atoms of the monocycloalkane is preferably 3 to 6, and specific examples thereof include cyclopentane and cyclohexane.

The polycyclic alicyclic hydrocarbon group is preferably a group obtained by removing two hydrogen atoms from the polycycloalkane, and the number of the carbon atoms of the polycycloalkane is preferably 7 to 12. Specific examples thereof include adamantane, norbornane, isobornane, tricyclodecane, and tetracyclododecane. [ 0081] The aromatic hydrocarbon group as a divalent hydrocarbon group for Va$^1$ is a hydrocarbon group having an aromatic ring.

The number of carbon atoms of the aromatic hydrocarbon group is preferably 3 to 30, is further preferably 5 to 30, is still further preferably 5 to 20, is particularly, preferably 6 to 15, and is most preferably 6 to 10. Here, it is assumed that the number of carbon atoms does not include the number of carbon atoms in the substituent.

Specific examples of the aromatic ring having an aromatic hydrocarbon group include an aromatic hydrocarbon ring such as benzene, biphenyl, fluorene, naphthalene, anthracene, and phenanthrene; and aromatic heterocycle in which a portion of the carbon atoms which constitute the aromatic hydrocarbon ring is substituted with a heteroatom. Examples of the heteroatom in the aromatic heterocycle include an oxygen atom, a sulfur atom, and a nitrogen atom.

Specific examples of the aromatic hydrocarbon group include a group (an arylene group) obtained by removing two hydrogen atoms from the above-mentioned aromatic hydrocarbon ring; and a group in which one hydrogen atom of a group (an aryl group) obtained by removing one hydrogen atom from the above-mentioned aromatic hydrocarbon ring is substituted with an alkylene group (for example, a group obtained by removing one hydrogen atom from an aryl group in an aryl alkyl group, such as a benzyl group, a phenethyl group, a 1-naphthyl methyl group, a 2-naphthyl methyl group, a 1-naphthyl ethyl group, and a 2-naphthyl ethyl group). The number of carbon atoms of the alkylene group (an alkyl chain in the aryl alkyl group) is preferably 1 to 4, is further preferably 1 and 2, and is particularly preferably 1.

In general formula (a1-1), Ra$^1$ is an acid dissociable group represented by general formula (a1-r-1) or (a1-r-2).

In general formula (a1-2), the $(n_{a2}+1)$ valent hydrocarbon group for Wa$^1$ may be an aliphatic hydrocarbon group, or may be an aromatic hydrocarbon group. The aliphatic hydrocarbon group means a hydrocarbon group having no aromaticity, and may be saturated or unsaturated, and generally it is preferably saturated. Examples of the aliphatic hydrocarbon group include a linear or branched aliphatic hydrocarbon group, an aliphatic hydrocarbon group containing a ring in the structure, and a group in which a linear or branched aliphatic hydrocarbon group and the aliphatic hydrocarbon group containing the ring in the structure is combined with each other.

The $(n_{a2}+1)$ valent is preferably to be divalent to tetravalent, and is further preferably to be divalent or trivalent.

Hereinafter, specific examples of the structural unit represented by general formula (a1-1) are described. In the following formulae, R$^\alpha$ represents a hydrogen atom, a methyl group, or a trifluoromethyl group.

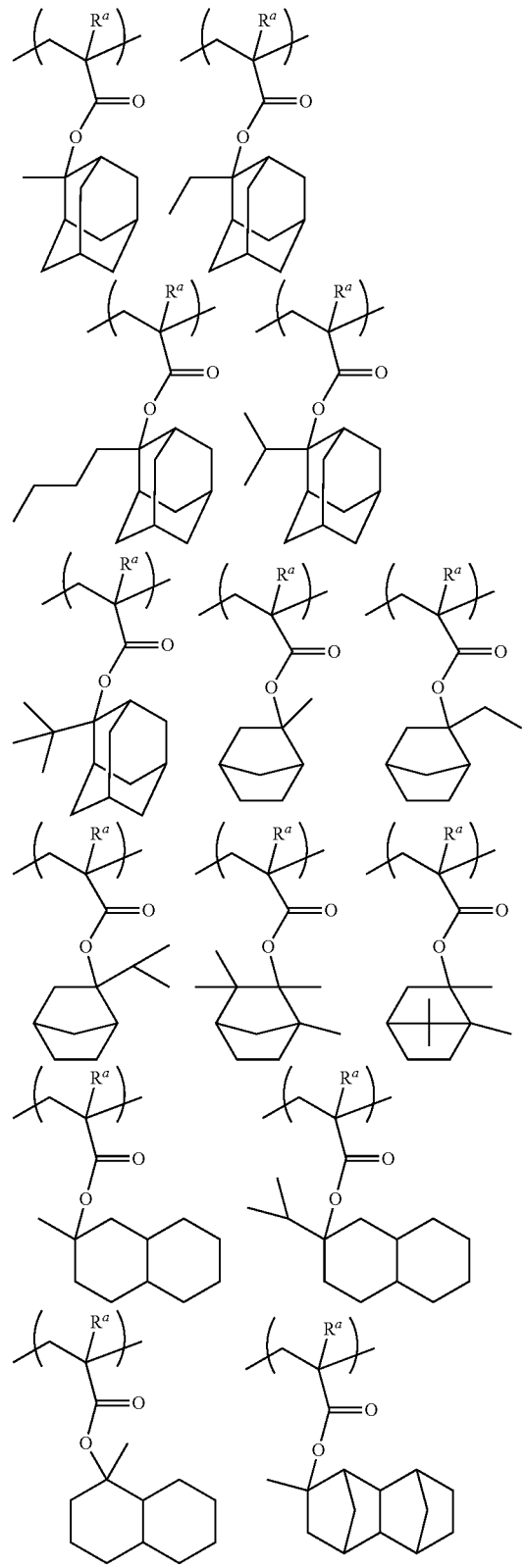

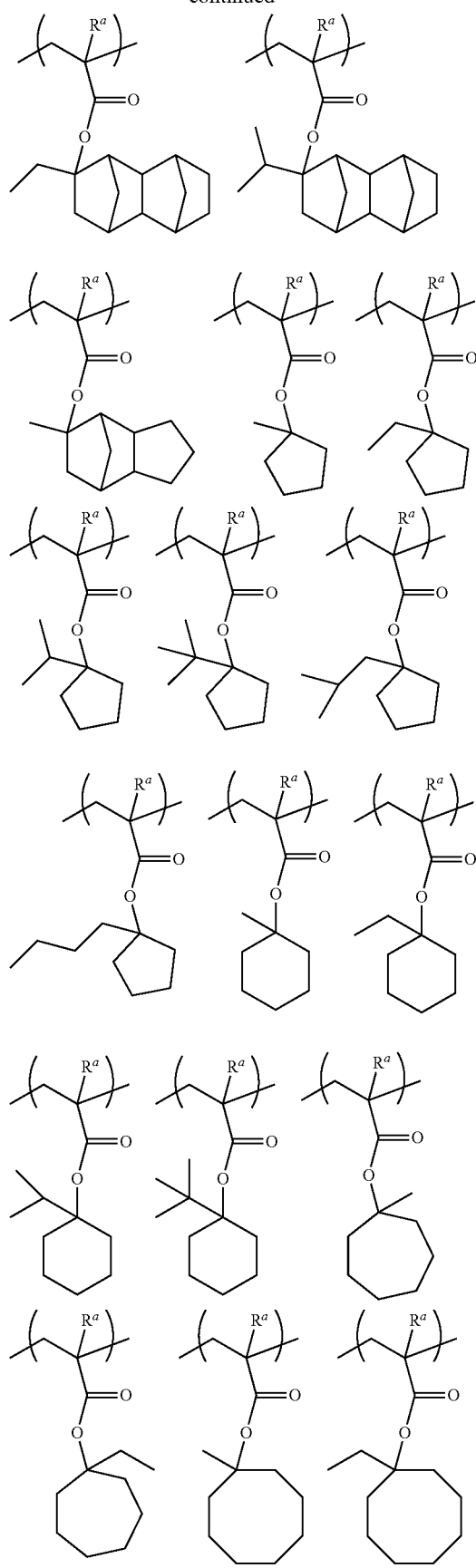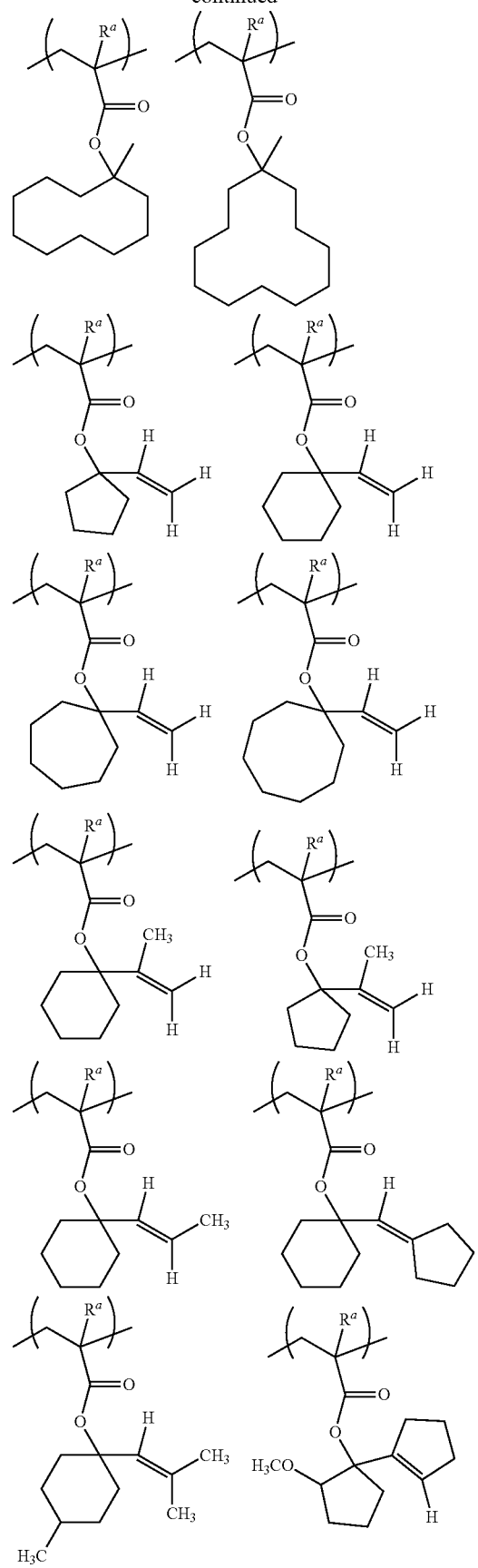

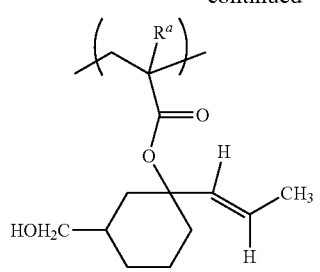
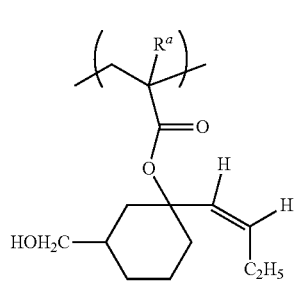
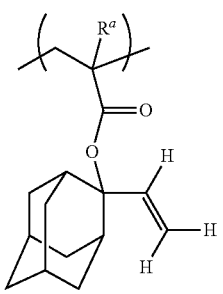
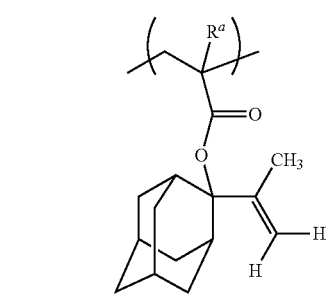
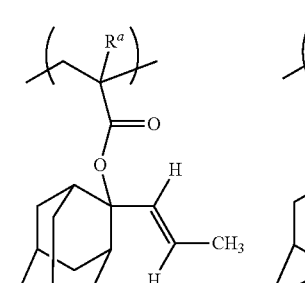
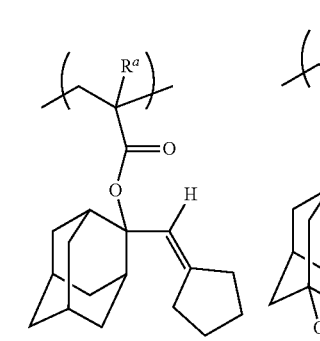
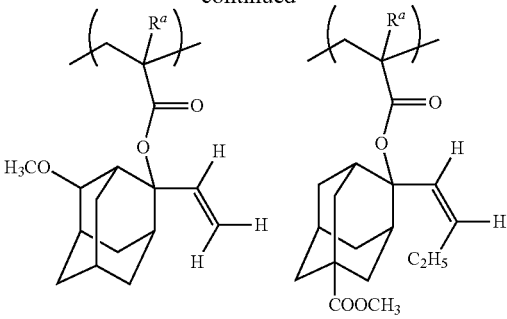
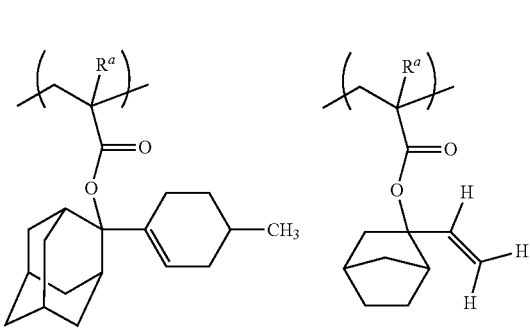
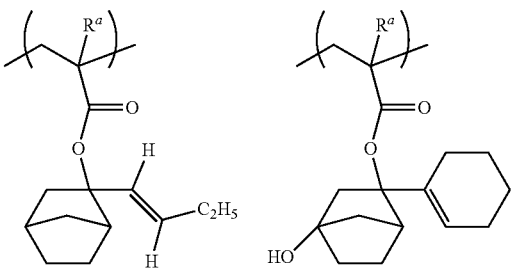
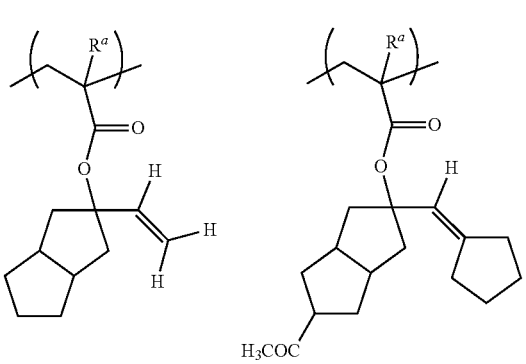
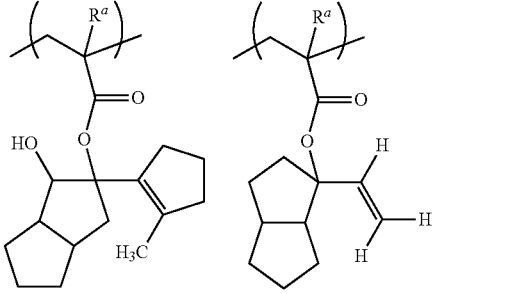

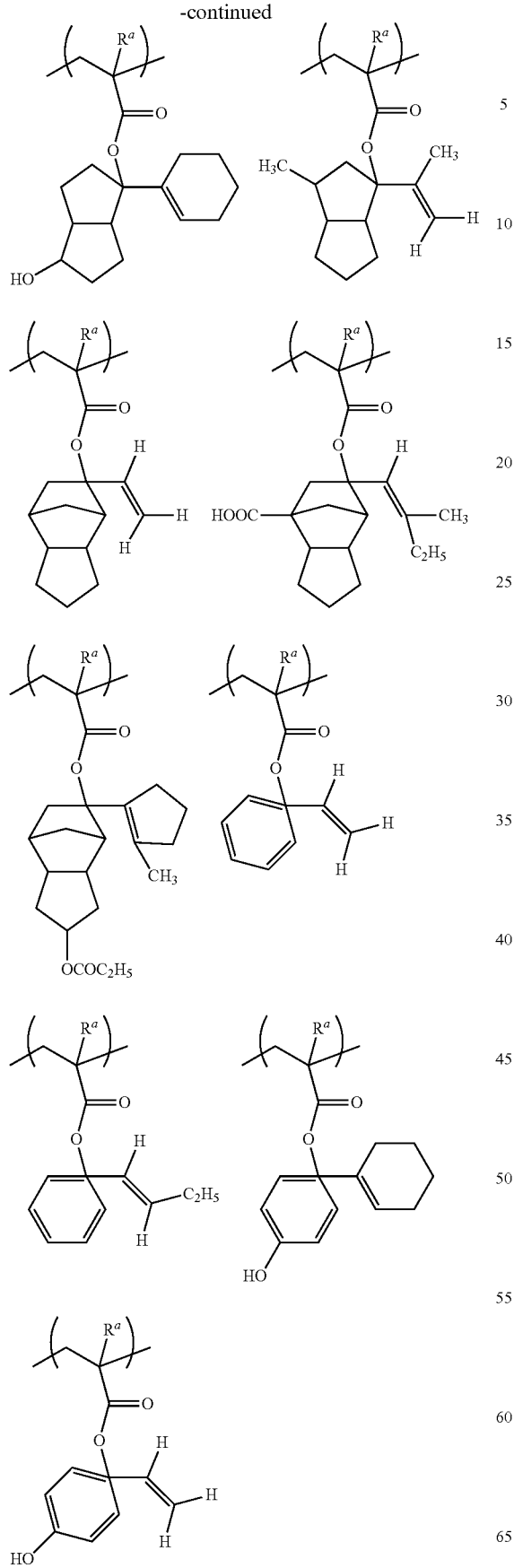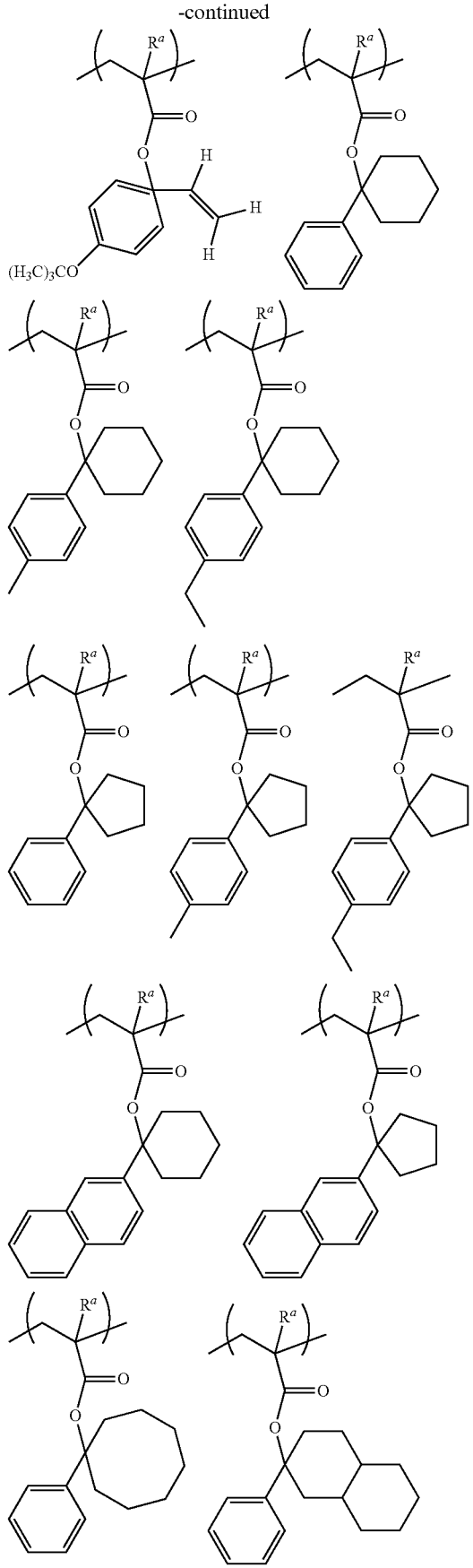

-continued
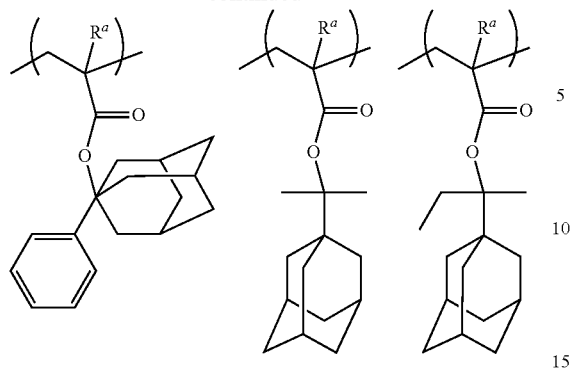
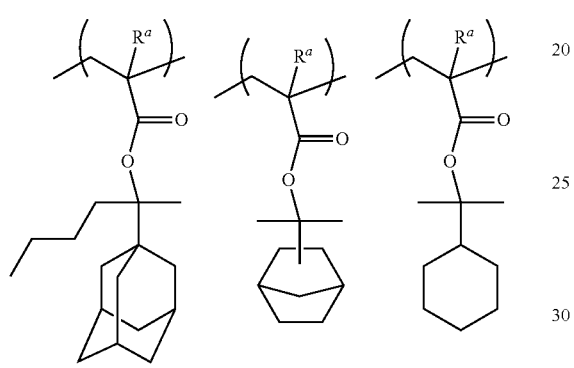
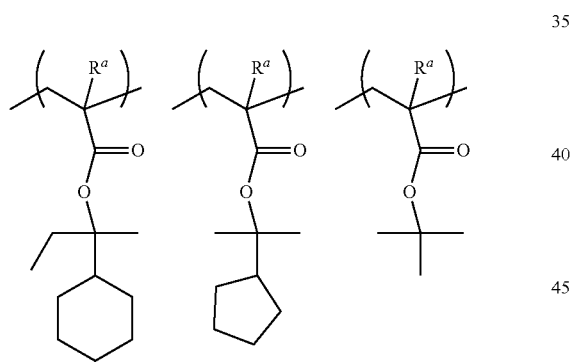
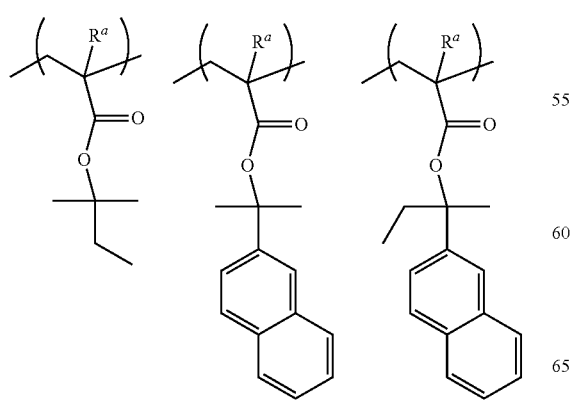
-continued
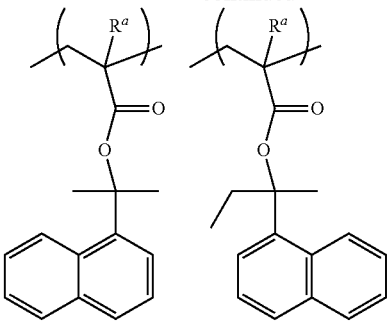
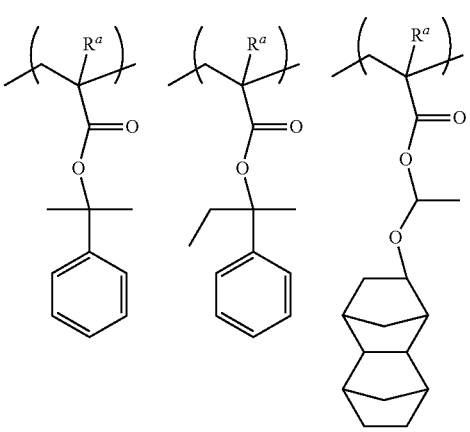
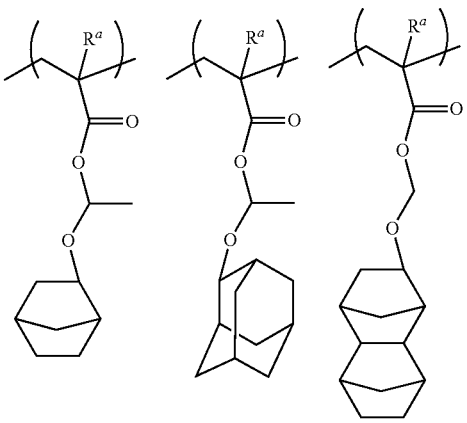
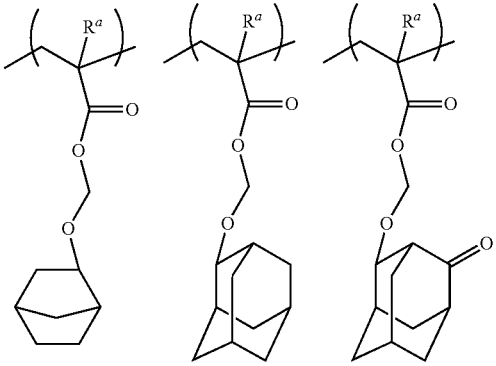

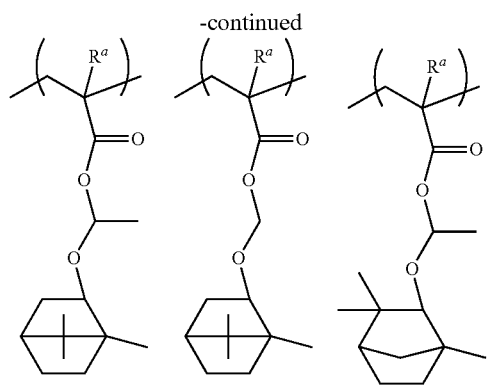
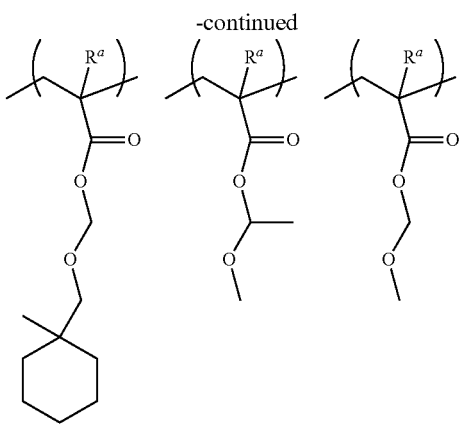
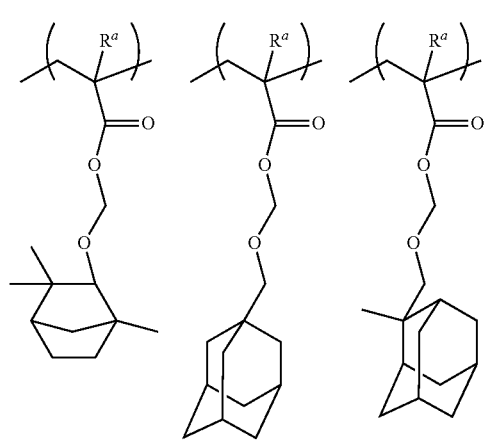
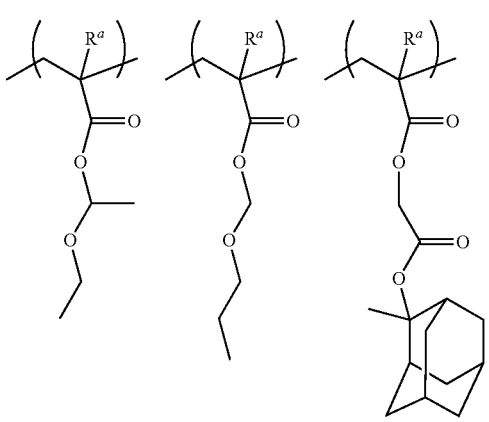
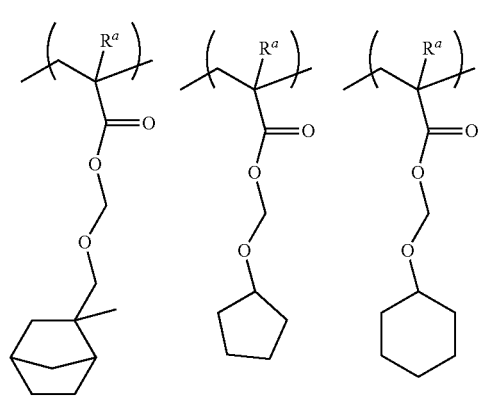
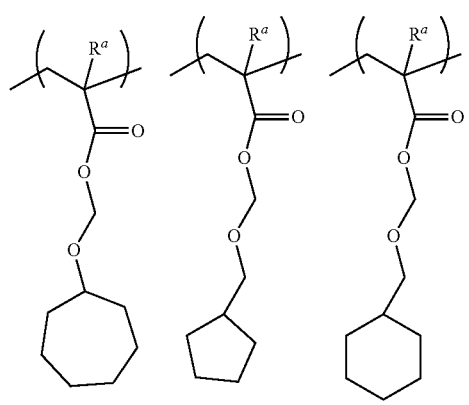
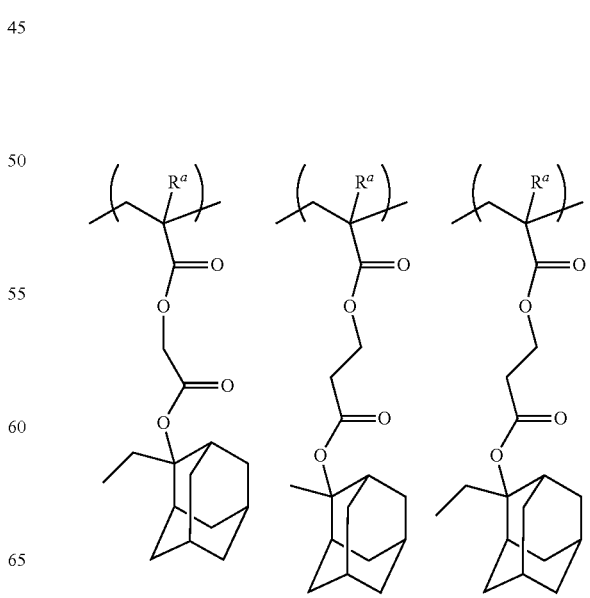

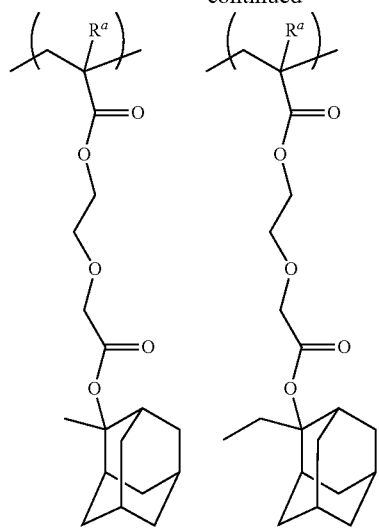
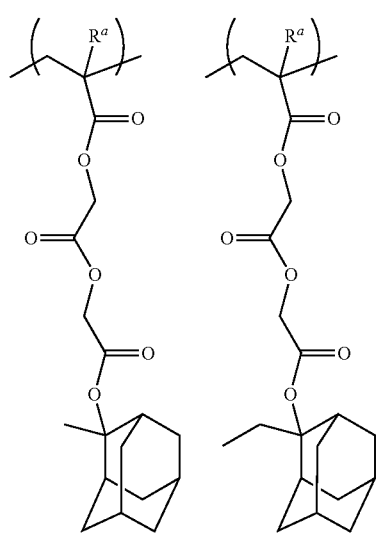
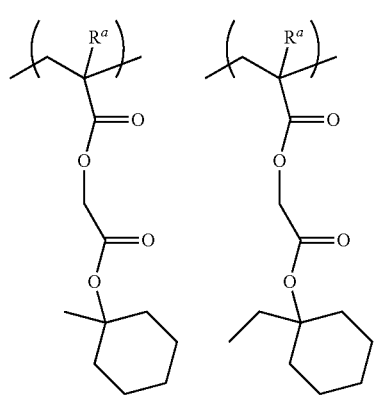
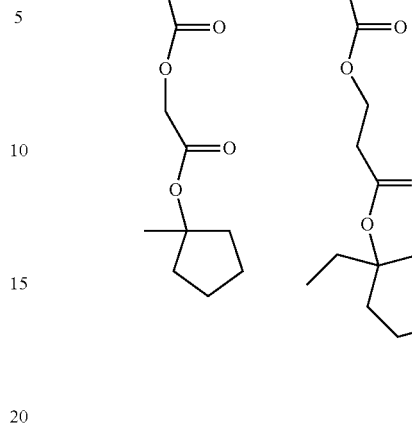
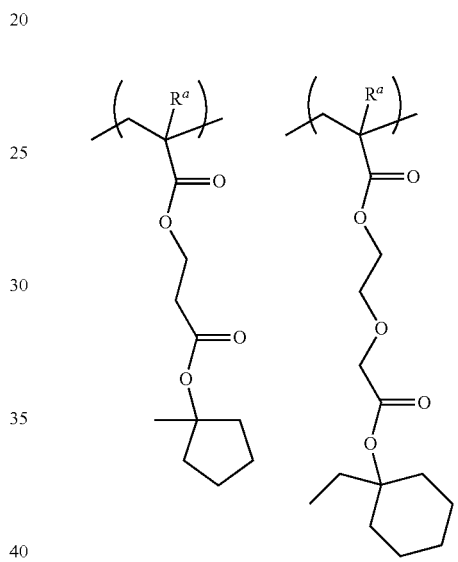
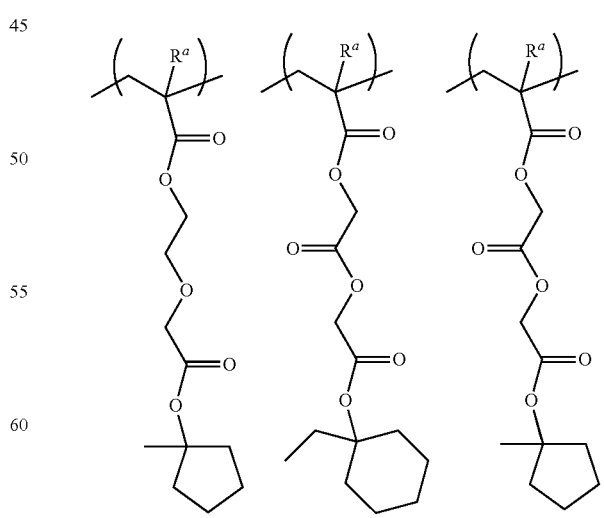
Specific examples of the structural unit represented by general formula (a1-2) are described.

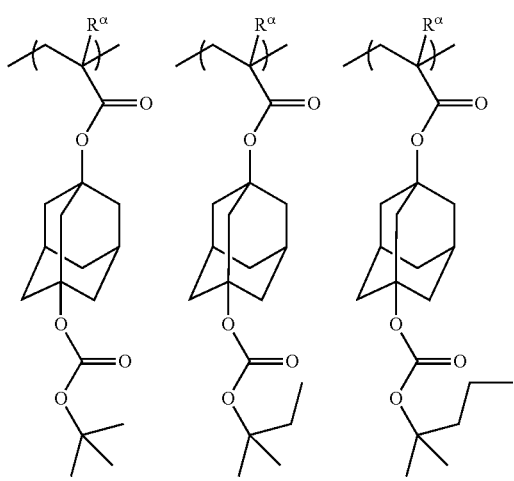
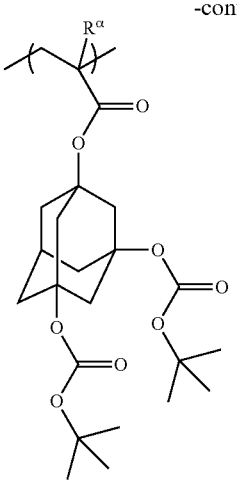
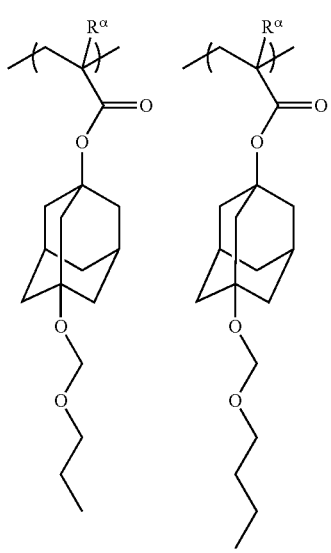
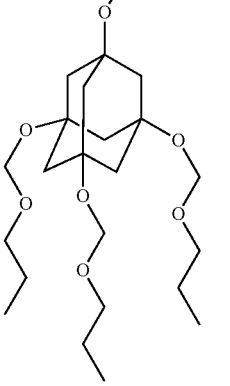
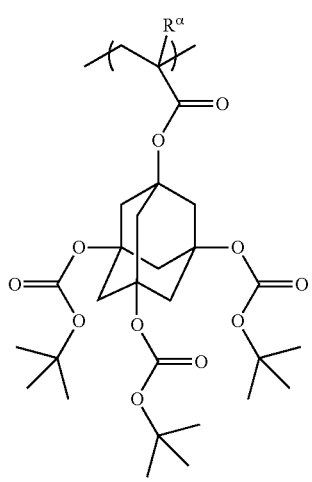

The structural unit (a1) of the (A1) component may be used alone, or two or more kinds thereof may be used in combination.

From the viewpoint that the properties of the lithography (sensitivity, shape, and the like) by electron beam and EUV are more likely to be enhanced, the structural unit (a1) is further preferably a structural unit represented by general formula (a1-1).

Among them, a structural unit (a1) having a structural unit represented by general formula (a1-1-1) is particularly preferable.

(a1-1-1)

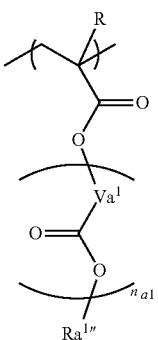

-continued

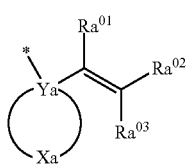
(a1-r2-2)

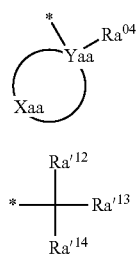
(a1-r2-3)

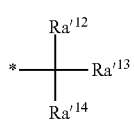
(a1-r2-4)

In the formula, Ra$^{1\prime\prime}$ is an acid dissociable group represented by general formula (a1-r2-2), (a1-r2-3), or (a1-r2-4).

In general formula (a1-1-1), R, Va$^1$, and n$_{a1}$ are the same as R, Va$^1$, and n$_{a1}$ in general formula (a1-1).

The description of the acid dissociable group represented by general formula (a1-r2-2), (a1-r2-3), or (a1-r2-4) is as described below.

The ratio of the structural unit (a1) in the (A1) component is equal to or greater than 30 mol %, is preferably equal to or greater than 40 mol %, and is further preferably equal to or greater than 50 mol %, with respect to the total (100 mol %) of the entire structural units constituting the (A1) component. The upper limit value of the ratio of the structural unit (a1) is not particularly limited. For example, it is preferably equal to or lower than 70 mol %, is preferably equal to or lower than 65 mol %, and is still further preferably equal to or lower than 60 mol %.

When the ratio of the structural unit (a1) is set to be equal to or greater than the lower limit value, it is possible to easily obtain a resist pattern, and the lithography properties such as resolution performance, and roughness improvement are also improved. In addition, when the ratio of the structural unit (a1) is set to be equal to or lower the upper limit, it is possible to take balance with other structural units.

Structural Unit (a2)

The (A1) component preferably has a structural unit (a2) containing a lactone-containing cyclic group, a —SO$_2$— containing cyclic group or a carbonate-containing cyclic group in addition to the structural units (a10) and (a1) (here, except for a structural unit corresponding to the structural (a1)).

In the case where the (A1) component is used for forming a resist film, the lactone-containing cyclic group, the —SO$_2$- containing cyclic group, or the carbonate-containing cyclic group of the structural unit (a2) is effective in improving the adhesiveness with respect to the substrate of the resist film. In addition, when the (A1) component has the structural unit (a2), the solubility of the resist film in alkali developing solution is increased at the time of developing in the alkali developing process.

The "lactone-containing cyclic group" means a cyclic group containing a ring (lactone ring) including —O—C (=O)— in the cyclic skeleton. When the lactone ring is counted as the first ring, if there is only the lactone ring, the cyclic group is referred to as a monocyclic group, and if there are other ring structures in addition to the lactone ring, the cyclic group is referred to as a polycyclic group regardless of its structure. The lactone-containing cyclic group may be a monocyclic group, or may be a polycyclic group.

The lactone-containing cyclic group in the structural unit (a2) is not particularly limited, and any lactone-containing cyclic group can be used. Specific examples thereof include groups respectively represented by general formulae (a2-r-1) to (a2-r-7).

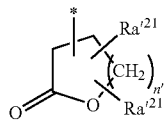
(a2-r-1)

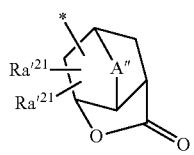
(a2-r-2)

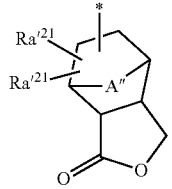
(a2-r-3)

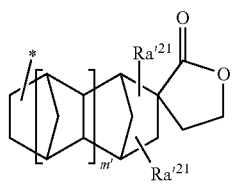
(a2-r-4)

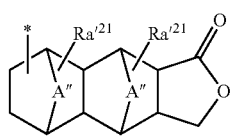
(a2-r-5)

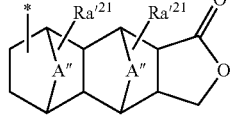
(a2-r-6)

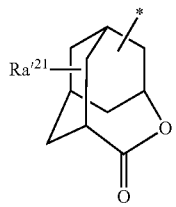
(a2-r-7)

In the formula, Ra$^{\prime 21}$'s each independently represent a hydrogen atom, an alkyl group, an alkoxy group, a halogen atom, a halogenated alkyl group, a hydroxyl group, —COOR$^{\prime\prime}$, —OC(=O) R$^{\prime\prime}$, a hydroxyalkyl group, or a cyano group; R$^{\prime\prime}$ is a hydrogen atom, an alkyl group, a lactone-containing cyclic group, a carbonate-containing cyclic group, or a —SO$_2$— containing cyclic group; A$^{\prime\prime}$ is an alkylene group having 1 to 5 carbon atoms, which may have an oxygen atom (—O—) or a sulfur atom (—S—), an oxygen atom, or a sulfur atom; n' is an integer of 0 to 2; and m' is 0 or 1.

In general formulae (a2-r-1) to (a2-r-7), the alkyl group for $Ra'^{21}$ is preferably an alkyl group having 1 to 6 carbon atoms. The alkyl group is preferably a linear or branched alkyl group. Specifically, examples thereof include a methyl group, an ethyl group, a propyl group, an isopropyl group, an n-butyl group, an isobutyl group, a tert-butyl group, a pentyl group, an isopentyl group, a neopentyl group, and a hexyl group. Among them, the methyl group or the ethyl group is preferable, and the methyl group is particularly preferable.

The alkoxy group for $Ra'^{21}$ is preferably an alkoxy group having 1 to 6 carbon atoms.

The alkoxy group is preferably a linear or branched alkoxy group. Specifically, examples thereof include a group in which the alkyl group exemplified as the alkyl group for $Ra'^{21}$ and an oxygen atom (—O—) are linked with each other.

Examples of the halogen atom for $Ra'^{21}$ include a fluorine atom, a chlorine atom, a bromine atom, and an iodine atom, and among them, the fluorine atom is preferable.

Examples of the halogenated alkyl group for $Ra'^{21}$ include a group obtained by substituting at least one hydrogen atom of the alkyl group for $Ra'^{21}$ with a halogen atom. The halogenated alkyl group is preferably a fluorinated alkyl group, and is particularly preferably a perfluoroalkyl group.

In —COOR" and —OC(=O) R" for $Ra'^{21}$, R"'s are a hydrogen atom, an alkyl group, a lactone-containing cyclic group, carbonate-containing cyclic group, or a —SO$_2$— containing cyclic group.

The alkyl group for R" may be a linear, branched, or cyclic alkyl group, and the number of carbon atoms thereof is preferably 1 to 15.

In the case where R" is a linear or branched alkyl group, the number of carbon atoms is preferably 1 to 10, and is further preferably 1 to 5. Particularly, a methyl group or an ethyl group is preferable.

In the case where R" is a cyclic alkyl group, the number of carbon atoms is preferably 3 to 15, is further preferably 4 to 12, and is most preferably 5 to 10. Specifically, examples of the cyclic alkyl group include a group obtained by removing one or more hydrogen atoms from monocycloalkane which may be or may be not substituted with a fluorine atom or a fluorinated alkyl group; and a group obtained by removing one or more hydrogen atoms from polycycloalkane such as bicycloalkane, tricycloalkane, and tetracycloalkane. More specifically, examples of the cyclic alkyl group include a group obtained by removing one or more hydrogen atoms from monocycloalkane such as cyclopentane and cyclohexane; and a group obtained by removing one or more hydrogen atoms from polycycloalkane such as adamantane, norbornane, isobornane, tricyclodecane, and tetracyclododecane.

Examples of the lactone-containing cyclic group for R" include the same groups which are represented by general formulae (a2-r-1) to (a2-r-7).

The carbonate-containing cyclic group for R" is the same as a carbonate-containing cyclic group described below, and specific examples thereof include the same groups which are represented by general formulae (ax3-r-1) to (ax3-r-3).

The —SO$_2$— containing cyclic group for R" is the same as a —SO$_2$— containing cyclic group described below, and specific examples thereof include the same groups which are represented by general formulae (a5-r-1) to (a5-r-4).

The hydroxyalkyl group for $Ra'^{21}$ is preferably a hydroxyalkyl group having 1 to 6 carbon atoms, and specific examples thereof include a group obtained by substituting at least one hydrogen atom of the alkyl group for $Ra'^{21}$ with a hydroxyl group.

In general formulae (a2-r-2), (a2-r-3), and (a2-r-5), the alkylene group having 1 to 5 carbon atoms for A" is preferably a linear or branched alkylene group, and examples thereof include a methylene group, an ethylene group, an n-propylene group, and an isopropylene group. In the case where the alkylene group contains an oxygen atom or a sulfur atom, specific examples thereof include a group in which —O— or —S— is present at a terminal of the alkylene group or between carbon atoms, and examples of the group include —O—CH$_2$—, —CH$_2$—O—CH$_2$—, —S—CH$_2$—, and —CH$_2$—S—CH$_2$—. The A" is preferably an alkylene group having 1 to 5 carbon atoms or —O—, is further preferably an alkylene group having 1 to 5 carbon atoms, and is most preferably a methylene group.

Specific examples of the groups represented by general formulae (a2-r-1) to (a2-r-7) are described as follows.

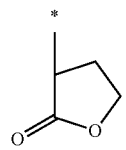
(r-lc-1-1)

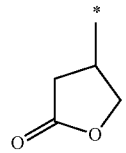
(r-lc-1-2)

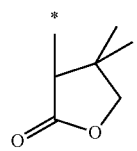
(r-lc-1-3)

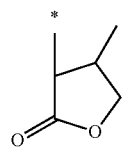
(r-lc-1-4)

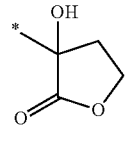
(r-lc-1-5)

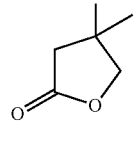
(r-lc-1-6)

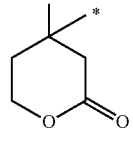
(r-lc-1-7)

-continued
(r-lc-2-1)
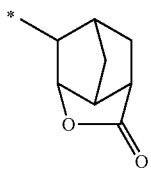
(r-lc-2-2)
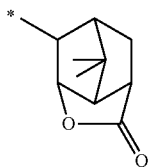
(r-lc-2-3)
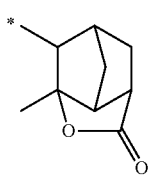
(r-lc-2-4)
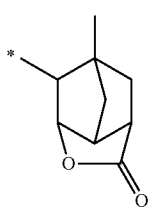
(r-lc-2-5)
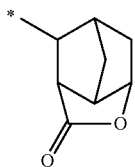
(r-lc-2-6)
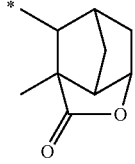
(r-lc-2-7)
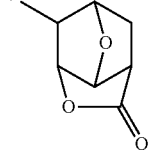
(r-lc-2-8)
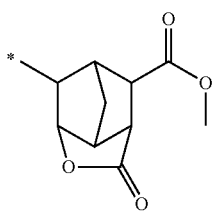
-continued
(r-lc-2-9)
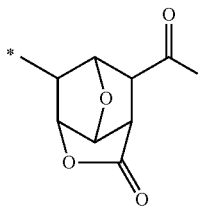
(r-lc-2-10)
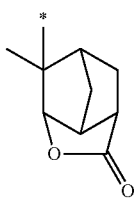
(r-lc-2-11)
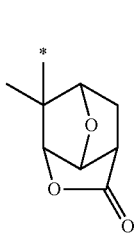
(r-lc-2-12)
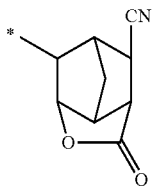
(r-lc-2-13)
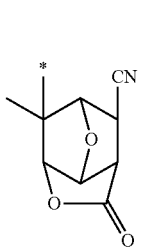
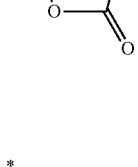
(r-lc-2-14)
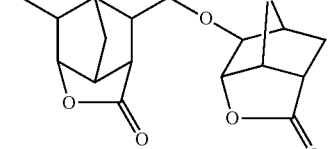
(r-lc-2-15)
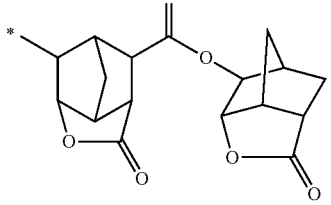

(r-lc-2-16)
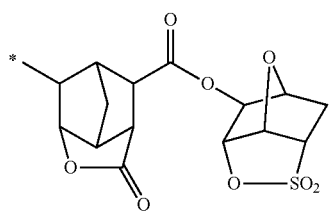
(r-lc-2-17)
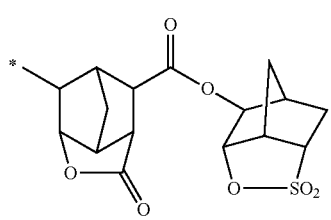
(r-lc-2-18)
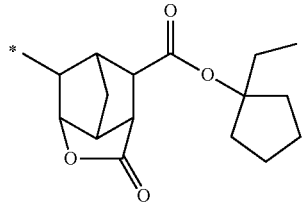
(r-lc-3-1)
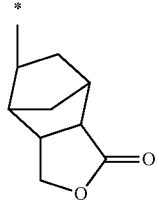
(r-lc-3-2)
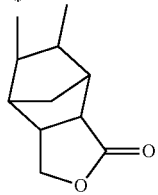
(r-lc-3-3)
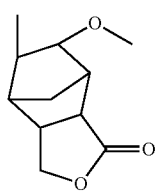
(r-lc-3-4)
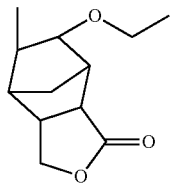
(r-lc-3-5)
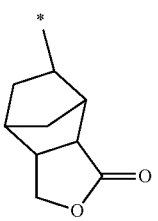
(r-lc-4-1)
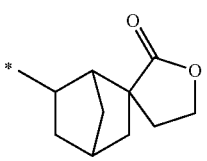
(r-lc-4-2)
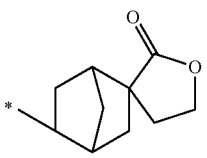
(r-lc-4-3)
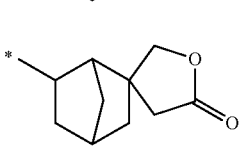
(r-lc-4-4)
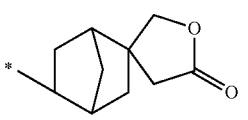
(r-lc-4-5)
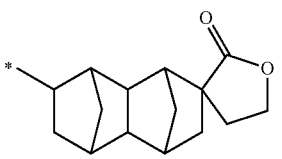
(r-lc-4-6)
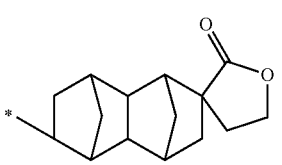
(r-lc-4-7)
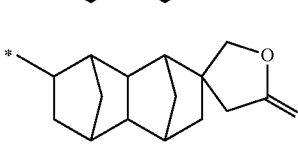
(r-lc-4-8)
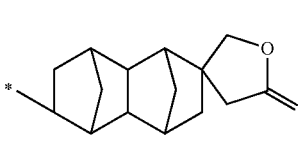
(r-lc-4-9)
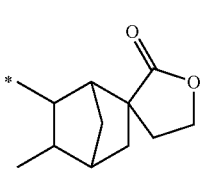

-continued

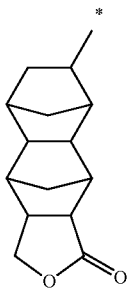
(r-lc-5-1)

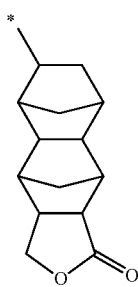
(r-lc-5-2)

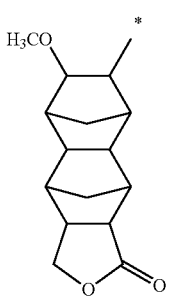
(r-lc-5-3)

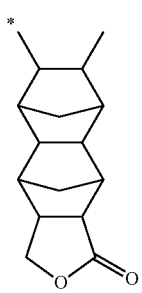
(r-lc-5-4)

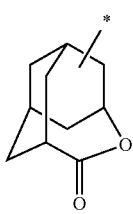
(r-lc-6-1)

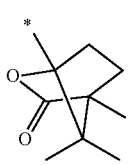
(r-lc-7-1)

The "—$SO_2$— containing cyclic group" means a cyclic group which contains a ring containing —$SO_2$— in the cyclic skeleton, and specifically, the sulfur atom (S) in —$SO_2$— is a cyclic group which forms a portion of the cyclic skeleton of the cyclic group. When the ring containing —$SO_2$— in the cyclic skeleton is counted as the first ring, if there is only the ring, the cyclic group is referred to as a monocyclic group, and if there are other ring structures in addition to the ring, the cyclic group is referred to as a polycyclic group regardless of its structure. The —$SO_2$-containing cyclic group may be a monocyclic group or may be a polycyclic group.

The —$SO_2$— containing cyclic group is particularly preferably a cyclic group containing —O—$SO_2$— in the cyclic skeleton, that is, —O—S— in —O—$SO_2$— is preferably a cyclic group containing a sultone ring which forms a portion of the cyclic skeleton.

More specifically, examples of the —$SO_2$— containing cyclic group include the same groups which are represented by general formulae (a5-r-1) to (a5-r-4).

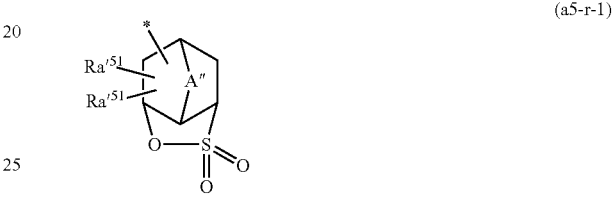
(a5-r-1)

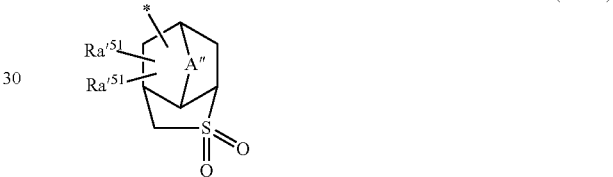
(a5-r-2)

(a5-r-3)

(a5-r-4)

In the formula, $Ra'^{51}$'s each independently represent a hydrogen atom, an alkyl group, an alkoxy group, a halogen atom, a halogenated alkyl group, a hydroxyl group, —COOR", —OC(=O) R", a hydroxyalkyl group, or a cyano group; R" is a hydrogen atom, an alkyl group, a lactone-containing cyclic group, a carbonate-containing cyclic group, or a —$SO_2$— containing cyclic group; A" is an alkylene group having 1 to 5 carbon atoms, which may have an oxygen atom or a sulfur atom, an oxygen atom, or a sulfur atom; and n' is an integer of 0 to 2.

In general formulae (a5-r-1) and (a5-r-2), A" is the same as A" in general formulae (a2-r-2), (a2-r-3), and (a2-r-5).

An alkyl group, an alkoxy group, a halogen atom, a halogenated alkyl group, —COOR", —OC(=O)R", and a hydroxyalkyl group for $Ra'^{51}$ are the same as those exemplified in the description for $Ra'^{21}$ in general formulae (a2-r-1) to (a2-r-7).

Specific examples of the groups represented by general formulae (a5-r-1) to (a5-r-4) are described as follows. "Ac" in the formulae represents an acetyl group.

(r-s1-1-1) 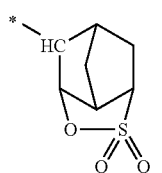
(r-s1-1-2) 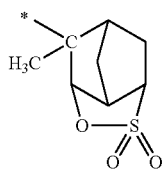
(r-s1-1-3) 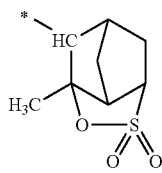
(r-s1-1-4) 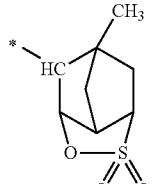
(r-s1-1-5) 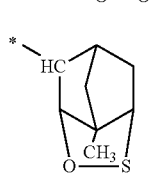
(r-s1-1-6) 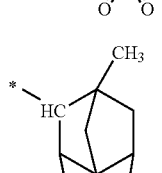
(r-s1-1-7) 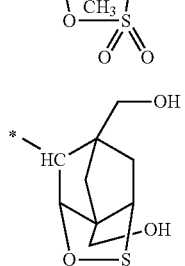
(r-s1-1-8) 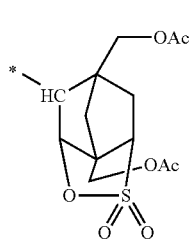
-continued
(r-s1-1-9) 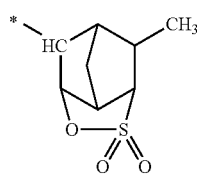
(r-s1-1-10) 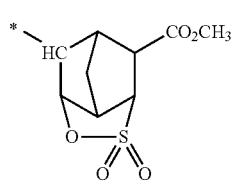
(r-s1-1-11) 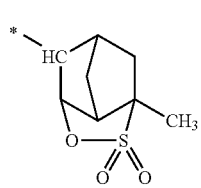
(r-s1-1-12) 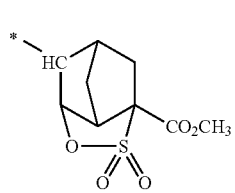
(r-s1-1-13) 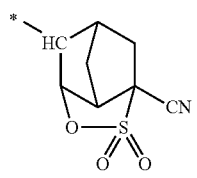
(r-s1-1-14) 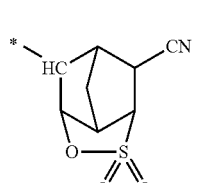
(r-s1-1-15) 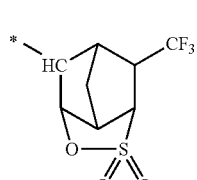
(r-s1-1-16) 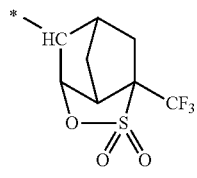

(r-s1-1-17)
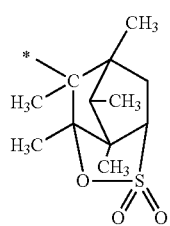
(r-s1-1-18)
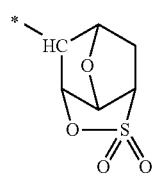
(r-s1-1-19)
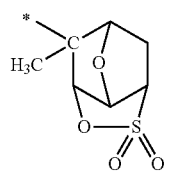
(r-s1-1-20)
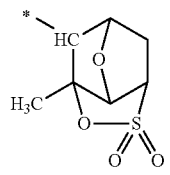
(r-s1-1-21)
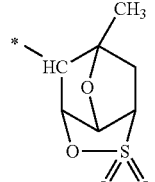
(r-s1-1-22)
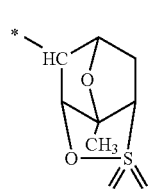
(r-s1-1-23)
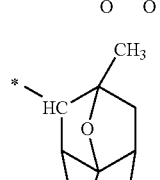
(r-s1-1-24)
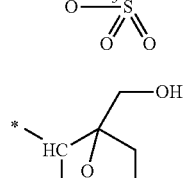
(r-s1-1-25)
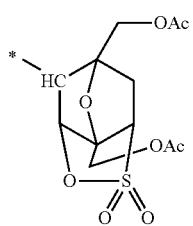
(r-s1-1-26)
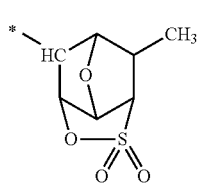
(r-s1-1-27)
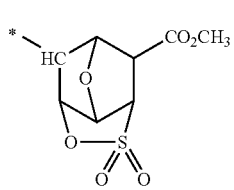
(r-s1-1-28)
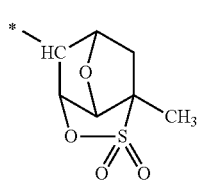
(r-s1-1-29)
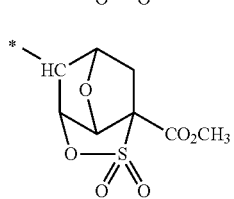
(r-s1-1-30)
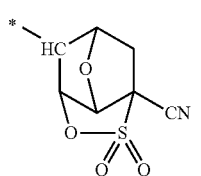
(r-s1-1-31)
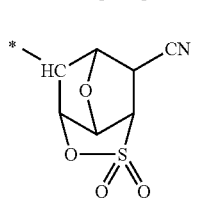
(r-s1-1-32)
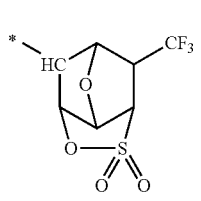

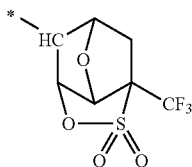
(r-s1-1-33)

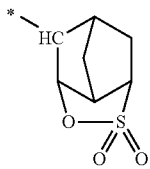
(r-s1-2-1)

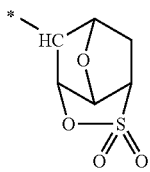
(r-s1-2-2)

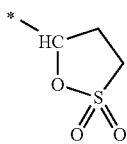
(r-s1-3-1)

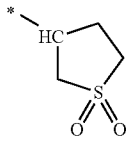
(r-s1-4-1)

The "carbonate-containing cyclic group" means a cyclic group containing a ring (carbonate ring) including —O—C(=O)—O— in the cyclic skeleton. When the carbonate ring is counted as the first ring, if there is only the carbonate ring, the cyclic group is referred to as a monocyclic group, and if there are other ring structures in addition to the carbonate ring, the cyclic group is referred to as a polycyclic group regardless of its structure. The carbonate-containing cyclic group may be a monocyclic group, or may be a polycyclic group.

The carbonate ring-containing cyclic group is not particularly limited, and any carbonate ring-containing cyclic group can be used. Specific examples thereof include the same groups which are represented by general formulae (ax3-r-1) to (ax3-r-3).

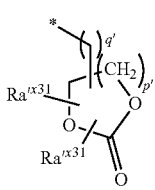
(ax3-r-1)

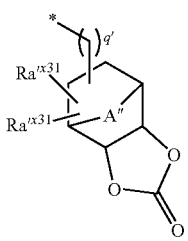
(ax3-r-2)

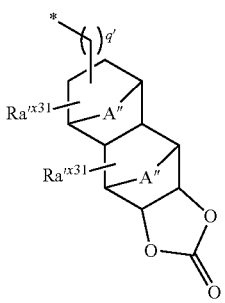
(ax3-r-3)

In the formulae, $Ra'^{x31}$'s each independently represent a hydrogen atom, an alkyl group, an alkoxy group, a halogen atom, a halogenated alkyl group, a hydroxyl group, —COOR", —OC(=O) R", a hydroxyalkyl group, or a cyano group; R" is a hydrogen atom, an alkyl group, a lactone-containing cyclic group, a carbonate-containing cyclic group, or a —SO$_2$— containing cyclic group; A" is an alkylene group having 1 to 5 carbon atoms, which may have an oxygen atom or a sulfur atom, an oxygen atom, or a sulfur atom; p' is an integer of 0 to 3; and q' is 0 or 1.

In general formulae (ax3-r-2) and (ax3-r-3), A" is the same as A" in general formulae (a2-r-2), (a2-r-3), and (a2-r-5).

An alkyl group, an alkoxy group, a halogen atom, a halogenated alkyl group, —COOR", —OC(=O)R", and a hydroxyalkyl group for $Ra'^{31}$ are the same as those exemplified in the description for $Ra'^{21}$ in general formulae (a2-r-1) to (a2-r-7).

Specific examples of the groups represented by general formulae (ax3-r-1) to (ax3-r-3) are described as follows.

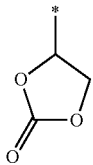
(r-cr-1-1)

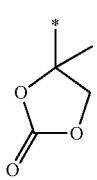
(r-cr-1-2)

(r-cr-1-3)
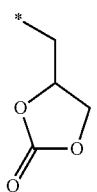
(r-cr-1-4)
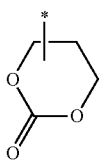
(r-cr-1-5)
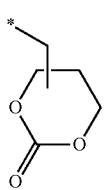
(r-cr-1-6)
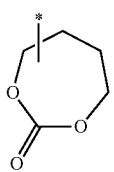
(r-cr-1-7)
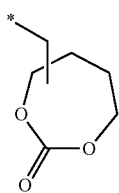
(r-cr-2-1)
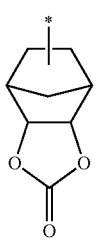
(r-cr-2-2)
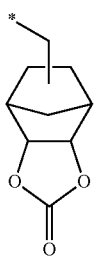
(r-cr-2-3)
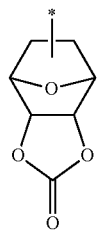
(r-cr-2-4)
(r-cr-3-1)
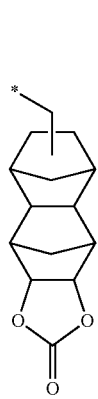
(r-cr-3-2)
(r-cr-3-3)

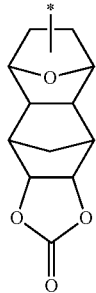

(r-cr-3-4)

(r-cr-3-5)

Among the structural units (a2), it is preferably a structural unit derived from acrylic ester which may be obtained by substituting a hydrogen atom bonded to an α-position carbon atom with a substituent.

The structural unit (a2) is preferably a structural unit represented by general formula (a2-1).

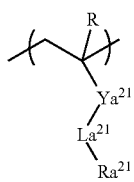

(a2-1)

In the formula, R is a hydrogen atom, an alkyl group having 1 to 5 carbon atoms, or a halogenated alkyl group having 1 to 5 carbon atoms. $Ya^{21}$ is a single bond or a divalent linking group. $La^{21}$ is —O—, —COO—, —CON(R')—, —OCO—, —CONHCO—, or —CONHCS—, and R' represents a hydrogen atom or a methyl group. Here, in the case where $La^{21}$ is —O—, $Ya^{21}$ is not —CO—. $Ra^{21}$ is a lactone-containing cyclic group, a carbonate-containing cyclic group, or a —SO$_2$— containing cyclic group.

In general formula (a2-1), R is the same as described above. The divalent linking group for $Ya^{21}$ is not particularly limited, and preferred examples thereof include a divalent hydrocarbon group which may have a substituent and a divalent linking group containing a heteroatom.

Divalent Hydrocarbon Group which May have a Substituent:

In the case where $Ya^{21}$ is a divalent hydrocarbon group which may have a substituent, the hydrocarbon group may be an aliphatic hydrocarbon group or an aromatic hydrocarbon group.

Aliphatic Hydrocarbon Group for $Ya^{21}$

The aliphatic hydrocarbon group means a hydrocarbon group having no aromaticity. The aliphatic hydrocarbon group may be saturated or unsaturated, and is preferably saturated in general.

Examples of the aliphatic hydrocarbon group include a linear or branched aliphatic hydrocarbon group, or an aliphatic hydrocarbon group containing a ring in the structure.

Linear or Branched Aliphatic Hydrocarbon Group

The number of carbon atoms of the linear aliphatic hydrocarbon group is preferably 1 to 10, is further preferably 1 to 6, is further still preferably 1 to 4, and is most preferably 1 to 3.

As a linear aliphatic hydrocarbon group, a linear alkylene group is preferable, and specific examples include a methylene group [—CH$_2$—], an ethylene group [—(CH$_2$)$_2$—], a trimethylene group [—(CH$_2$)$_3$—], a tetramethylene group [—(CH$_2$)$_4$—], and a pentamethylene group [—(CH$_2$)$_5$—].

The number of carbon atoms of the branched aliphatic hydrocarbon group is preferably 3 to 10, is further preferably 3 to 6, is still further preferably 3 or 4, and is most preferably 3.

As a branched aliphatic hydrocarbon group, a branched alkylene group is preferable, and specific examples thereof include an alkyl alkylene group such as an alkyl methylene group such as —CH(CH$_3$)—, —CH(CH$_2$CH$_3$)—, —C(CH$_3$)$_2$—, —C(CH$_3$) (CH$_2$CH$_3$)—, —C(CH$_3$) (CH$_2$CH$_2$CH$_3$)—, and —C(CH$_2$CH$_3$)$_2$—; an alkyl ethylene group such as —CH(CH$_3$) CH$_2$—, —CH(CH$_3$) CH(CH$_3$)—, (CH$_3$)$_2$CH$_2$—, —CH(CH$_2$CH$_3$) CH$_2$—, —C(CH$_2$CH$_3$)$_2$—CH$_2$—; an alkyl trimethylene group such as —CH(CH$_3$) CH$_2$CH$_2$— and —CH$_2$CH(CH$_3$) CH$_2$—; and an alkyl tetramethylene group such as —CH(CH$_3$) CH$_2$CH$_2$CH$_2$— and —CH$_2$CH(CH$_3$) CH$_2$CH$_2$—. As an alkyl group in an alkyl alkylene group, a linear alkyl group having 1 to 5 carbon atoms is preferable.

The linear or branched aliphatic hydrocarbon group may or may not have a substituent. Examples of the substituent include a fluorine atom, a fluorinated alkyl group having 1 to 5 carbon atoms which is substituted with a fluorine atom, and a carbonyl group.

Aliphatic Hydrocarbon Group Containing Ring in Structure

Examples of the aliphatic hydrocarbon group containing a ring in the structure include a cyclic aliphatic hydrocarbon group (a group obtained by removing two hydrogen atoms from an aliphatic hydrocarbon ring) which may contain a substituent containing a heteroatom in the ring structure, a group in which the cyclic aliphatic hydrocarbon group is bonded to a terminal of the linear or branched aliphatic hydrocarbon group, and a group in which the cyclic aliphatic hydrocarbon group is present in the middle of the linear or branched aliphatic hydrocarbon group. Examples of the linear or branched cyclic aliphatic hydrocarbon group include the same groups as described above.

The number of carbon atoms of the cyclic aliphatic hydrocarbon group is preferably 3 to 20, and is further preferably 3 to 12.

The cyclic aliphatic hydrocarbon group may be a polycyclic group, or may be a monocyclic group. As the monocyclic alicyclic hydrocarbon group, a group obtained by removing two hydrogen atoms from a monocycloalkane is preferable. The number of carbon atoms of the monocycloalkane is preferably 3 to 6. Specifically, examples thereof include cyclopentane and cyclohexane. As the polycyclic alicyclic hydrocarbon group, a group obtained by removing two hydrogen atoms from polycycloalkane is preferable, and the number of carbon atoms of polycycloalkane is preferably 7 to 12. Specifically, examples thereof include adamantane, norbornane, isobornane, tricyclodecane, and tetracyclododecane.

The cyclic aliphatic hydrocarbon group may or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and is most preferably a methyl group, an ethyl group, a propyl group, an n-butyl group, and a tert-butyl group.

The alkoxy group as the substituent is preferably an alkoxy group having 1 to 5 carbon atoms, is further preferably a methoxy group, an ethoxy group, an n-propoxy group, an iso-propoxy group, an n-butoxy group, and a tert-butoxy group, and is most preferably a methoxy group, and an ethoxy group.

Examples of the halogen atom as the substituent include a fluorine atom, a chlorine atom, a bromine atom, and an iodine atom, and the fluorine atom is preferable.

Examples of the halogenated alkyl group as the substituent include a group obtained by substituting at least one hydrogen atom of an alkyl group with a halogen atom.

The cyclic aliphatic hydrocarbon group may be substituted with a substituent in which a portion of the carbon atoms for constituting the ring structure contains a heteroatom. The substituent containing the heteroatom is preferably —O—, —C(=O)—O—, —S—, —S(=O)$_2$—, and —S(=O)$_2$—O—.

Aromatic Hydrocarbon Group for Ya$^{21}$

The aromatic hydrocarbon group is a hydrocarbon group having at least one aromatic ring.

The aromatic ring is not particularly limited as long as it is a cyclic conjugated system having (4n+2) π-electrons, and it may be monocyclic or polycyclic. The number of the carbon atoms of the aromatic ring is preferably 5 to 30, is further preferably 5 to 20, is still further preferably 6 to 15, and is particularly preferably 6 to 12. In this regard, the number of the carbon atoms does not include the number of the carbon atoms in the substituent. Specific examples of the aromatic ring include an aromatic hydrocarbon ring such as benzene, naphthalene, anthracene, and phenanthrene; and aromatic heterocycle in which a portion of the carbon atoms which constitute the aromatic hydrocarbon ring is substituted with a heteroatom. Examples of the heteroatom in the aromatic heterocycle include an oxygen atom, a sulfur atom, and a nitrogen atom.

Specific examples of the aromatic heterocycle include a pyridine ring and a thiophene ring.

Specific examples of the aromatic hydrocarbon group include a group (an arylene group or a heteroarylene group) obtained by removing two hydrogen atoms from the aromatic hydrocarbon ring or the aromatic heterocycle; a group obtained by removing two hydrogen atoms from an aromatic compound (for example, biphenyl and fluorene) containing two or more aromatic rings; and a group (for example, a group obtained by further removing one hydrogen atom from the aryl group in the aryl alkyl group such as a benzyl group, a phenethyl group, a 1-naphthyl methyl group, a 2-naphthyl methyl group, a 1-naphthyl ethyl group, and a 2-naphthyl ethyl group) in which one hydrogen atom of the group (an aryl group or a heteroaryl group) obtained by removing one hydrogen atom from the aromatic hydrocarbon ring or the aromatic heterocycle is substituted with an alkylene group. The number of carbon atoms of the alkylene group which is bonded to the aryl group or the heteroaryl group is preferably 1 to 4, is further preferably 1 to 2, and particularly preferably 1.

In the aromatic hydrocarbon group, the hydrogen atom contained in the aromatic hydrocarbon group may be substituted with a substituent. For example, a hydrogen atom bonded to the aromatic ring in the aromatic hydrocarbon group may be substituted with a substituent. Examples of the substituent include an alkyl group, an alkoxy group, a halogen atom, a halogenated alkyl group, and a hydroxyl group.

The alkyl group as the substituent is preferably an alkyl group having 1 to 5 carbon atoms, and is most preferably a methyl group, an ethyl group, a propyl group, an n-butyl group, and a tert-butyl group.

Examples of an alkoxy group, a halogen atom, and a halogenated alkyl group as the substituent include those exemplified as a substituent which substitutes a hydrogen atom contained in the cyclic aliphatic hydrocarbon group.

Divalent Linking Group Containing a Heteroatom:

In the case where Ya$^{21}$ is a divalent linking group containing heteroatom, preferred examples of the divalent linking group containing a heteroatom include —O—, —C(=O)—O—, —C(=O)—, —O—C(=O)—O—, —C(=O)—NH—, —NH—, —NH—C(=NH)— (H may be substituted with a substituent such as an alkyl group and an acyl group), —S—, —S(=O)$_2$—, —S(=O)$_2$—O—, and a group represented by general formulae: —Y$^{21}$—O—Y$^{22}$—, —Y$^{21}$—O—, —Y$^{21}$—C(=O)—O—, —C(=O)—O—Y$^{21}$—, [Y$^{21}$—C(=O)—O]$_{m''}$—Y$^{22}$—, —Y$^{21}$—O—C(=O)—Y$^{22}$— and —Y$^{21}$—S(=O)$_2$—O—U$^{22}$— (In the formulae, Y$^{21}$ and Y$^{22}$ each independently represent a divalent hydrocarbon group which may have a substituent, 0 represents an oxygen atom, and m" represents an integer of 0 to 3).

In the case where the divalent linking group containing the heteroatom is —C(=O)—NH—, —C(=O)—NH—C(=O)—, —NH—, or —NH—C(=NH)—, H may be substituted with a substituent such as an alkyl group and an acyl group. The substituent (an alkyl group, an acyl group, or the like) preferably has 1 to 10 carbon atoms, further preferably has 1 to 8 carbon atoms, and particularly preferably has 1 to 5 carbon atoms.

In general formulae: —Y$^{21}$—O—Y$^{22}$—, —Y$^{21}$—O—, —Y$^{21}$—C(=O)—O—, —C(=O)—O—Y$^{21}$—, [Y$^{21}$—C(=O)—O]$_{m''}$—Y$^{22}$—, —Y$^{21}$—O—C(=O)—Y$^{22}$—, and —Y$^{21}$—S(=O)$_2$—O—Y$^{22}$—, Y$^{21}$ and Y$^{22}$ each independently represent a divalent hydrocarbon group which may have a substituent. Examples of the divalent hydrocarbon group include the same group as that (divalent hydrocarbon group which may have a substituent) exemplified as the divalent linking group.

Y$^{21}$ is preferably a linear aliphatic hydrocarbon group, is further preferably a linear alkylene group, is still further preferably a linear alkylene group having 1 to 5 carbon atoms, and is particularly preferably a methylene group or an ethylene group.

Y$^{22}$ is preferably a linear or branched aliphatic hydrocarbon group, and is further preferably a methylene group, an ethylene group, or an alkyl methylene group. An alkyl group in the alkyl methylene group is preferably a linear alkyl group having 1 to 5 carbon atoms, is further preferably a linear alkyl group having 1 to 3 carbon atoms, and is most preferably a methyl group.

In the group represented by general formula —[Y$^{21}$—C(=O)—O]$_{m''}$, m" is an integer of 0 to 3, is preferably an integer of 0 to 2, is further preferably 0 or 1, and is particularly preferably 1. That is, as a group represented by general formula —[Y$^{21}$—C(=O)—O]$_{m''}$—Y$^{22}$—, a group represented by general formula —Y$^{21}$—C(=O)—O—Y$^{22}$— is particularly preferable. Among them, a group represented by general formula —(CH$_2$)$_a$'-C(=O)—O—

$(CH_2)_{b'}$— is preferable. In the formula, a' is an integer of 1 to 10, is preferably an integer of 1 to 8, is further preferably an integer of 1 to 5, is still further preferably 1 or 2, and is most preferably 1. b' is an integer of 1 to 10, is preferably an integer of 1 to 8, is further preferably an integer of 1 to 5, is still further preferably 1 or 2, and is most preferably 1.

$Ya^{21}$ is preferably a single bond, an ester bond [—C(=O)—O—], an ether bond (—O—), a linear or branched alkylene group, or a combination thereof.

In general formula (a2-1), $Ra^{21}$ is a lactone-containing cyclic group, a —$SO_2$— containing cyclic group, or a carbonate-containing cyclic group.

Preferred examples of the lactone-containing cyclic group, the —$SO_2$— containing cyclic group, and the carbonate-containing cyclic group for $Ra^{21}$ include groups represented by general formulae (a2-r-1) to (a2-r-7), groups represented by general formulae (a5-r-1) to (a5-r-4), and groups represented by general formulae (ax3-r-1) to (ax3-r-3).

Among them, the lactone-containing cyclic group or the —$SO_2$-containing cyclic group are preferable, the group represented by general formula (a2-r-1), (a2-r-2), (a2-r-6), or (a5-r-1) is further preferable. Specifically, any one of the groups represented by each of chemical formulae (r-lc-1-1) to (r-lc-1-7), (r-lc-2-1) to (r-lc-2-18), (r-lc-6-1), (r-sl-1-1), and (r-sl-1-18) is further preferable.

The structural unit (a2) in the (A1) component may be used alone, or two or more kinds thereof may be used in combination.

In the case where the (A1) component contains the structural unit (a2), the ratio of the structural unit (a2) is preferably 1 to 80 mol %, is further preferably 10 to 70 mol %, is still further preferably 10 to 65 mol %, and is particularly preferably 10 to 60 mol %, with respect to the total (100 mol %) of the entire structural units for constituting the (A1) component.

When the ratio of the structural unit (a2) is set to be equal to or greater than the preferred lower limit value, it is possible to obtain sufficient effects by containing the structural unit (a2); on the other hand, when the ratio of the structural unit (a2) is set to be equal to or lower than the preferred upper limit value, it is possible to make balance with other structural units, and thus various lithography properties and the pattern shape are improved.

Structural Unit (a3)

The structural unit (a3) is a structural unit containing a polar group-containing aliphatic hydrocarbon group (here, except for structural units corresponding to the structural units (a1) and (a2)).

It is considered that when the (A1) component has a structural unit (a3), the hydrophilicity of the (A1) component is enhanced, which contributes to enhancement of the resolution.

Examples of the polar group include a hydroxyalkyl group in which a portion of the hydrogen atom of a hydroxyl group, a cyano group, a carboxy group, and an alkyl group is substituted with a fluorine atom, and among them, the hydroxyl group is particularly preferable.

Examples of the aliphatic hydrocarbon group include a linear or branched hydrocarbon group (preferably an alkylene group) having 1 to 10 carbon atoms, and a cyclic aliphatic hydrocarbon group (a cyclic group). The cyclic group may be a monocyclic group, or may be a polycyclic group, for example, in resins for resist compositions for ArF excimer lasers, the cyclic group can be appropriately selected from the resins which have been proposed many times. The cyclic group is preferably a polycyclic group, and the number of the carbon atoms is further preferably 7 to 30.

Among them, a structural unit derived from acrylic ester containing an aliphatic polycyclic group including a hydroxyalkyl group in which a portion of the hydrogen atoms of a hydroxyl group, a cyano group, a carboxy group, or an alkyl group is substituted with a fluorine atom is further preferable. Examples of the polycyclic group include a group obtained by removing two or more hydrogen atoms from bicycloalkane, tricycloalkane, and tetracycloalkane. Specific examples thereof include a group obtained by removing two or more hydrogen atoms from polycycloalkane such as adamantane, norbornane, isobornane, tricyclodecane, and tetracyclododecane. Among the polycyclic groups, a group obtained by removing two or more hydrogen atoms from adamantane, a group obtained by removing two or more hydrogen atoms from norbornane, and a group obtained by removing two or more hydrogen atoms from tetracyclododecane are preferred in terms of the industrial availability.

The structural unit (a3) is not particularly limited as long as it contains a polar group-containing aliphatic hydrocarbon group, and any structural unit can be used.

The structural unit (a3) is a structural unit derived from acrylic ester which may be obtained by substituting a hydrogen atom bonded to an α-position carbon atom with a substituent, and a structural unit including a polar group-containing aliphatic hydrocarbon group is preferable.

When the hydrocarbon group in the polar group-containing aliphatic hydrocarbon group is a linear or branched hydrocarbon group having 1 to 10 carbon atoms, the structural unit (a3) is preferably a structural unit derived from hydroxyethyl ester of acrylic acid, and when the hydrocarbon group is a polycyclic group, the structural unit (a3) is preferably a structural unit represented by general formula (a3-1), a structural unit represented by general formula (a3-2), and a structural unit represented by general formula (a3-3).

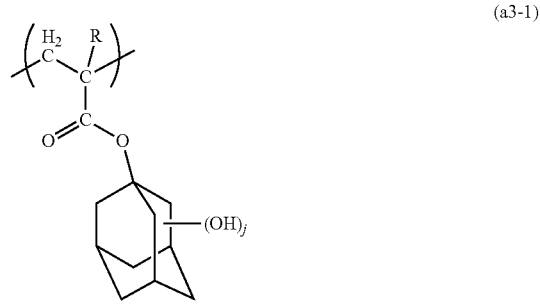

(a3-1)

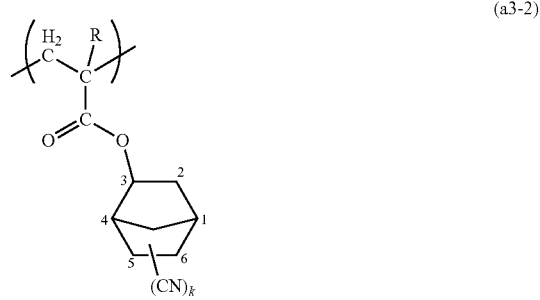

(a3-2)

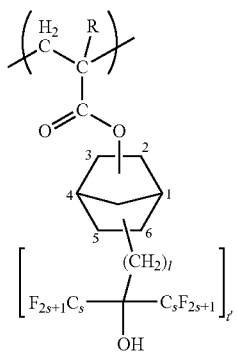

(a3-3)

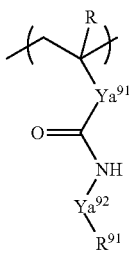

(a9-1)

In the formulae, R is the same as described above, j is an integer of 1 to 3, k is an integer of 1 to 3, t' is an integer of 1 to 3, l is an integer of 1 to 5, and s is an integer of 1 to 3.

In general formula (a3-1), j is preferably 1 or 2, and is further preferably 1. In a case where j is 2, a hydroxyl group is preferably bonded to 3-position and 5-position of an adamantyl group. In a case where j is 1, a hydroxyl group is preferably bonded to 3-position of an adamantyl group.

j is preferably 1, and a hydroxyl group is particularly preferably bonded to 3-position of an adamantyl group.

In general formula (a3-2), k is preferably 1. A cyano group is preferably bonded to a 5-position or 6-position of a norbornyl group.

In general formula (a3-3), t' is preferably 1. l is preferably 1. s is preferably 1. In these, a 2-norbornyl group or a 3-norbornyl group is preferably bonded to the terminal of a carboxy group of an acrylic acid. The fluorinated alkyl alcohol is preferably bonded to a 5-position or 6-position of a norbornyl group.

The structural unit (a3) in the (A1) component may be used alone, or two or more kinds of thereof may be used in combination.

In a case where the (A1) component includes a structural unit (a3), the ratio of the structural unit (a3) is preferably 5 to 50 mol %, is further preferably 5 to 40 mol %, and is still further preferably 5 to 25 mol %, with respect to the total (100 mol %) of the entire structural units for constituting the (A1) component.

When the ratio of the structural unit (a3) is set to be equal to or greater than the lower limit value, it is possible to obtain sufficient effects by containing the structural unit (a3); on the other hand, when the ratio of the structural unit (a3) is set to be equal to or lower than the upper limit value, it is easy to make balance with other structural units.

Other Structural Units

The (A1) component may have other structural units in addition to the structural unit (a10), the structural unit (a1), the structural unit (a2), and the structural unit (a3).

Examples of other structural units include a structural unit derived from the styrene, a structural unit derived from the styrene derivative (except for a structural unit corresponding to the structural unit (a10)), a structural unit (a9) represented by general formula (a9-1), and a structural unit containing a non-acid-dissociative aliphatic cyclic group.

Structural Unit (a9)

The structural unit (a9) is a structural unit represented by general formula (a9-1).

In the formula, R is a hydrogen atom, an alkyl group having 1 to 5 carbon atoms, or a halogenated alkyl group having 1 to 5 carbon atoms. $Ya^{91}$ is a single bond or a divalent linking group. $Ya^{92}$ is a divalent linking group. $R^{91}$ is a hydrocarbon group which may have a substituent.

In general formula (a9-1), R is the same as described above.

R is preferably a hydrogen atom, an alkyl group having 1 to 5 carbon atoms, or a fluorinated alkyl group having 1 to 5 carbon atoms, and a hydrogen atom or a methyl group is particularly preferable in terms of industrial availability.

In general formula (a9-1), examples of the divalent linking group for $Ya^{91}$ include the same divalent linking group as that for $Ya^{21}$ in general formula (a2-1). $Ya^{91}$ is preferably a single bond.

In general formula (a9-1), examples of the divalent linking group for $Ya^{92}$ include the same divalent linking group as that for $Ya^{21}$ in general formula (a2-1).

With respect to the divalent linking group for $Ya^{92}$, as a divalent hydrocarbon group which may have a substituent, a linear or branched aliphatic hydrocarbon group is preferable.

The number of carbon atoms of the linear aliphatic hydrocarbon group is preferably 1 to 10, is further preferably 1 to 6, is further still preferably 1 to 4, and is most preferably 1 to 3. As the linear aliphatic hydrocarbon group, the linear alkylene group is preferable, and specifically, examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The number of carbon atoms of the branched aliphatic hydrocarbon group is preferably 3 to 10, is further preferably 3 to 6, is still further preferably 3 or 4, and is most preferably 3. As the branched aliphatic hydrocarbon group, a branched chain alkylene group is preferable, and specifically, examples thereof include an alkyl alkylene group such as an alkyl methylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an alkyl ethylene group such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; an alkyl trimethylene group such as —$CH(CH_3)CH_2CH_2$—, and —$CH_2CH(CH_3)CH_2$—; and an alkyl tetramethylene group such as —$CH(CH_3)CH_2CH_2CH_2$— and —$CH_2CH(CH_3)CH_2CH_2$—. As an alkyl group in the alkyl alkylene group, a linear alkyl group having 1 to 5 carbon atoms is preferable.

In addition, with respect to the divalent linking group for $Ya^{92}$, examples of the divalent linking group which may have a heteroatom include —O—, —C(=O)—O—, —C(=O)—, —O—C(=O)—O—, —C(=O)—NH—, —NH—, —NH—C(=NH)— (H may be substituted with a substituent such as an alkyl group and an acyl group), —S—, —S(=O)$_2$—, —S(=O)$_2$—O—, —C(=S)—, and a group represented by general formula —Y$^{21}$—O—Y$^{22}$—, —Y$^{21}$—O—, —Y$^{21}$—C(=O)—O—, —C(=O)—O—Y$^{21}$, [Y$^{21}$—C(=O)—O]$_{m'}$—Y$^{22}$— or —Y$^{21}$—O—C—(=O)—Y$^{22}$— (where Y$^{21}$ and Y$^{22}$ each independently represent a divalent hydrocarbon group which may a substituent, O is an oxygen atom, and m' is an integer of 0 to 3). Among them, —C(=O)— and —C(=S)— are preferable.

In general formula (a9-1), examples of the hydrocarbon group for R$^{91}$ include an alkyl group, a monovalent alicyclic hydrocarbon group, an aryl group, and an aralkyl group.

The number of carbon atoms of the alkyl group for R$^{91}$ is preferably 1 to 8, is further preferably 1 to 6, and is further still preferably 1 to 4, and the alkyl group may be a linear or branched group. Specifically, preferred examples thereof include a methyl group, an ethyl group, a propyl group, a butyl group, a hexyl group, and an octyl group.

The number of carbon atoms of the monovalent alicyclic hydrocarbon group for R$^{91}$ is preferably 3 to 20, and is further preferably 3 to 12, and the monovalent alicyclic hydrocarbon group may be polycyclic group or a monocyclic group. The monocyclic alicyclic hydrocarbon group is preferably a group obtained by removing one or more hydrogen atoms from monocycloalkane. The number of carbon atoms of the monocycloalkane is preferably 3 to 6, and specifically, is preferably cyclobutane, cyclopentane, cyclohexane, or the like. The polycyclic alicyclic hydrocarbon group is preferably a group obtained by removing one or more hydrogen atoms from polycycloalkane, and the number of carbon atoms of the polycycloalkane is preferably 7 to 12. Specifically, examples thereof include adamantane, norbornane, isobornane, tricyclodecane, and tetracyclododecane.

The number of carbon atoms of the aryl group for R$^{91}$ is preferably 6 to 18, and is further preferably 6 to 10, and specifically, a phenyl group is particularly preferable.

As the aralkyl group for R$^{91}$, an aralkyl group in which an alkylene group having 1 to 8 carbon atoms and "the aryl group for R$^{91}$" are bonded to each other is preferable, an aralkyl group in which an alkylene group having 1 to 6 carbon atoms and "the aryl group for R$^{91}$" are bonded to each other is further preferable, and an aralkyl group in which an alkylene group having 1 to 4 carbon atoms and "the aryl group for R$^{91}$" are bonded to each other is particularly preferable.

Regarding the hydrocarbon group for R$^{91}$, at least one hydrogen atom of the hydrocarbon group are preferably substituted with a fluorine atom, 30% to 100% of the hydrogen atoms contained in the hydrocarbon group is preferably substituted with a fluorine atom. Among them, a perfluoroalkyl group in which all of the hydrogen atoms of the alkyl group are substituted with a fluorine atom is particularly preferable.

The hydrocarbon group for R$^{91}$ may have a substituent. Examples of the substituent include a halogen atom, an oxo group (=O), a hydroxyl group (—OH), an amino group (—NH$_2$), and —SO$_2$—NH$_2$. In addition, a portion of a carbon atom forming a hydrocarbon group may be substituted with a substituent containing a heteroatom. Examples of the substituent containing the heteroatom include —O—, —NH—, —N=, —C(=O)—O—, —S—, —S(=O)$_2$—, and —S(=O)$_2$—O—.

For R$^{91}$, examples of the hydrocarbon group having a substituent include lactone-containing cyclic groups represented by general formulae (a2-r-1) to (a2-r-7).

In addition, with respect to R$^{91}$, examples of a hydrocarbon group having a substituent include —SO$_2$— containing cyclic groups represented by general formula (a5-r-1) to (a5-r-4); and substituted aryl groups and monovalent heterocyclic groups represented by the following chemical formulae.

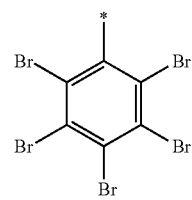

(r-ar-1)

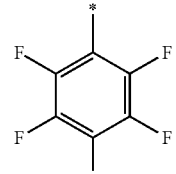

(r-ar-2)

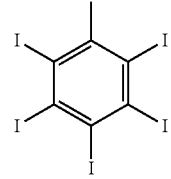

(r-ar-3)

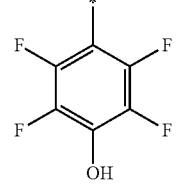

(t-ar-4)

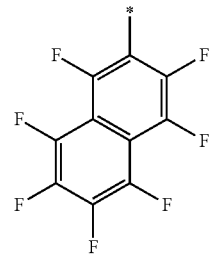

(r-ar-5)

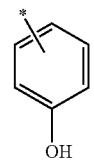

(r-ar-6)

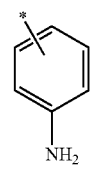

(r-ar-7)

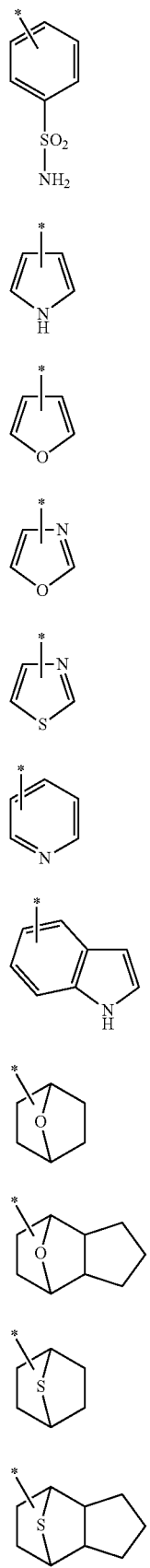
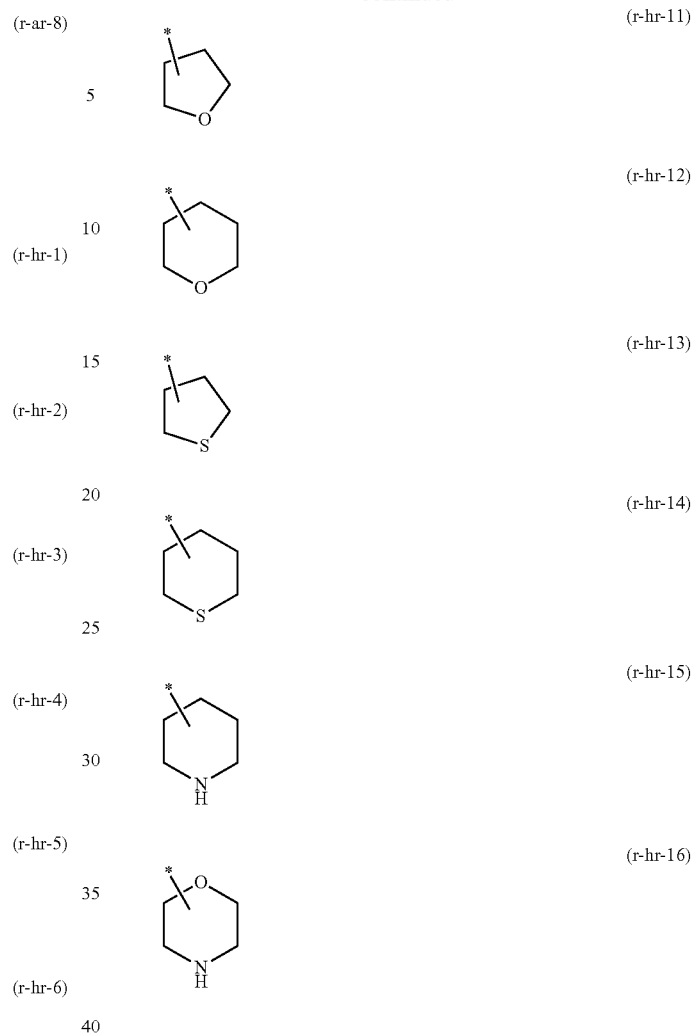

With respect to the structural unit (a9), a structural unit represented by general formula (a9-1-1) is preferable.

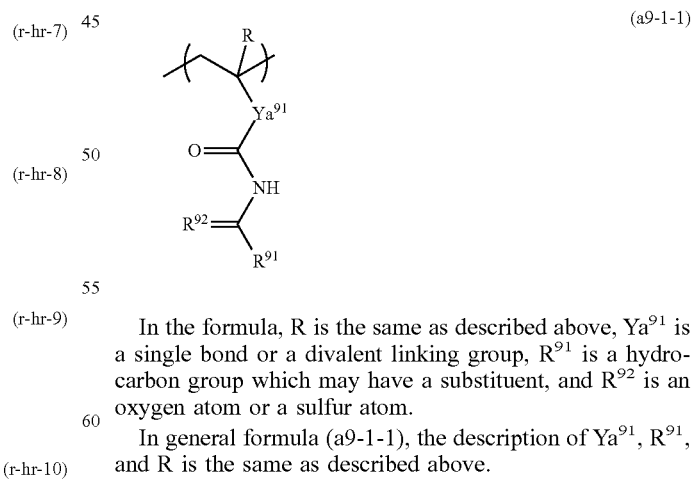

In the formula, R is the same as described above, $Ya^{91}$ is a single bond or a divalent linking group, $R^{91}$ is a hydrocarbon group which may have a substituent, and $R^{92}$ is an oxygen atom or a sulfur atom.

In general formula (a9-1-1), the description of $Ya^{91}$, $R^{91}$, and R is the same as described above.

In addition, $R^{92}$ is an oxygen atom or a sulfur atom.

Specific examples of the structural unit represented by general formula (a9-1) or general formula (a9-1-1) are described. In the following formulae, $R^{\alpha}$ represents a hydrogen atom, a methyl group, or a trifluoromethyl group.

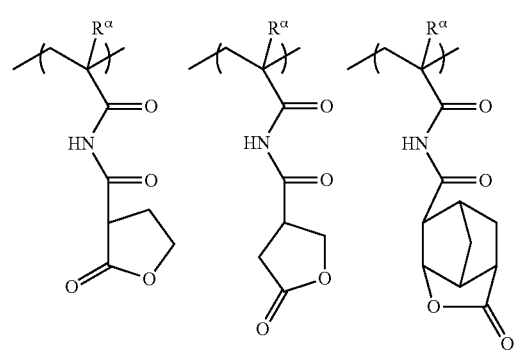
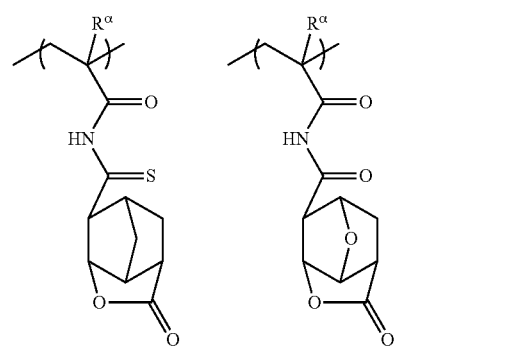
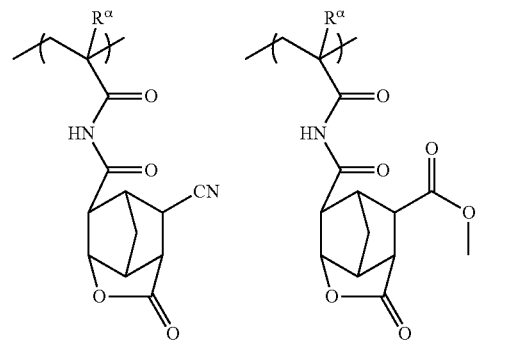
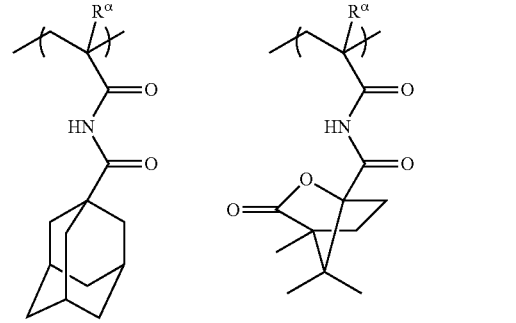
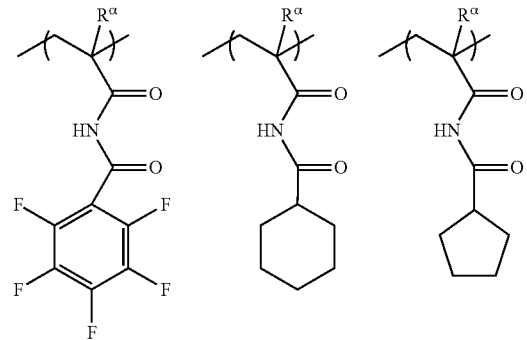
-continued
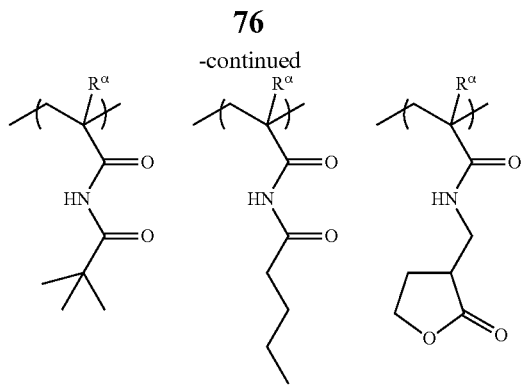
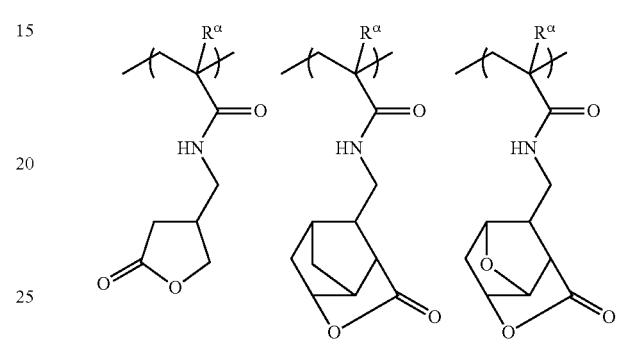
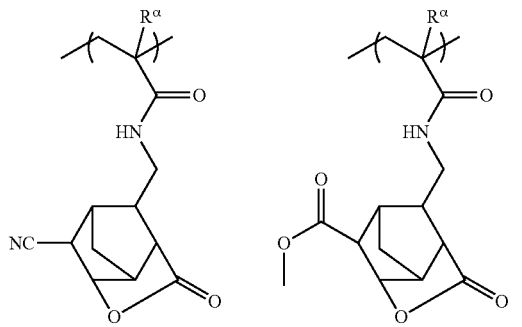
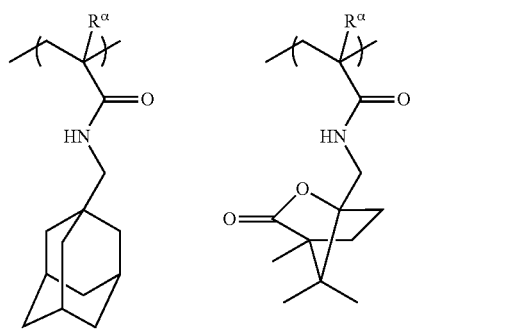
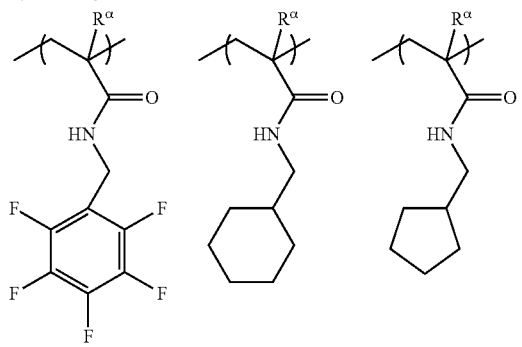

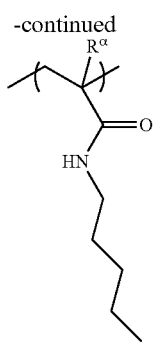

The structural unit (a9) contained in the (A1) component may be used alone or two or more kinds of thereof may be used in combination.

In the case where the (A1) component contains the structural unit (a9), the ratio of the structural unit (a9) is preferably 1 to 40 mol %, is further preferably 3 to 30 mol %, and is particularly preferably 10 to 30 mol %, with respect to the total (100 mol %) of the entire structural units for constituting the (A1) component.

When the ratio of the structural unit (a9) is set to be equal to or greater than the lower limit value, the lithography properties such as the developing property and EL margin are improved, on the other hand, when the ratio of the structural unit (a9) is set to be equal to or lower than the upper limit value, it becomes easier to take balance with other structural units.

The (A1) component is preferably a copolymer having a structural unit (a10) and a structural unit (a1), and is further preferably a copolymer having a structural unit (a10), a structural unit (a1), a structural unit (a2), and a structural unit (a3).

The (A) component can be obtained by polymerizing a monomer that derives each of the structural units by using a known radical polymerization method with a radical polymerization initiator such as azobisisobutyronitrile (AIBN) and azobisisobutyrate.

In addition, in the (A1) component, at the time of the polymerization, a —C(CF$_3$)$_2$-OH group may be introduced to a terminal by using a chain transfer agent such as HS—CH$_2$—CH$_2$—CH$_2$—C(CF$_3$)$_2$—OH in combination. As such, a copolymer to which a hydroxyalkyl group in which a portion of the hydrogen atoms of an alkyl group is substituted with a fluorine atom is introduced is effective in decreasing development defects and line edge roughness (LER: nonuniform irregularities of the line side walls).

In the present invention, The mass average molecular weight (Mw) (standard polystyrene determined by gel permeation chromatography) of the (A) component is not particularly limited, and is preferably 1,000 to 50,000, is further preferably 1,500 to 30,000, and is most preferably 2,000 to 20,000. When the mass average molecular weight is equal to or less than the upper limit value of the above range, the solubility with respect to a resist solvent is sufficient in the case where the (A) component is used as a resist, and when the mass average molecular weight of the (A) component is equal to or greater than the lower limit value of the above range, dry etching resistance and a resist pattern cross-sectional shape are improved.

In the resist composition of the present invention, the (A) component may be used alone, or two or more kinds thereof may be used in combination.

In the resist composition of the present invention, the content of the (A) component may be adjusted in accordance with a film thickness of a resist film to be formed.

Fluorine Additive Component; (F) Component

The (F) component exhibits the decomposability with respect to the alkali developing solution, and contains a fluororesin component (F1) (hereinafter, referred to as "(F1) component" in some cases") having a structural unit (f1) containing a base dissociable group.

Structural Unit (f1)

The structural unit (f1) is a structural unit containing a base dissociable group.

The "base dissociable group" in the present invention means an organic group which can be dissociated by the action of a base. Examples of the base include an alkali developing solution which is generally used in the lithography field. That is, "a base dissociable group" is a group which is dissociated under the action of the alkali developing solution (for example, 2.38% by mass of tetramethyl ammonium hydroxide (TMAH) aqueous solution (23° C.)).

The base dissociable group is dissociated by hydrolysis under the action of the alkali developing solution.

For this reason, at the same time as the base dissociable group is dissociated, a hydrophilic group is formed, the hydrophilicity of the (F) component is enhanced, and the affinity for the alkali developing solution is appropriately improved.

Specific examples of the base dissociable group include the groups respectively represented by general formulae (II-1) to (II-5).

In the present invention, the base dissociable group is preferably at least one kind selected from a group consisting of the groups respectively represented by general formulae (II-1) to (II-5), and is particularly preferably the groups respectively represented by general formulae (II-1), (II-4), and (II-5) from the viewpoint of the excellent properties of the hydrophilicity at the time of development, and ease of synthesis.

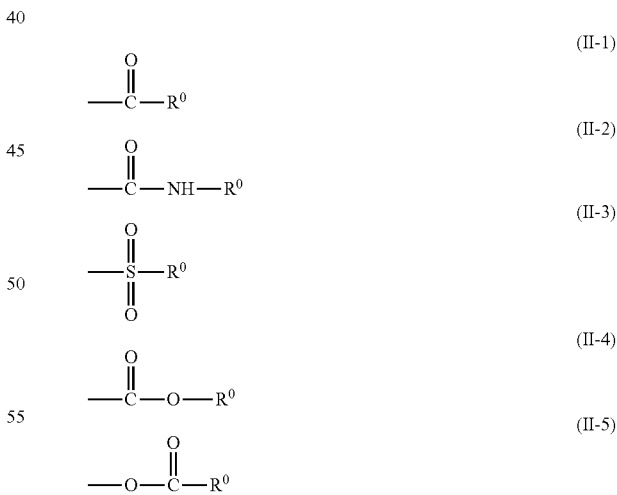

In the formulae, $R^0$'s are each independently an organic group which may have a fluorine atom.

In general formulae (II-1) to (II-5), $R^0$ is an organic group which may have a fluorine atom.

The "organic group" is a group containing at least one carbon atom.

The structure of $R^0$ may be linear, branched, or cyclic, and is preferably linear or branched.

With respect to $R^0$, the number of carbon atoms of the organic group is preferably 1 to 20, is further preferably 1 to 15, is particularly preferably 1 to 10, and is most preferably 1 to 5.

With respect to $R^0$, a fluorination rate is preferably equal to or greater than 25%, is further preferably equal to or greater than 50%, and is particularly preferably equal to or greater than 60%.

The "fluorination rate" means the ratio (%) of the number of fluorine atoms to the total number of hydrogen atoms and fluorine atoms in the organic group.

Preferred examples of $R^0$ include a methyl group, an ethyl group, and a fluorinated hydrocarbon group which may have a substituent.

Regarding the fluorinated hydrocarbon group which may have a substituent for $R^0$, the hydrocarbon group may be an aliphatic hydrocarbon group, or may an aromatic hydrocarbon group. Among them, an aliphatic hydrocarbon group is preferable.

The aliphatic hydrocarbon group means a hydrocarbon group having no aromaticity. The aliphatic hydrocarbon group may be saturated or unsaturated, and is usually preferably saturated.

That is, $R^0$ is preferably a fluorinated saturated hydrocarbon group or a fluorinated unsaturated hydrocarbon group, and among them, a fluorinated saturated hydrocarbon group, that is, a fluorinated alkyl group is particularly preferable.

Examples of the fluorinated alkyl group include a group in which at least one of the hydrogen atoms of an unsubstituted alkyl group described below is substituted with a fluorine atom. The fluorinated alkyl group may be a group in which a portion of the hydrogen atom of the unsubstituted alkyl group is substituted with a fluorine atom, or may be a group (a perfluoroalkyl group) in which all of the hydrogen atoms of the unsubstituted alkyl group are substituted with a fluorine atom.

The unsubstituted alkyl group may be linear, branched, or cyclic, and may be a combination of a linear or branched alkyl group and a cyclic alkyl group.

The number of carbon atoms of the unsubstituted linear alkyl group is preferably 1 to 10, and is further preferably 1 to 8. Specifically, examples thereof include a methyl group, an ethyl group, an n-propyl group, an n-butyl group, an n-pentyl group, an n-hexyl group, an n-heptyl group, an n-octyl group, an n-nonyl group, an n-decyl group.

The number of carbon atoms of the unsubstituted branched alkyl group is preferably 3 to 10, and is further preferably 3 to 8. The branched alkyl group is preferably a tertiary alkyl group.

Examples of the unsubstituted cyclic alkyl group include a group in which one hydrogen atom is removed from a polycycloalkane such as a monocycloalkane, a bicycloalkane, tricycloalkane, and tetracycloalkane. Specific examples thereof include a monocycloalkyl group such as a cyclopentyl group and a cyclohexyl group; a polycycloalkyl group such as an adamantyl group, a norbornyl group, an isobornyl group, a tricyclodecyl group, and a tetracyclododecyl group.

Examples of the combination of the unsubstituted linear or branched alkyl group and the cyclic alkyl group include a group in which a cyclic alkyl group is bonded to a linear or branched alkyl group as a substituent, and a group in which a linear or branched alkyl group is bonded to a cyclic alkyl group as a substituent.

Examples of the substituent that a fluorinated hydrocarbon group may have include an alkyl group having 1 to 5 carbon atoms.

With respect to $R^0$, as a fluorinated alkyl group, a linear or branched fluorinated alkyl group is preferable. Particularly, a group represented by general formula (III-1) or (III-2) is preferable, and among them, a group represented by general formula (III-1) is further preferable.

(III-1)

(III-2)

In general formula (III-1), $R^{41'}$ is an unsubstituted alkylene group having 1 to 9 carbon atoms, and $R^{42'}$ is a fluorinated alkyl group having 1 to 9 carbon atoms. Here, the total number of carbon atoms of $R^{41'}$ and $R^{42'}$ are equal to or less than 10. In addition, in general formula (III-2), $R^{74}$ to $R^{76}$ each independently is a linear alkyl group having 1 to 5 carbon atoms, and at least one of $R^{74}$ to $R^{76}$ is an alkyl group having a fluorine atom.

In general formula (III-1), an alkylene group for $R^{41'}$ may be linear, branched, or cyclic, and is preferably linear or branched. In addition, the number of carbon atoms is preferably 1 to 5.

Particularly, $R^{41'}$ is preferably a methylene group, an ethylene group, and a propylene group.

$R^{42'}$ is preferably linear or branched fluorinated alkyl group having 1 to 5 carbon atoms, and is particularly preferably a perfluoroalkyl group. Among them, a trifluoromethyl group ($-CF_3$), a tetrafluoroethyl group ($-C_2F_4H$), and $-C_2F_5$ are preferable.

In general formula (III-2), an alkyl group for $R^{74}$ to $R^{76}$ is preferably an ethyl group and a methyl group, and is particularly preferably a methyl group. Among alkyl groups for $R^{74}$ to $R^{76}$, at least one may be a fluorinated alkyl group, or all of them may be a fluorinated alkyl group.

In the present invention, the (F1) component preferably has a structural unit represented by general formula (f1-1), or a structural unit represented by general formula (f1-2), as a structural unit (f1).

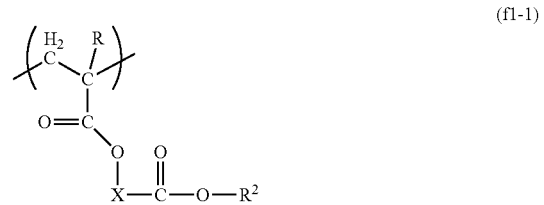

(f1-1)

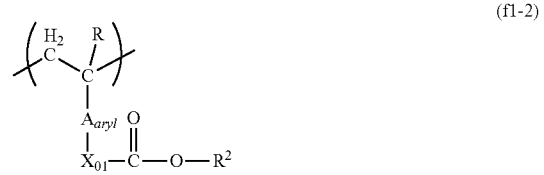

(f1-2)

In the formula, each R is independently a hydrogen atom, an alkyl group having 1 to 5 carbon atoms, or a halogenated alkyl group having 1 to 5 carbon atoms. X is a divalent linking group having no acid dissociable moiety. $A_{aryl}$ is a divalent aromatic cyclic group which may have a substituent. $X_{01}$ is a single bond or a divalent linking group. Each $R^2$ is independently an organic group having a fluorine atom.

In general formulae (f1-1) and (f1-2), R is the same as described above.

In general formula (f1-1), X is a divalent linking group having no acid dissociable moiety.

The "acid dissociable moiety" means a potion where an acid generated upon exposure acts to dissociate in the organic group.

Examples of the divalent linking group having no acid dissociable moiety for X include a divalent hydrocarbon group which may have a substituent, and a divalent linking group containing a heteroatom.

Hydrocarbon Group which May have Substituent

The phrase that a hydrocarbon group "has a substituent" means that a part or all of the hydrogen atoms in the hydrocarbon group are substituted with groups or atoms other than a hydrogen atom.

The hydrocarbon group may be an aliphatic hydrocarbon group, and may be an aromatic hydrocarbon group.

The aliphatic hydrocarbon group means a hydrocarbon group having no aromaticity. The aliphatic hydrocarbon group may be saturated or unsaturated, and is usually preferably saturated.

Specific examples of the aliphatic hydrocarbon group include a linear or branched aliphatic hydrocarbon group, and an aliphatic hydrocarbon group including a ring in the structure.

The number of carbon atoms of the linear or branched aliphatic hydrocarbon group is preferably 1 to 10, is further preferably 1 to 8, is further still preferably 1 to 5, is particularly preferably 1 to 3, and is most preferably 2.

As the linear aliphatic hydrocarbon group, the linear alkylene group is preferable, and specifically, examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

As the branched aliphatic hydrocarbon group, a branched chain alkylene group is preferable, and specifically, examples thereof include an alkyl alkylene group such as an alkyl methylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an alkyl ethylene group such as —$CH(CH_3)CH_2$—, —$CH(CH_3)CH(CH_3)$—, —$C(CH_3)_2CH_2$—, —$CH(CH_2CH_3)CH_2$—, and —$CH(CH_2CH_3)CH_2$—; an alkyl trimethylene group such as —$CH(CH_3)CH_2CH_2$—, and —$CH_2CH(CH_3)CH_2$—; and an alkyl tetramethylene group such as —$CH(CH_3)CH_2CH_2CH_2$— and —$CH_2CH(CH_3)CH_2CH_2$—. As an alkyl group in the alkyl alkylene group, a linear alkyl group having 1 to 5 carbon atoms is preferable.

The chain (linear or branched) aliphatic hydrocarbon group may or may not have a substituent. Examples of the substituent include a fluorine atom, a fluorinated lower alkyl group having 1 to 5 carbon atoms, which is substituted with a fluorine atom, and an oxygen atom (=O)

Examples of the aliphatic hydrocarbon group containing a ring include a cyclic aliphatic hydrocarbon group (a group obtained by removing two hydrogen atoms from an aliphatic hydrocarbon ring), a group in which the cyclic aliphatic hydrocarbon group is bonded to a terminal of the chain aliphatic hydrocarbon group, or the cyclic aliphatic hydrocarbon group is present in the middle of the chain aliphatic hydrocarbon group.

The number of carbon atoms of the cyclic aliphatic hydrocarbon group is preferably 3 to 20, and is further preferably 3 to 12.

The cyclic aliphatic hydrocarbon group may be a polycyclic group, and may be a monocyclic group. The monocyclic alicyclic hydrocarbon group is preferably a group obtained by removing two hydrogen atoms from monocycloalkane having 3 to 6 carbon atoms, and examples of the monocycloalkane include cyclopentane and cyclohexane.

The polycyclic group is preferably a group obtained by removing two hydrogen atoms from polycycloalkane having 7 to 12 carbon atoms, and specific examples of the polycycloalkane include adamantane, norbornane, isobornane, tricyclodecane, and tetracyclododecane.

The cyclic aliphatic hydrocarbon group may or may not have a substituent. Examples of the substituent include a lower alkyl group having 1 to 5 carbon atoms, a fluorine atom, a fluorinated lower alkyl group having 1 to 5 carbon atoms, which is substituted with a fluorine atom, and an oxygen atom (=O).

Examples of the aromatic hydrocarbon group include a divalent aromatic hydrocarbon group obtained by further removing one hydrogen atom from the aromatic hydrocarbon nucleus of a monovalent aromatic hydrocarbon group such as a phenyl group, a biphenyl group, a fluorenyl group, a naphthyl group, an anthryl group, and a phenanthryl group;

an aromatic hydrocarbon group in which a part of the carbon atoms constituting the ring of the divalent aromatic hydrocarbon group is substituted with a heteroatom such as an oxygen atom, a sulfur atom, and a nitrogen atom; and an aromatic hydrocarbon group which is an arylalkyl group such as a benzyl group, a phenethyl group, a 1-naphthylmethyl group, a 2-naphthylmethyl group, a 1-naphthylethyl group, and a 2-naphthylethyl group, and is obtained by further removing one hydrogen atom from the aromatic hydrocarbon nucleus.

Among them, the divalent aromatic hydrocarbon group is preferable, an aromatic hydrocarbon group obtained by further removing one hydrogen atom from a phenyl group is further preferable, and an aromatic hydrocarbon group obtained by further removing one hydrogen atom from a naphthyl group are particularly preferable.

The number of carbon atoms of an alkyl chain in the aryl alkyl group is preferably 1 to 4, is further preferably 1 or 2, and is particularly preferably 1.

The aromatic hydrocarbon group may or may not have a substituent. Examples of the substituent include a lower alkyl group having 1 to 5 carbon atoms, a fluorine atom, a fluorinated lower alkyl group having 1 to 5 carbon atoms, which is substituted with a fluorine atom, and an oxygen atom (=O).

Among them, as the hydrocarbon group which may have a substituent, a linear, branched, or cyclic aliphatic hydrocarbon group is preferable, a divalent aromatic hydrocarbon group is further preferable, a group obtained by further removing one hydrogen atom from a methylene group, an ethylene group, —$CH(CH_3)$—, and a tetracyclododecanyl group, an aromatic hydrocarbon group obtained by further removing one hydrogen atom from a phenyl group.

Divalent Linking Group Containing Heteroatom

A heteroatom is an atom other than a carbon atom and a hydrogen atom, and examples thereof include an oxygen atom, a nitrogen atom, a sulfur atom, and a halogen atom.

Examples of the divalent linking group containing a heteroatom include —O—, —C(=O)—, —C(=O)—O—, a carbonate bond (—O—C(=O)—O—), —NH—, —NR$^{04}$— (R$^{04}$ is an alkyl group), —NH—C(=O)—, =N—, and a combination of "the groups" and a divalent hydrocarbon group.

Examples of the divalent hydrocarbon group include the same groups as a hydrocarbon group which may have a substituent, and a linear or branched aliphatic hydrocarbon group is preferable.

Among them, as the divalent linking group containing a heteroatom, a combination of "the groups" and a divalent hydrocarbon group is further preferable, and specifically, a combination of "the groups" and the aliphatic hydrocarbon group, and a combination of the aliphatic hydrocarbon group, "the groups", and the aliphatic hydrocarbon group are particularly preferable.

In general formula (f1-2), $A_{aryl}$ is a divalent aromatic cyclic group which may have a substituent. Specific examples of $A_{aryl}$ include a group obtained by removing two hydrogen atoms from an aromatic hydrocarbon ring which may have a substituent.

The number of carbon atoms of the cyclic skeleton of an aromatic cyclic group for $A_{aryl}$ is preferably 6 to 15, and examples thereof include a benzene ring, a naphthalene ring, a phenanthrene ring, and an anthracene ring. Among them, a benzene ring or a naphthalene ring is particularly preferable.

In $A_{aryl}$, examples of the substituent that an aromatic cyclic group may have include a halogen atom, an alkyl group, an alkoxy group, a halogenated alkyl group having 1 to 5 carbon atoms, and an oxygen atom (=O). Examples of the halogen atom include a fluorine atom, a chlorine atom, an iodine atom, and a bromine atom. AS the substituent that an aromatic cyclic group for $A_{aryl}$ may have, a fluorine atom is preferable.

The aromatic cyclic group for $A_{aryl}$ may have a substituent, or may not have a substituent. Among them, an aromatic cyclic group which may not have a substituent is preferable.

In $A_{aryl}$, in a case where the aromatic cyclic group has a substituent, the number of the substituents may be one, or two or more, but is preferably one or two, and is further preferably one.

In general formula (f1-2), $X^{01}$ is a single bond or a divalent linking group. Examples of the divalent linking group include an alkylene group having 1 to 10 carbon atoms, —O—, —C(=O)—, —C(=O)—O—, a carbonate bond (—O—C(=O)—O—), —NH—C(=O)—, and a combination thereof. Among them, a combination of —O— and an alkylene group having 1 to 10 carbon atoms is most preferable.

Examples of the alkylene group having 1 to 10 carbon atoms include a linear, branched, or cyclic alkylene group. Among them, a linear or branched alkylene group having 1 to 5 carbon atoms, and a cyclic alkylene group having 4 to 10 carbon atoms are preferable.

Among the structural units represented by general formula (f1-1), structural units represented by general formulae (f1-11) to (f1-15) are preferable.

In addition, among the structural units represented by general formula (f1-2), structural units represented by general formulae (f1-21) to (f1-27) are preferable.

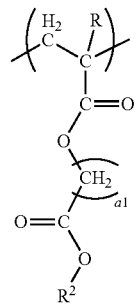

(f1-11)

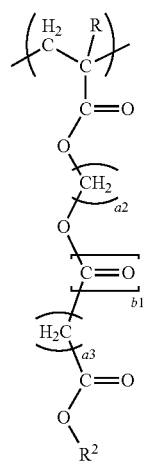

(f1-12)

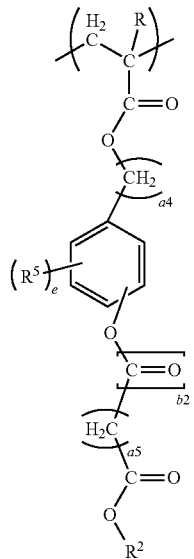

(f1-13)

(f1-14)
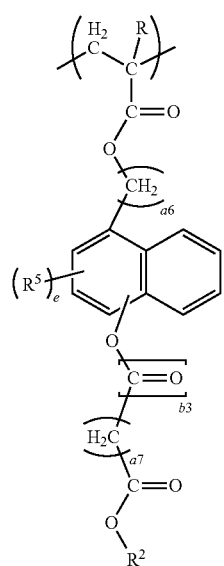
(f1-15)
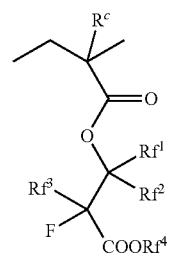
(f1-21)
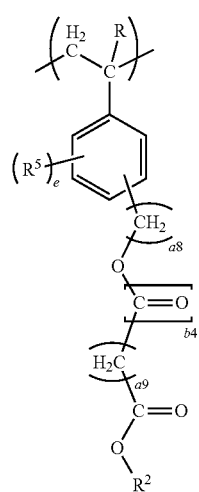
(f1-22)
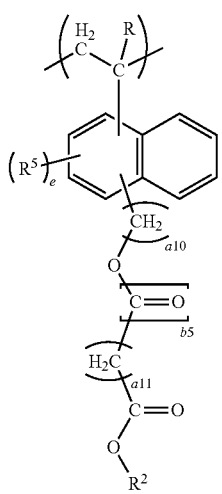
(f1-23)
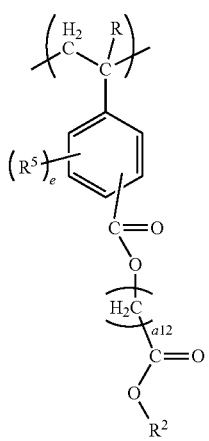
(f1-24)
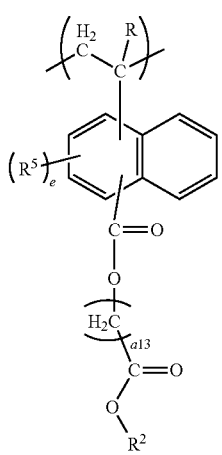

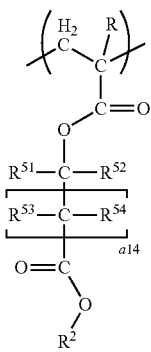

(f1-25)

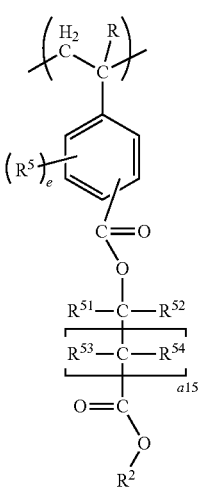

(f1-26)

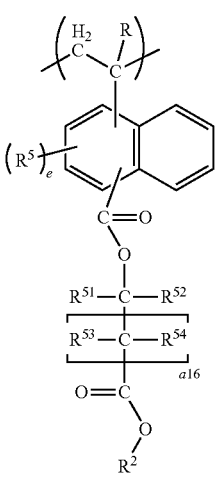

(f1-27)

In general formulae (f1-11) to (f1-14), (f1-21) to (f1-24), and (f1-25) to (f1-27), R and $R^2$ are the same as described above; $R^{31}$ to $R^{52}$ are each independently an alkyl group having 1 to 10 carbon atoms; $R^{53}$ to $R^{54}$ are each independently a hydrogen atom or an alkyl group having 1 to 10 carbon atoms; a1, a2, a3, a5, a7, a9, and a11 to a13 are each independently an integer of 1 to 5; a4, a6, a8, and a10 are each independently an integer of 0 to 5; a14 to a16 are each independently an integer of 0 to 5; b1 to b5 are each independently 0 or 1; $R^5$ is a substituent; and e is an integer of 0 to 2.

In general formulae (f1-11) to (f1-14), (f1-21) to (f1-24), and (f1-25) to (f1-27), R is preferably a hydrogen atom or a methyl group.

In general formula (f1-11), a1 is preferably an integer of 1 to 3, or is further preferably 1 or 2.

In general formula (f1-12), a2 and a3 are each independently preferably an integer of 1 to 3, and is further preferably 1 or 2.

In general formula (f1-13), a4 is preferably an integer of 0 to 3, is further preferably an integer of 0 to 2, and is most preferably 0 or 1.

a5 is preferably an integer of 1 to 3, and is further preferably an integer of 1 or 2.

Examples of the substituent for $R^5$ include a halogen atom, an alkyl group having 1 to 5 carbon atoms, an alkoxy group having 1 to 5 carbon atoms, a halogenated alkyl group having 1 to 5 carbon atoms, and an oxygen atom (=O). Examples of the alkyl group having 1 to 5 carbon atoms include the same group as that of an alkyl group having 1 to 5 carbon atoms for the above R. Examples of the halogen atom include a fluorine atom, a chlorine atom, an iodine atom, and a bromine atom. Examples of the halogenated alkyl group having 1 to 5 carbon atoms include the same group as that of a halogenated alkyl group having 1 to 5 carbon atoms for the above R.

e is preferably 0 or 1, and is particularly preferably 0 in terms of the industrial availability.

b2 is preferably 0.

In general formula (f1-14), a6 is preferably an integer of 0 to 3, is further preferably an integer of 0 to 2, and is most preferably 0 or 1.

a7 is preferably an integer of 1 to 3, and is further preferably 1 or 2.

b3 is preferably 0.

$R^5$ and e are each the same as described above.

In general formula (f1-21), a8 is preferably an integer of 0 to 3, is further preferably an integer of 0 to 2, and is most preferably 0 or 1.

a9 is preferably an integer of 1 to 3, and is further preferably 1 or 2.

b4 is preferably 0.

$R^5$ and e are each the same as described above.

In general formula (f1-22), a10 is preferably an integer of 0 to 3, is further preferably an integer of 0 to 2, and is most preferably 0 or 1.

a11 is preferably an integer of 1 to 3, and is further preferably 1 or 2.

b5 is preferably 0.

$R^5$ and e are each the same as described above.

In general formula (f1-23), a12 is preferably an integer of 1 to 3, and is further preferably 1 or 2.

$R^5$ and e are each the same as described above.

General formula (f1-24), a13 is preferably an integer of 1 to 3, and is further preferably 1 or 2.

$R^5$ and e are each the same as described above.

In general formulae (f1-25) to (f1-27), a14, a15, and a16 are each preferably an integer of 0 to 3, are each further preferably an integer of 0 to 2, and are each most preferably 0 or 1.

It is preferable that $R^{51}$ to $R^{52}$ are each independently a linear, branched, or cyclic alkyl group having 1 to 10 carbon atoms, and examples thereof include a methyl group, an ethyl group, an n-propyl group, an isopropyl group, an n-butyl group, an isobutyl group, a tert-butyl group, a tert-amyl group, a cyclopentyl group, a cyclohexyl group, a cyclooctyl group, a norbornyl group, an isobornyl group, a tricyclodecanyl group, an adamantyl group, and a tetracyclododecanyl group. Among them, a group having carbon atoms 1 to 6 is further preferable, a group having 1 to 4 carbon atoms is particularly preferable, and a methyl group or an ethyl group is most preferable.

It is preferable that $R^{53}$ to $R^{54}$ are each independently a linear, branched, or cyclic alkyl group having 1 to 10 carbon atoms. Examples of the linear, branched, or cyclic alkyl groups having 1 to 10 carbon atoms for $R^{53}$ to $R^{54}$ are the same as those for $R^{51}$ to $R^{52}$.

In general formula (f1-26) to (f1-27), $R^5$ and e are each the same as described above.

In general formula (f1-15), $R^c$ is a hydrogen atom or a methyl group. In general formula (f1-15), $Rf^1$ and $Rf^2$ are each independently a hydrogen atom, an alkyl group having 1 to 4 carbon atoms, or a fluorinated alkyl group having 1 to 4 carbon atoms.

The alkyl groups for $Rf^1$ and $Rf^2$ having 1 to 4 carbon atoms may be linear, branched, or cyclic, but a linear or branched alkyl group is preferable. Specifically, a methyl group and an ethyl group are preferable, and an ethyl group is particularly preferable.

The fluorinated alkyl groups for $Rf^1$ and $Rf^2$ having 1 to 4 carbon atoms are the groups in which at least one of the hydrogen atoms of an alkyl group having 1 to 4 carbon atoms is substituted with a fluorine atom. Among the fluorinated alkyl groups, an alkyl group in a state of not being substituted with a fluorine atom may be linear, branched, or cyclic, and examples thereof include the same groups as "the alkyl groups for $Rf^1$ and $Rf^2$ having 1 to 4 carbon atoms".

Among them, it is preferable that $Rf^1$ and $Rf^2$ are a hydrogen atom or an alkyl group having 1 to 4 carbon atoms, and it is particularly preferable that one of $Rf^1$ and $Rf^2$ is a hydrogen atom, and the other one is an alkyl group having 1 to 4 carbon atoms.

In general formula (f1-15), $Rf^3$ is a fluorine atom or a fluorinated alkyl group having 1 to 4 carbon atoms.

Examples of the fluorinated alkyl group for $Rf^3$ having 1 to 4 carbon atoms include the same group as "the fluorinated alkyl groups for $Rf^1$ and $Rf^2$ having 1 to 4 carbon atoms", and the number of carbon atoms is preferably 1 to 3, and is further preferably 1 or 2.

In the fluorinated alkyl group for $Rf^3$, the ratio (fluorination rate (%)) of the number of the fluorine atom to the total number of fluorine atoms and hydrogen atoms which are contained in the fluorinated alkyl group is preferably 30% to 100%, and is further preferably 50% to 100%. As the fluorination rate is high, the hydrophobicity of the resist film is enhanced.

In general formula (f1-15), $Rf^4$ is a linear or branched alkyl group having 1 to 4 carbon atoms, a linear fluorinated alkyl group having 1 to 4 carbon atoms. Among them a linear alkyl group having 1 to 4 carbon atoms and a linear fluorinated alkyl group having 1 to 4 carbon atoms are preferable.

Specific examples of the alkyl group for $Rf^4$ include a methyl group, an ethyl group, a propyl group, an isopropyl group, an n-butyl group, an isobutyl group, and a tert-butyl group. Among them, a methyl group and an ethyl group are preferable, and a methyl group is most preferable.

As the fluorinated alkyl group for $Rf^4$, specifically, $-CH_2-CF_3$, $-CH_2-CF_2-CF_3$, and $-CH_2-CF_2-CF_2-CF_3$ are preferable, and $-CH_2-CF_3$ is most preferable.

Hereinafter, specific examples of the structural units represented by general formulae (f1-11) to (f1-15), and general formulae (f1-21) to (f1-27) are described.

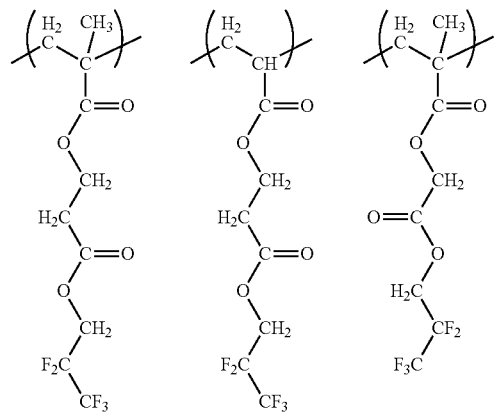

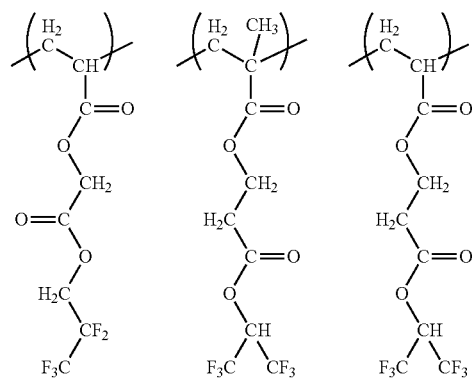

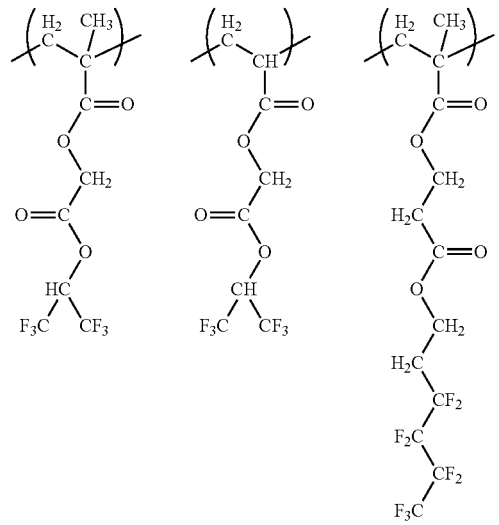

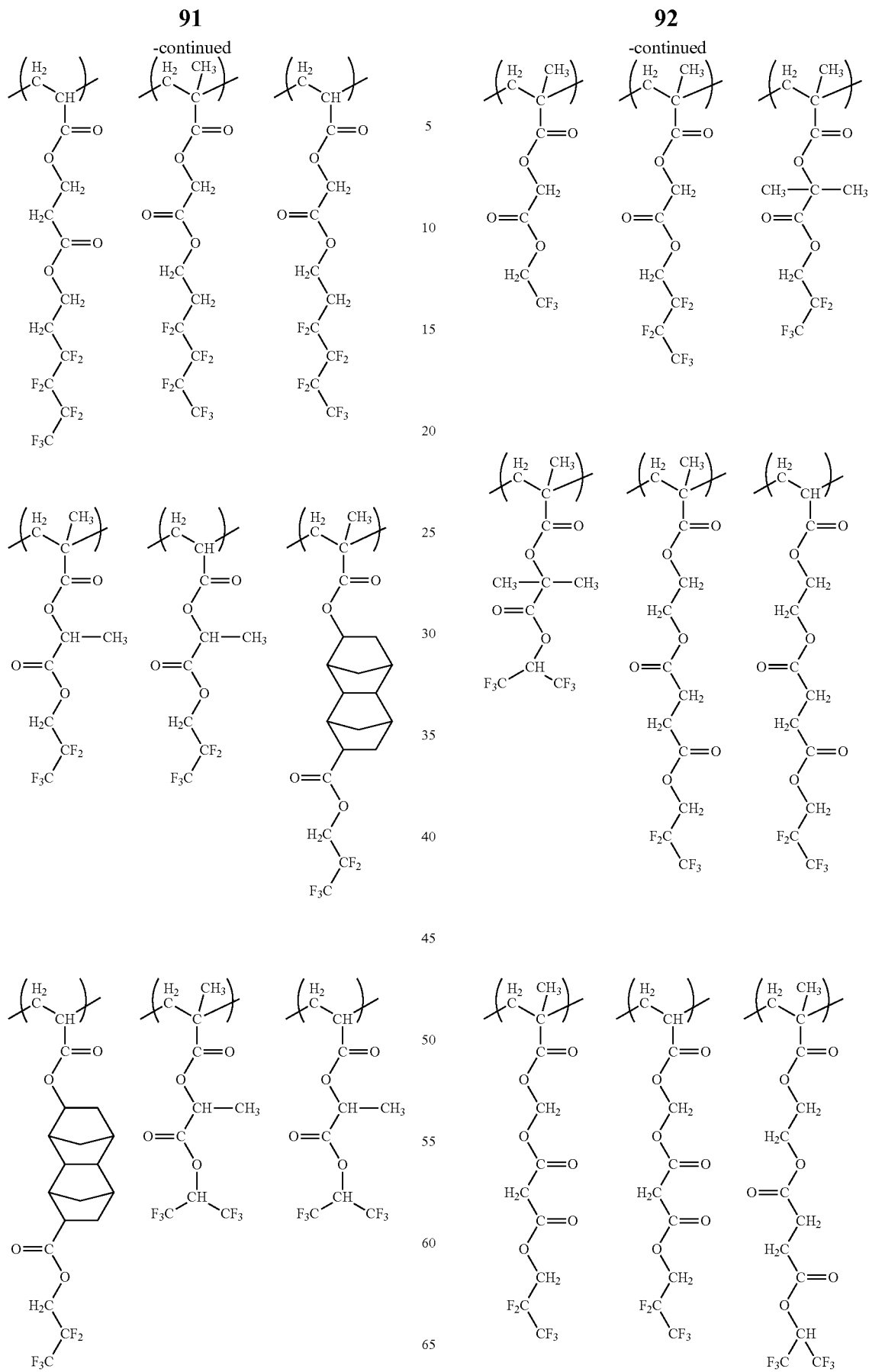

93
-continued
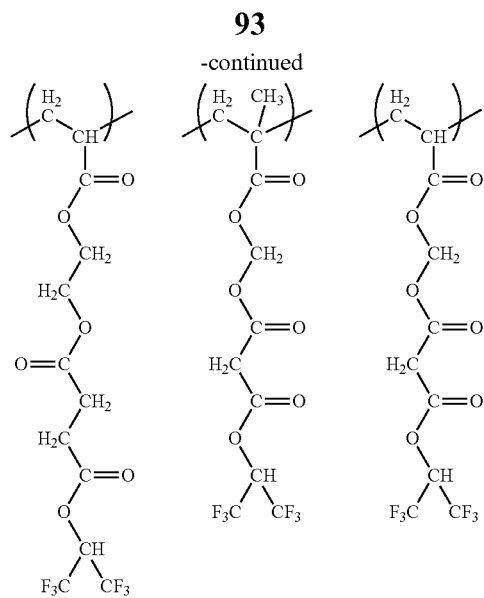
94
-continued
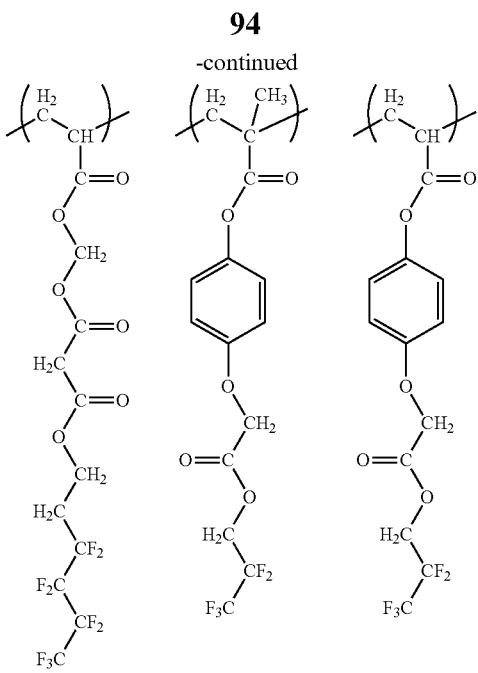
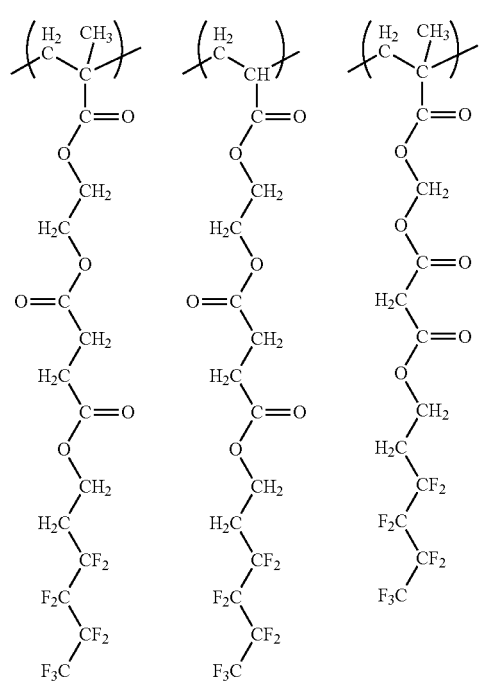
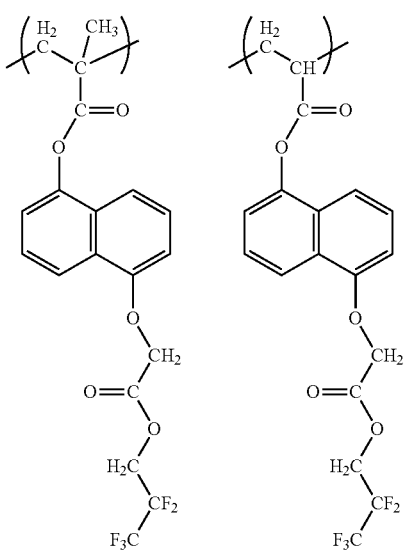

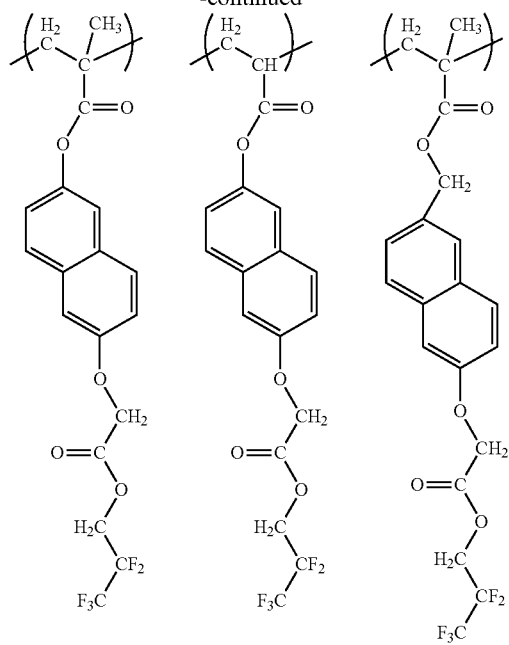
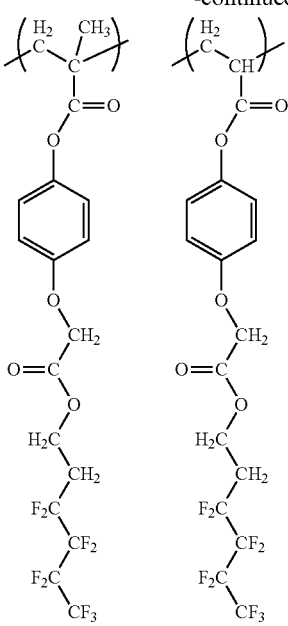
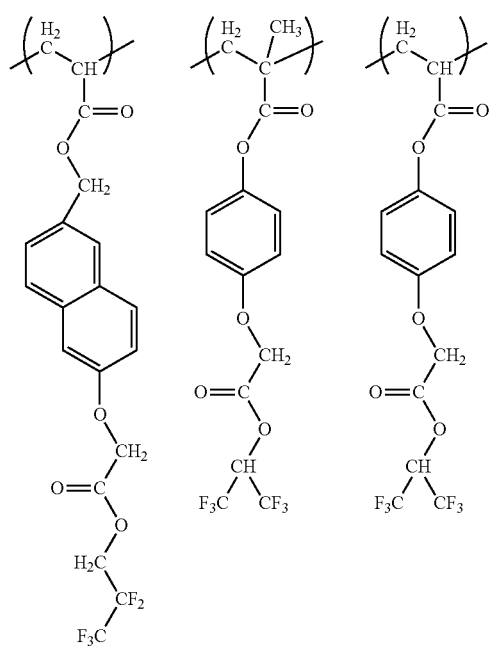
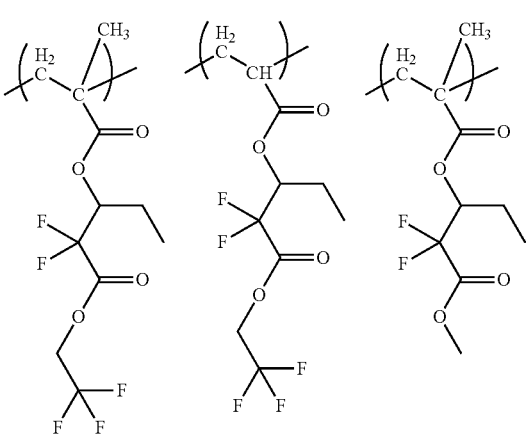
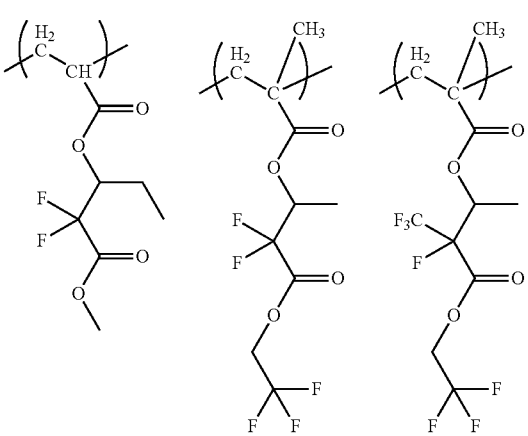

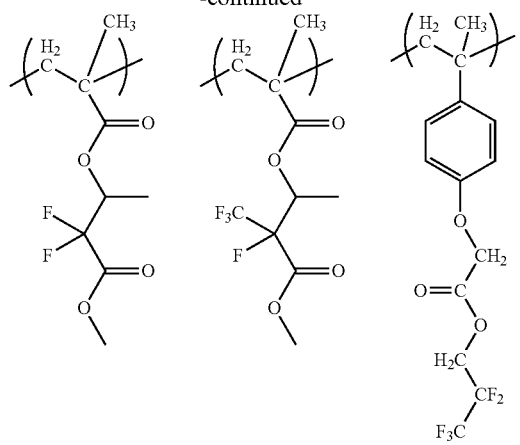
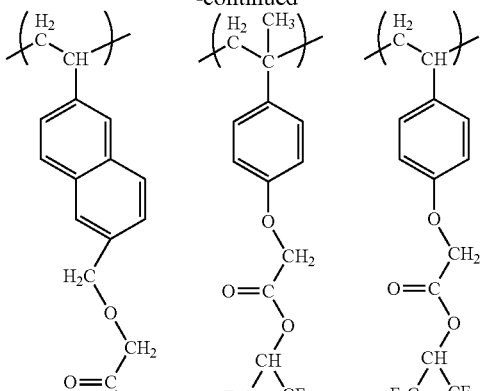
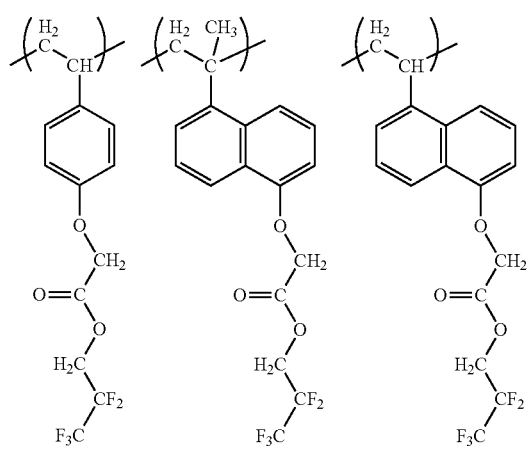
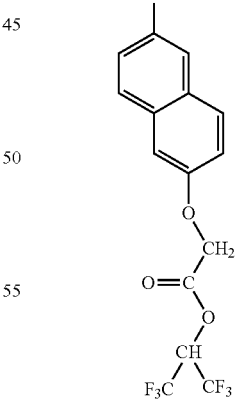
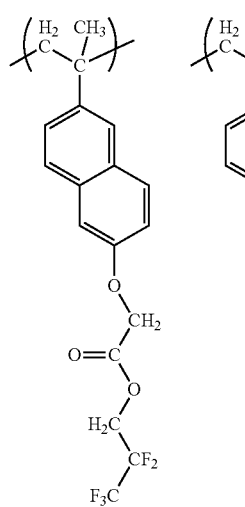
As the structural unit (f1), at least one kind selected from the group consisting of the structural units represented by any of general formulae (f1-11) to (f1-15) and (f1-21) to (f1-24) is preferable, at least one kind selected from the group consisting of the structural units represented by any of general formulae (f1-11) to (f1-13), (f1-15), (f1-21), and (f1-22) is further preferable, and at least one kind selected from the group consisting of the structural units represented by any of general formulae (f1-11), (f1-15), and (f1-22) is particularly preferable.

In the (F) component, the structural unit (f1) may be used alone, or two or more kinds thereof may be used in combination.

In the (F) component, the ratio of the structural unit (f1) is preferably 10 to 100 mol %, is further preferably 30 to 90 mol %, and is still further preferably 55 to 85 mol %, with respect to the total (100 mol %) of the entire structural units constituting the (F) component. When the ratio of the structural unit (f1) is equal to or greater than the lower limit value of the above range, in the forming of the resist pattern, it becomes hydrophilic at the time of alkali development, and the generation of defects due to deposits on the resist surface and the like can be reduced. When the ratio of the structural unit (f1) is equal to or lower than the upper limit value of the above range, it becomes easier to take balance with other structural units.

Structural Unit (f2)

The (F1) component may have a structural unit (f2) containing a lactone-containing cyclic group in addition to the structural unit (f1).

Examples of the lactone-containing cyclic group in the structural unit (f2) include the same group as that of the lactone-containing cyclic group in the structural unit (a2). Among them, as the structural unit (f2), a structural unit having a group represented by general formula (f2-r-1) is preferable.

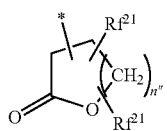

In the formula, $Rf^{21}$'s each independently a hydrogen atom, an alkyl group, an alkoxy group, a hydroxyl group, a hydroxyalkyl group, or a cyano group. n" is an integer of 0 to 2. A symbol of * represents a bond.

In general formula (f2-r-1), an alkyl group, an alkoxy group, and a hydroxyalkyl group for $Rf^{21}$ are the same as an alkyl group, an alkoxy group, and a hydroxyalkyl group for $Ra'^{21}$ in general formulae (a2-r-1) to (a2-r-7).

As the group represented by general formula (f2-r-1), a group represented by general formula (f2-r-1-1) is further preferable.

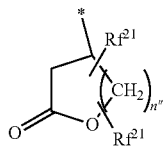

In the formula, $Rf^{21}$'s are each independently a hydrogen atom, an alkyl group, an alkoxy group, a hydroxyl group, a hydroxyalkyl group, or a cyano group. n" is an integer of 0 to 2. A symbol of * represents a bond.

In general formula (f2-r-1-1), $Rf^{21}$ and n" are the same as $Rf^{21}$ and n" in general formula (f2-r-1).

As the structural unit (f2), among them, a structural unit derived from acrylic ester which may be obtained by substituting a hydrogen atom bonded to an α-position carbon atom with a substituent is preferable.

The structural unit (f2) is preferably a structural unit represented by general formula (f2-1).

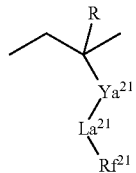

In the formula, R is a hydrogen atom, an alkyl group having 1 to 5 carbon atoms, or a halogenated alkyl group having 1 to 5 carbon atoms. $Ya^{21}$ is a single bond or a divalent linking group. $La^{21}$ is —O—, —COO—, —CON(R')—, —OCO—, —CONHCO—, or —CONHCS—, and R' represents a hydrogen atom or a methyl group. Here, in a case where $La^{21}$ is —O—, $Ya^{21}$ is not —CO—. $Rf^{21}$ is a lactone-containing cyclic group.

In general formula (f2-1), R, $Ya^{21}$, $La^{21}$, and R' are the same as R, $Ya^{21}$, $La^{21}$, and R' in general formula (a2-1).

In general formula (f2-1), $Rf^{21}$ is a lactone-containing cyclic group. Examples of the lactone-containing cyclic group for $Rf^{21}$ include the same group as the lactone-containing cyclic group in the structural unit (a2). Among them, as the lactone-containing cyclic group for $Rf^{21}$, a group represented by general formula (f2-r-1) is preferable, and a group represented by general formula (f2-r-1-1) is further preferable.

The structural unit (f2) of the (F1) component may be used alone, or two or more kinds thereof may be used in combination.

In a case where the (F1) component has the structural unit (f2), the ratio of the structural unit (f2) is preferably 5 to 60 mol %, is further preferably 10 to 50 mol %, and is still further preferably 15 to 45 mol %, with respect to the total (100 mol %) of the entire structural units constituting the (F1) component.

When the ratio of the structural unit (f2) is equal to or greater than the lower limit value of the above range, it is effective to reduce defects. When the ratio of the structural unit (f2) is equal to or lower than the upper limit value, it becomes easier to take balance with other structural units.

Structural Unit (f3)

The (F1) component may further have a structural unit (f3) represented by general formula (f3-1) in addition to the structural unit (f1) or the structural units (f1) and (f2).

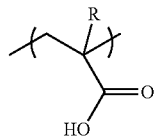

In the formula, R is a hydrogen atom, an alkyl group having 1 to 5 carbon atoms, or a halogenated alkyl group having 1 to 5 carbon atoms.

In general formula (f3-1), R is the same as described above.

The structural unit (f3) of the (F1) component may be used alone, or two or more kinds thereof may be used in combination.

In a case where the (F1) component has the structural unit (f3), the ratio of the structural unit (f3) is preferably 5 to 60 mol %, is further preferably 10 to 50 mol %, and is still further preferably 15 to 45 mol %, with respect to the total (100 mol %) of the entire structural units constituting the (F1) component.

When the ratio of the structural unit (f3) is equal to or greater than the lower limit value of the above range, an effect of suppressing the generation of the defects is further improved. When the ratio of the structural unit (f3) is equal to or lower than the upper limit value of the above range, it is possible to take balance with other structural units.

Structural Unit (f4)

The (F1) component may further have a structural unit (f4) derived from an acrylic ester containing an acid-dissociative-dissolution controlling group in addition to the structural unit (f1) or the structural units (f1) and (f2) and/or (f3).

Examples of the structural unit (f4) include the same group as the structural unit (a1) in the (A1) component.

Among them, the structural unit (f4) is preferably at least one kind of structural unit selected from the structural units represented by general formula (f4-1) and general formula (f4-2), and is further preferably a structural unit represented by general formula (f4-1).

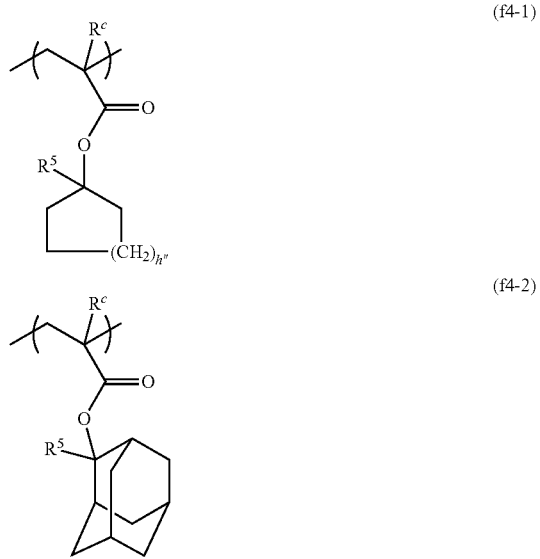

(f4-1)

(f4-2)

In the formulae, $R^c$'s are each independently a hydrogen atom or a methyl group. $R^5$'s are each independently an alkyl group having 1 to 5 carbon atoms, and h" is an integer of 1 to 4.

In general formulae (f4-1) and (f4-2), $R^c$'s are each independently a hydrogen atom or a methyl group.

In general formulae (f4-1) and (f4-2), $R^5$'s are each independently an alkyl group having 1 to 5 carbon atoms, and specifically, a lower linear or branched alkyl group such as a methyl group, an ethyl group, a propyl group, an isopropyl group, an n-butyl group, an isobutyl group, a tert-butyl group, a pentyl group, an isopentyl group, and a neopentyl group is preferable, and a methyl group and an ethyl group are further preferable.

In general formula (f4-1), h" is an integer of 1 to 4.

In a case where the (F1) component includes a structural unit (f4), the ratio of the structural unit (f4) is preferably 5 to 50 mol %, is further preferably 5 to 40 mol %, and is still further preferably 5 to 35 mol %, with respect to the total (100 mol %) of the entire structural units for constituting the (F1) component.

When the ratio of the structural unit (f4) is equal to or greater than the lower limit value of the above range, it is possible to promote the solubility in a developing solution in the exposed area. When the ratio of the structural unit (f4) is equal to or lower than the upper limit value of the above range, it is possible to take balance with other structural units.

The (F1) component is preferably a polymer (homopolymer) consisting of the structural unit (f1); a copolymer having the structural unit (f1) and the structural unit (f2); a copolymer having the structural unit (f1) and a structural unit (f3); or a copolymer having a structural unit (f1), a structural unit (f3), and a structural unit (f4), and further preferably a copolymer having the structural unit (f1) and the structural unit (f2) or a copolymer having the structural unit (f1) and the structural unit (f3).

The (F) component can be obtained by polymerizing a monomer that induces a desired structural unit by known radical polymerization or the like using a radical polymerization initiator such as azobisisobutyronitrile (AIBN) and dimethyl azobisisobutyrate.

The mass average molecular weight (Mw) (determined by gel permeation chromatography in terms of standard polystyrene) of the (F) component is preferably 1,000 to 50,000, is further preferably 5,000 to 40,000, and is most preferably 10,000 to 30,000. When the mass average molecular weight is equal to or less than the upper limit value of the above range, the solubility with respect to a resist solvent is sufficient in the case where the (F) component is used as a resist, and when the mass average molecular weight of the (F) component is equal to or greater than the lower limit value of the above range, dry etching resistance and a resist pattern cross-sectional shape are improved.

The dispersivity (Mw/Mn) of the (F) component is preferably 1.0 to 5.0, is further preferably 1.0 to 3.0, and is most preferably 1.2 to 2.5.

The (F) component may be used alone, or two or more kinds thereof may be used in combination.

The (F) component is preferably 0.1 to 20 parts by mass, is further preferably 0.5 to 10 parts by mass, and is still further preferably 1 to 5 parts by mass, with respect to 100 parts by mass of the (A) component. When the (F) component is equal to or greater than the lower limit value of the above range, in the forming of the resist pattern, the generation of the defects is suppressed. On the other hand, when the (F) component is equal to or lower than the upper limit value, the lithography properties are improved.

Acid Generator Component; (B) Component

The resist composition in the present embodiment may contain an acid generator component (B) (hereinafter referred to as "(B) component") which generates an acid upon exposure.

The (B) component is not particularly limited, and those which have been suggested as an acid generator for a chemically amplified resist can be used.

Examples of the acid generator include various kinds of acid generators such as an onium salt-based acid generator such as an iodonium salt and a sulfonium salt, an oxime sulfonate-based acid generator, diazomethane-based acid generators such as bisalkyl or bisarylsulfonyl diazomethanes and poly(bissulfonyl) diazomethane, a nitrobenzylsulfonate-based acid generator, an iminosulfonate-based acid generator, and a disulfone-based acid generator. Among them, an onium salt-based acid generator is preferably used.

Examples of the onium salt-based acid generator include a compound (hereinafter, referred to as "(b-1) component") represented by general formula (b-1), a compound (hereinafter, referred to as "(b-2) component") represented by general formula (b-2), and a compound (hereinafter, referred to as "(b-3) component") represented by general formula (b-3).

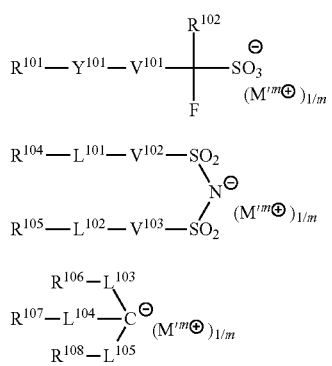

In the formulae, $R^{101}$, and $R^{104}$ to $R^{108}$ are each independently a cyclic group which may have a substituent, a chain alkyl group which may have a substituent, or a chain alkenyl group which may have a substituent. $R^{104}$ and $R^{105}$ may be bonded to each other so as to form a ring. Two of $R^{106}$ to $R^{108}$ may be bonded to each other so as to form a ring. $R^{102}$ is a fluorine atom or a fluorinated alkyl group having 1 to 5 carbon atoms. $Y^{101}$ is a divalent linking group containing a single bond or an oxygen atom. $V^{101}$ to $V^{103}$ are each independently a single bond, alkylene group, or a fluorinated alkylene group. $L^{101}$ and $L^{102}$ are each independently a single bond or an oxygen atom. $L^{103}$ to $L^{105}$ are each independently a single bond, —CO—, or —SO$_2$—. $M^{m+}$ is an m-valent organic cation.

Anion Part

Anion Part of (b-1) Component

In general formula (b-1), $R^{101}$ is a cyclic group which may have a substituent, a chain alkyl group which may have a substituent, or a chain alkenyl group which may have a substituent.

Cyclic Group which May have Substituent for $R^{101}$

The cyclic group is preferably a cyclic hydrocarbon group, and the cyclic hydrocarbon group may be an aromatic hydrocarbon group or an aliphatic hydrocarbon group.

Examples of the aromatic hydrocarbon group for $R^{101}$ include an aromatic hydrocarbon ring mentioned as a divalent aromatic hydrocarbon group for $Va^1$ in general formula (a1-1), or an aryl group obtained by removing one hydrogen atom from an aromatic compound containing two or more aromatic rings, and a phenyl group and a naphthyl group are preferable.

Examples of the cyclic aliphatic hydrocarbon group for $R^{101}$ include a group in which one hydrogen atom is removed from the monocycloalkane or polycycloalkane mentioned as the divalent aliphatic hydrocarbon group for $Va^1$ in general formula (a1-1), and an adamantyl group and a norbornyl group are preferable.

In addition, a cyclic hydrocarbon group for $R^{101}$ may contain a heteroatom like a hetero ring, and specific examples thereof include lactone-containing cyclic groups respectively represented by general formulae (a2-r-1) to (a2-r-7), —SO$_2$— containing cyclic groups respectively represented by general formulae (a5-r-1) to (a5-r-4), and heterocyclic groups respectively represented by general formulae (r-hr-1) to (r-hr-16).

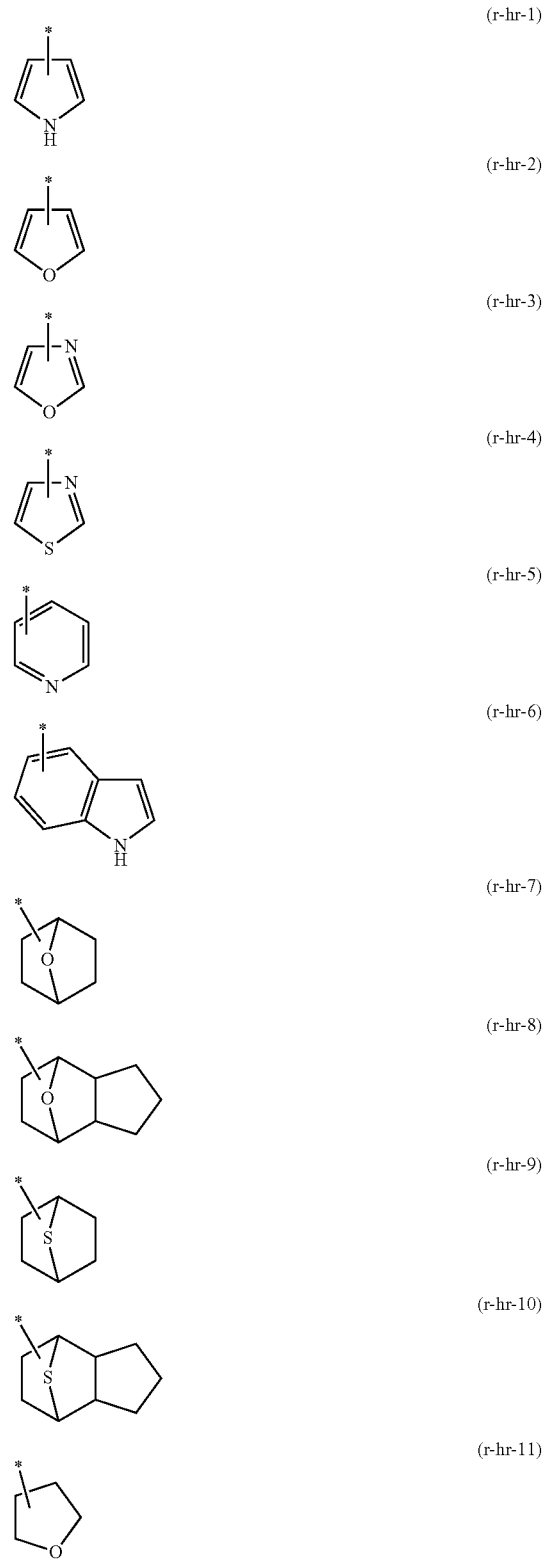

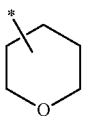 (r-hr-12)

 (r-hr-13)

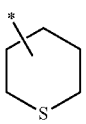 (r-hr-14)

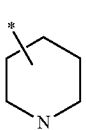 (r-hr-15)

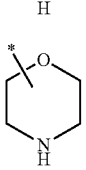 (r-hr-16)

Examples of the substituents in the cyclic hydrocarbon group for $R^{101}$ may have include an alkyl group, an alkoxy group, a halogen atom, a halogenated alkyl group, a hydroxyl group, a carbonyl group, and a nitro group.

The alkyl group as a substituent is preferably an alkyl group having 1 to 5 carbon atoms, and is most preferably a methyl group, an ethyl group, a propyl group, an n-butyl group, and a tert-butyl group.

The alkoxy group as a substituent is preferably an alkoxy group having 1 to 5 carbon atoms, is further preferably a methoxy group, an ethoxy group, an n-propoxy group, an iso-propoxy group, an n-butoxy group, and a tert-butoxy group, and is most preferably a methoxy group and an ethoxy group.

Examples of the halogen atom as a substituent include a fluorine atom, a chlorine atom, a bromine atom, and an iodine atom, and among them, the fluorine atom is preferable.

Examples of the halogenated alkyl group as a substituent include a group in which at least one hydrogen atom of an alkyl group having 1 to 5 carbon atoms such as a methyl group, an ethyl group, a propyl group, an n-butyl group, and a tert-butyl group is substituted with a halogen atom.

Chain Alkyl Group which May have a Substituent for $R^{101}$

The chain alkyl group which may have a substituent in $R^{101}$ may be linear or branched.

The number of carbon atoms of the linear alkyl group is preferably 1 to 20, is further preferably 1 to 15, and is most preferably 1 to 10. Specific examples thereof include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a heneicosyl group, and a docosyl group.

The number of carbon atoms of the branched alkyl group is preferably 3 to 20, is further preferably 3 to 15, and is most preferably 3 to 10. Specific examples include a 1-methyl-ethyl group, a 1-methylpropyl group, a 2-methylpropyl group, a 1-methylbutyl group, a2-methylbutyl group, a 3-methylbutyl group, a 1-ethylbutyl group, a2-ethylbutyl group, a 1-methylpentyl group, a 2-methylpentyl group, a 3-methylpentyl group, and a 4-methylpentyl group.

Chain Alkenyl Group which May have Substituent for $R^{101}$

A chain alkenyl group for $R^{101}$ may be a linear alkenyl group or a branched alkenyl group, and the number of carbon atoms of the chain-shaped alkenyl group for $R^{101}$ is preferably 2 to 10, is further preferably 2 to 5, and is further preferably 2 to 4, and is particularly preferably 3. Examples of the linear alkenyl group include a vinyl group, a propenyl group (allyl group), and a butynyl group. Examples of the branched alkenyl group include 1-methyl propenyl group, and 2-methyl propenyl group.

Among the chain alkenyl groups, a propenyl group is particularly preferable.

Examples of the substituent in the chain alkyl group or alkenyl group for $R^{101}$ include an alkoxy group, a halogen atom, a halogenated alkyl group, a hydroxyl group, a carbonyl group, a nitro group, an amino group, and a cyclic group for $R^{101}$.

Among them, $R^{101}$ is preferably a cyclic group which may have a substituent, and is further preferably a cyclic hydrocarbon group which may have a substituent. More specifically, a group obtained by removing one or more hydrogen atoms from a phenyl group, a naphthyl group, and a polycycloalkane, a lactone-containing cyclic group represented by each of general formulae (a2-r-1) to (a2-r-7), and an —$SO_2$— containing cyclic group represented by each of general formulae (a5-r-1) to (a5-r-4).

In general formula (b-1), $Y^{101}$ is a divalent linking group containing a single bond or an oxygen atom.

In the case where $Y^{101}$ is a divalent linking group containing an oxygen atom, $Y^{101}$ may contain atoms other than the oxygen atom. Examples of the atoms other than the oxygen atom include a carbon atom, a hydrogen atom, a sulfur atom, and a nitrogen atom.

Examples of the divalent linking group containing an oxygen atom include a non-hydrocarbon-based oxygen atom-containing linking group such as an oxygen atom (ether bond:—O—), an ester bond (—C(=O)—O—), an oxycarbonyl group (—O—C(=O)—), an amide bond (—C(=O)—NH—), a carbonyl group (—C(=O)—), and a carbonate bond (—O—C(=O)—O—); and a combination of the a non-hydrocarbon-based oxygen atom-containing linking group with an alkylene group. A sulfonyl group (—$SO_2$—) may be further linked to the above combination. Examples of the divalent linking group containing an oxygen atom include linking groups respectively represented by general formulae (y-al-1) to (y-al-7).

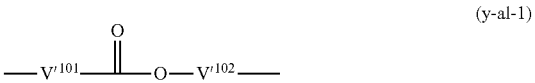 (y-al-1)

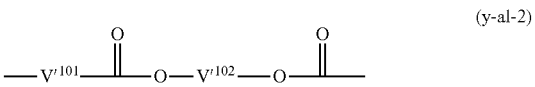 (y-al-2)

-continued

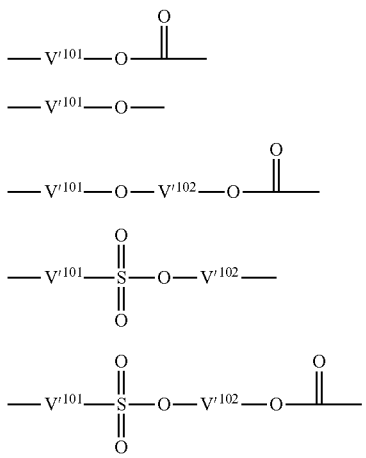

(y-a1-3)
(y-a1-4)
(y-a1-5)
(y-a1-6)
(y-a1-7)

In the formulae, V'$^{101}$ is a single bond or an alkylene group having 1 to 5 carbon atoms, and V'$^{102}$ is a divalent saturated hydrocarbon group having 1 to 30 carbon atoms.

The divalent saturated hydrocarbon group for V'$^{102}$ is preferably an alkylene group having 1 to 30 carbon atoms.

The alkylene group for V'$^{101}$ and V'$^{102}$ may be a linear alkylene group or a branched alkylene group, and is preferably a linear alkylene group.

Specific examples of the alkylene group for V'$^{101}$ and V'$^{102}$ include a methylene group [—$CH_2$—]; an alkyl methylene group such as —$CH(CH_3)$—, —$CH(CH_2CH_3)$ ($CH_3$)—$C(CH_3)$ ($CH_2CH_3)$—$C(CH_3)$ ($CH_2CH_2CH_3)$—, and —$C(CH_2CH_3)_2$—; an ethylene group [—$CH_2CH_2$—]; an alkyl ethylene group such as —$CH(CH_3)$ $CH_2$—, —CH ($CH_3$) $CH(CH_3)$—$C(CH_3)_2CH_2$—, and —$CH(CH_2CH_3)$ $CH_2$—; a trimethylene group (an n-propylene group) [—$CH_2CH_2CH_2$—]; alkyl trimethylene group such as —CH ($CH_3$) $CH_2CH_2$—, and —$CH_2CH(CH_3)$ $CH_2$—; a tetramethylene group [—$CH_2CH_2CH_2CH_2$—]; an alkyl tetramethylene group such as —$CH(CH_3)$ $CH_2CH_2CH_2$— and —$CH_2CH(CH_3)$ $CH_2CH_2$—; and a pentamethylene group [—$CH_2CH_2CH_2CH_2CH_2$—].

Further, a portion of methylene groups in the alkylene group for V'$^{101}$ or V'$^{102}$ may be substituted with a divalent aliphatic cyclic group having 5 to 10 carbon atoms. The aliphatic cyclic group is preferably a divalent group obtained by further removing one hydrogen atom from a cyclic aliphatic hydrocarbon group for Ra'$^{3}$ in general formula (a1-r-1), and is further preferably a cyclohexylene group, a 1,5-adamantylene group, or a 2,6-adamantylene group.

As Y$^{101}$, a divalent linking group containing an ester bond or an ether bond is preferable, and linking groups respectively represented by general formulae (y-a1-1) to (y-a1-5) are further preferable.

In general formula (b-1), V$^{101}$ is a single bond, an alkylene group, or a fluorinated alkylene group. The number of carbon atoms of the alkylene group and the fluorinated alkylene group for V$^{101}$ is preferably 1 to 4. Examples of the fluorinated alkylene group for V$^{101}$ include a group in which at least one of the hydrogen atoms of the alkylene group for V$^{101}$ is substituted with a fluorine atom. Among them, V$^{101}$ is preferably a single bond, or a fluorinated alkylene group having 1 to 4 carbon atoms.

In general formula (b-1), R$^{102}$ is a fluorine atom, or a fluorinated alkyl group having 1 to 5 carbon atoms. R$^{102}$ is preferably a fluorine atom, or a perfluoroalkyl group having 1 to 5 carbon atoms, and is further preferably a fluorine atom.

Specific examples of the anion part of the (b-1) component include a fluorinated alkyl sulfonate anion such as trifluoromethanesulfonate anion and perfluorobutanesulfonate anion in the case where Y$^{101}$ is a single bond; and the anion represented by any one of general formulae (an-1) to (an-3) in the case where Y$^{101}$ is a divalent linking group containing an oxygen atom.

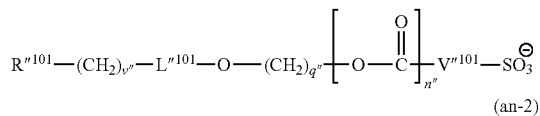

(an-1)

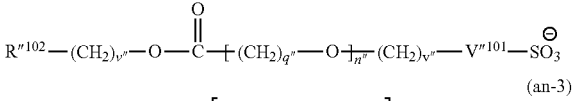

(an-2)

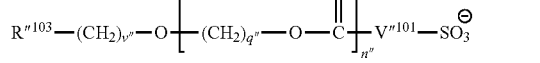

(an-3)

In the formulae, R'''$^{101}$ is an aliphatic cyclic group which may have a substituent, groups respectively represented by formulae (r-hr-1) to (r-hr-6), or a chain alkyl group which may have a substituent; R'''$^{102}$ is an aliphatic cyclic group which may have a substituent, a lactone-containing cyclic group represented by general formulae (a2-r-1) to (a2-r-7), or a —$SO_2$— containing cyclic group represented by general formulae (a5-r-1) to (a5-r-4); R'''$^{103}$ is an aromatic cyclic group which may have a substituent, an aliphatic cyclic group which may have a substituent, or a chain alkenyl group which may have a substituent; V'''$^{101}$ is a fluorinated alkylene group; L'''$^{101}$ is —C(=O)— or —$SO_2$—; v'''s are each independently an integer of 0 to 3, q'''s are each independently an integer of 1 to 20, and n'' is 0 or 1.

The aliphatic cyclic group which may have a substituent for R'''$^{101}$, R'''$^{102}$, and R'''$^{103}$ is preferably a group exemplified as a cyclic aliphatic hydrocarbon group for R$^{101}$. Examples of the substituents include the same substituents as those with which the cyclic aliphatic hydrocarbon group for R$^{101}$ may be substituted.

The aromatic cyclic group which may have a substituent for R'''$^{103}$ is preferably a group exemplified as an aromatic hydrocarbon group of a cyclic hydrocarbon group for R$^{101}$. Examples of the substituents include the same substituents as those with which an aromatic hydrocarbon group for R$^{101}$ may be substituted.

The chain alkyl group which may have a substituent for R'''$^{101}$ is preferably a group exemplified as a chain alkyl group for R$^{101}$. The chain alkenyl group which may have a substituent for R'''$^{103}$ is preferably a group exemplified as a chain alkenyl group for R$^{101}$. V'''$^{101}$ is preferably a fluorinated alkylene group having 1 to 3 carbon atoms, and is particularly preferably —$CF_2$—, —$CF_2CF_2$—, —$CHFCF_2$—, —$CF(CF_3)CF_2$—, and —$CH(CF_3)$ $CF_2$—.

Anion Part of (b-2) Component

In general formula (b-2), R$^{104}$ and R$^{105}$ each independently represent a cyclic group which may have a substituent, a chain alkyl group which may have a substituent, or a chain alkenyl group which may have a substituent, which are the same as those for $R^{101}$ in general formula (b-1). Here, $R^{104}$ and $R^{105}$ may be bonded to each other so as to form a ring.

$R^{104}$ and $R^{105}$ are preferably a chain alkyl group which may have a substituent, and are further preferably a linear or branched alkyl group, or a linear or branched fluorinated alkyl group.

The number of the carbon atoms of the chain alkyl group is preferably 1 to 10, is further preferably 1 to 7, and is still further preferably 1 to 3. The number of the carbon atoms of the chain alkyl group for $R^{104}$ and $R^{105}$ is preferably as small as possible within the range of the carbon number from the aspect that the solubility with respect to the resist solvent is improved. In the chain alkyl group for $R^{104}$ and $R^{105}$, a large number of the hydrogen atoms which are substituted with a fluorine atom is preferable from the aspect that the strength of the acid becomes stronger and transparency to high energy light of 200 nm or less or electron beam is improved. The ratio of a fluorine atom in the chain alkyl group, that is, the fluorination rate is preferably 70% to 100%, and is further preferably 90% to 100%, and a perfluoroalkyl group in which all hydrogen atoms are substituted with fluorine atoms is most preferable.

In general formula (b-2), $V^{102}$ and $V^{103}$ each independently represent a single bond, an alkylene group, or a fluorinated alkylene group, which are the same as those for $V^{101}$ in general formula (b-1).

In general formula (b-2), $L^{101}$ and $L^{102}$ each independently represent a single bond or an oxygen atom.

Anion Part of (b-3) Component

In general formula (b-3), $R^{106}$ to $R^{108}$ each independently represent a cyclic group which may have a substituent, a chain alkyl group which may have a substituent, or a chain alkenyl group which may have a substituent, which are the same as those for $R^{101}$ in general formula (b-1).

$L^{103}$ to $L^{105}$ each independently represent a single bond, —CO—, or —$SO_2$—.

Cation Part

In general formulae (b-1), (b-2), and (b-3), $M^{m+}$ is an m-valent organic cation, and among them, a sulfonium cation and an iodonium cation are preferable, and cations represented by general formulae (ca-1) to (ca-4) are particularly preferable.

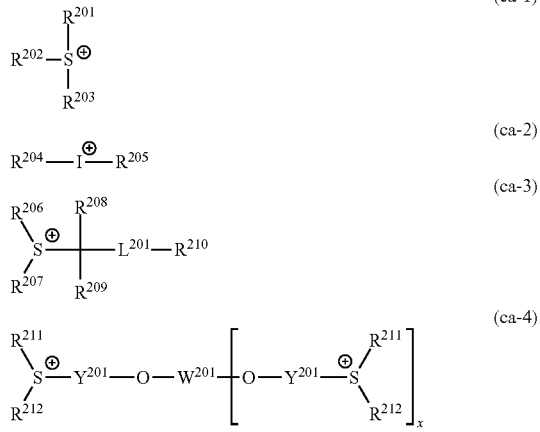

In the formula, $R^{201}$ to $R^{207}$, and $R^{211}$ to $R^{212}$ each independently represent an aryl group which may have a substituent, an alkyl group, or an alkenyl group, $R^{201}$ to $R^{203}$, $R^{206}$ to $R^{207}$, and $R^{211}$ to $R^{212}$ may be bonded to each other so as to form a ring together with a sulfur atom in the formula. $R^{208}$ to $R^{209}$ each independently represent a hydrogen atom or an alkyl group having 1 to 5 carbon atoms, $R^{210}$ represents an aryl group which may have a substituent, an alkyl group, an alkenyl group, or an —$SO_2$— containing cyclic group, $L^{201}$ represents —C(=O)— or each —C(=O)—O—, $Y^{201}$'s independently represent an arylene group, an alkylene group, or an alkenylene group. x is 1 or 2. $W^{201}$ represents a (x+1) valent linking group.

Examples of the aryl group for $R^{201}$ to $R^{207}$ and $R^{211}$ and $R^{212}$ include an unsubstituted aryl group having 6 to 20 carbon atoms, and a phenyl group and a naphthyl group are preferable.

As the alkyl group for $R^{201}$ to $R^{207}$ and $R^{211}$ and $R^{212}$, a chain or cyclic alkyl group having 1 to 30 carbon atoms is preferable.

As the alkenyl group for $R^{201}$ to $R^{207}$ and $R^{211}$ and $R^{212}$, an alkenyl group having 2 to 10 carbon atoms is preferable.

Examples of the substituents that $R^{201}$ to $R^{207}$ and $R^{210}$ to $R^{212}$ may have include an alkyl group, a halogen atom, a halogenated alkyl group, a carbonyl group, a cyano group, an amino group, an aryl group, an arylthio group, and the groups which are represented by general formulae (ca-r-1) to (ca-r-7).

The aryl group in the arylthio group as a substituent is the same as that for $R^{101}$, and specific examples thereof include a phenylthio group or a biphenylthio group.

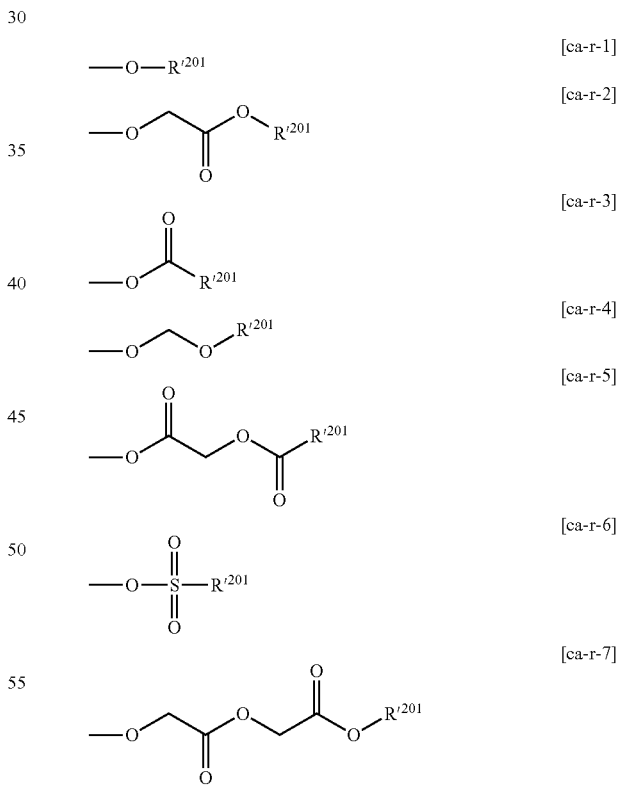

In the formulae, $R'^{201}$'s each independently represent a hydrogen atom, a cyclic group which may have a substituent, a chain alkyl group, or a chain alkenyl group.

Examples of the cyclic group which may have a substituent, the chain alkyl group which may have a substituent, or the chain alkenyl group which may have a substituent for $R'^{201}$ include the same groups for $R^{101}$ in general formula (b-1), and examples of the cyclic group which may have a substituent or the chain alkyl group which may have a substituent also include the same group as those for an acid dissociable group represented by formula (a1-r-2).

In the case where $R^{201}$ to $R^{203}$, $R^{206}$ and $R^{207}$, $R^{211}$ and $R^{212}$ are bonded to each other so as to form a ring together with a sulfur atom in each formula, the bonding may be performed via a heteroatom such as a sulfur atom, an oxygen atom, and a nitrogen atom, or a functional group such as a carbonyl group, —SO—, —SO$_2$—, —SO$_3$—, —COO—, —CONH— and —N(R$_N$)— (R$_N$ is an alkyl group having 1 to 5 carbon atoms). As a ring to be formed, a ring including a sulfur atom in the formula in the ring skeleton is preferably 3- to 10-membered rings including a sulfur atom, and is particularly preferably 5- to 7-membered rings including a sulfur atom. Specific examples of rings to be formed include a thiophene ring, a thiazole ring, a benzothiophene ring, a thianthrene ring, a benzothiophene ring, a dibenzothiophene ring, a 9H-thioxanthene ring, a thioxanthone ring, a thianthrene ring, a phenoxathiin ring, a tetrahydrothiophenium ring, and a tetrahydrothiopyranium ring.

$R^{208}$ and $R^{209}$ each independently represent a hydrogen atom or an alkyl group having 1 to 5 carbon atoms, and a hydrogen atom or an alkyl group having 1 to 3 carbon atoms is preferable, and in the case of the alkyl group, the alkyl groups may be bonded to each other so as to form a ring.

$R^{210}$ is an aryl group which may have a substituent, an alkyl group which may have a substituent, an alkenyl group which may have a substituent, or a —SO$_2$— containing cyclic group which may have a substituent.

Examples of the aryl group for $R^{210}$ include an unsubstituted aryl group having 6 to 20 carbon atoms, and a phenyl group and a naphthyl group are preferable.

The alkyl group for $R^{210}$ is a chain or cyclic alkyl group, and preferably has 1 to 30 carbon atoms.

The alkenyl group for $R^{210}$ preferably has 2 to 10 carbon atoms.

Examples of the —SO$_2$— containing cyclic group which may have a substituent for $R^{210}$ include the same groups as the "—SO$_2$-containing cyclic group", and a group represented by general formula (a5-r-1) is preferable.

$Y^{201}$'s each independently represent an arylene group, an alkylene group, or an alkenylene group.

Examples of the arylene group for $Y^{201}$ include a group obtained by removing one hydrogen atom from the aryl group exemplified as an aromatic hydrocarbon group for $R^{101}$ in general formula (b-1).

Examples of the alkylene group and the alkenylene group in $Y^{201}$ include the same as the aliphatic hydrocarbon group as a divalent hydrocarbon group for Va$^1$ in general formula (a1-1).

In general formula (ca-4), x is 1 or 2.

$W^{201}$ is (x+1) valent, that is, a divalent or trivalent linking group.

The divalent linking group in $W^{201}$ is preferably a divalent hydrocarbon group which may have a substituent, which is the same as those for Ya$^{21}$ in general formula (a2-1). The divalent linking group in $W^{201}$ may be linear, branched, or cyclic, and is preferably cyclic. Among them, a group in which two carbonyl groups are bonded at both ends of the arylene group is preferable. Examples of the arylene group include a phenylene group and a naphthylene group, and the phenylene group is particularly preferable.

Examples of the trivalent linking group for $W^{201}$ include a group obtained by removing one hydrogen atom from the divalent linking group for $W^{201}$ and a group to which the divalent linking group is further bonded to the divalent linking group. The trivalent linking group for $W^{201}$ is preferably a group in which two carbonyl groups are bonded to the arylene group.

Preferred examples of cation represented by general formula (ca-1) include cations represented by general formulae (ca-1-1) to (ca-1-63).

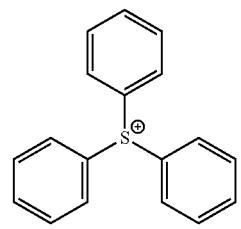
(ca-1-1)

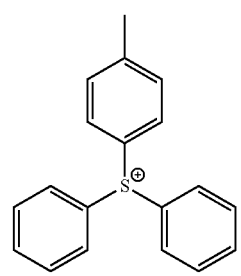
(ca-1-2)

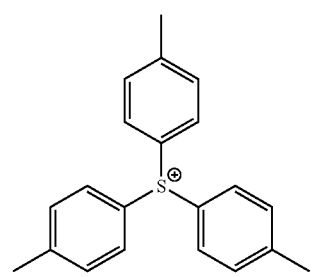
(ca-1-3)

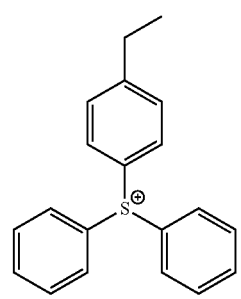
(ca-1-4)

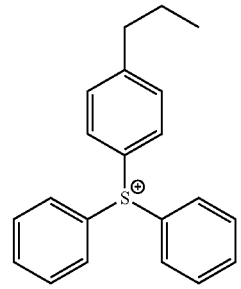
(ca-1-5)

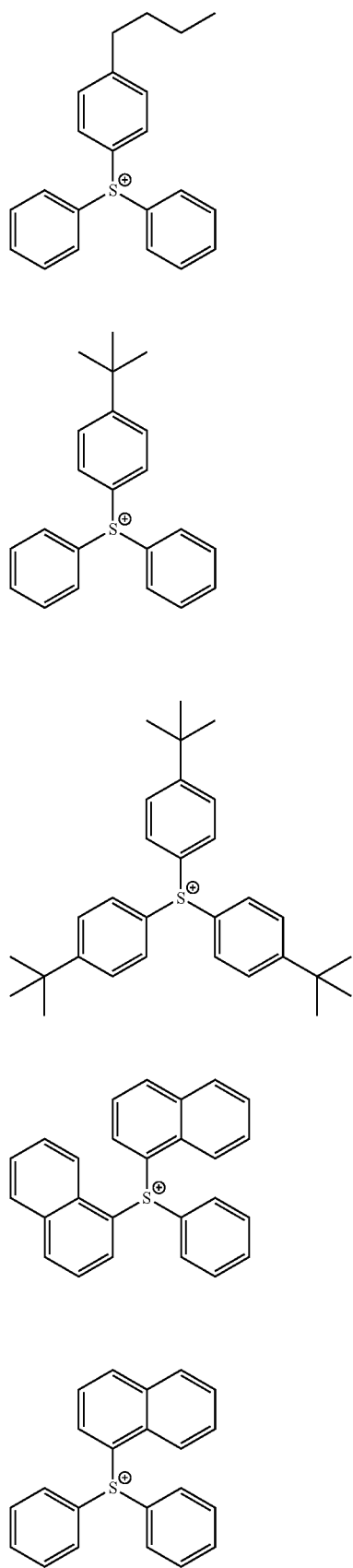
(ca-1-6)
(ca-1-7)
(ca-1-8)
(ca-1-9)
(ca-1-10)
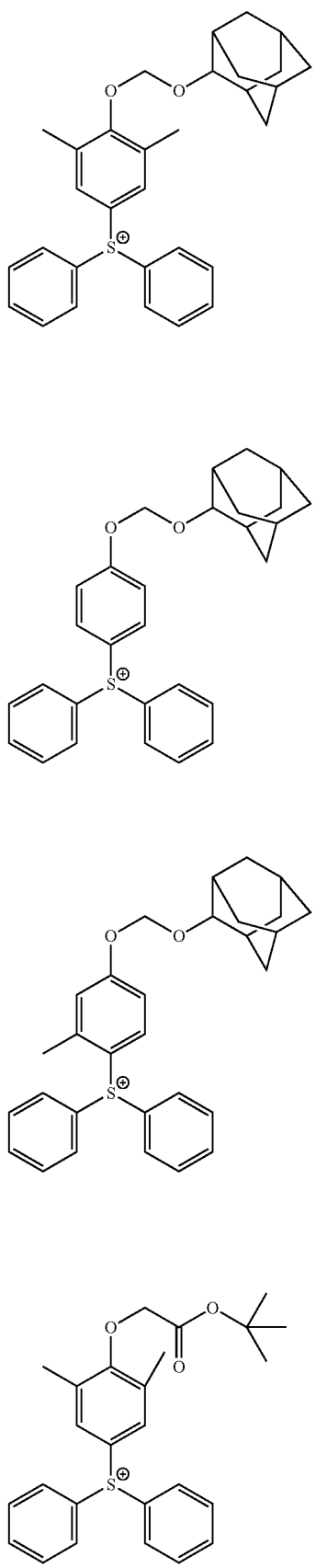
(ca-1-11)
(ca-1-12)
(ca-1-13)
(ca-1-14)

(ca-1-15)
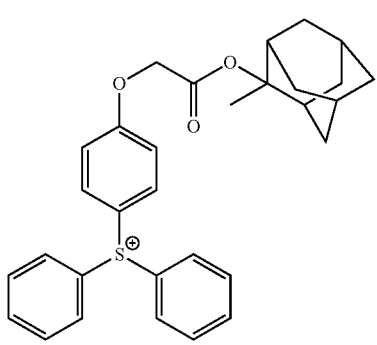
(ca-1-16)
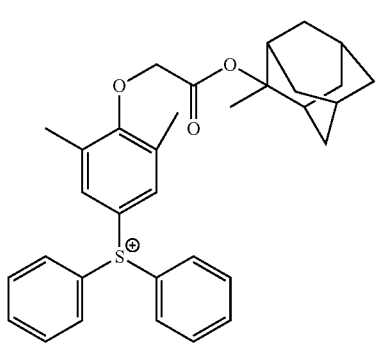
(ca-1-17)
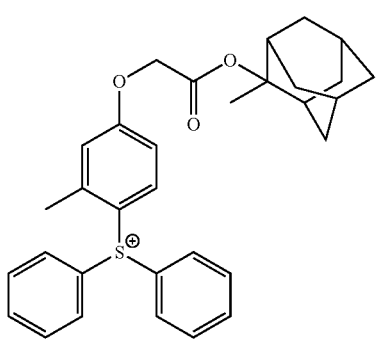
(ca-1-18)
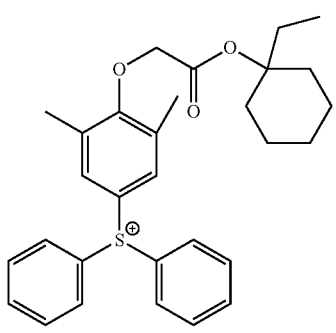
(ca-1-19)
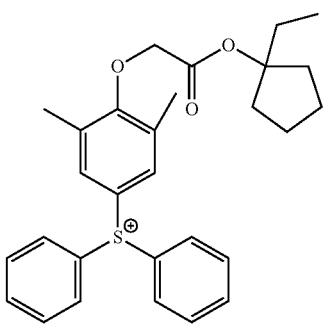
(ca-1-20)
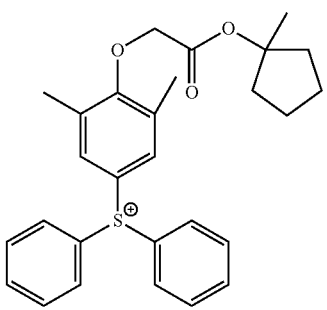
(ca-1-21)
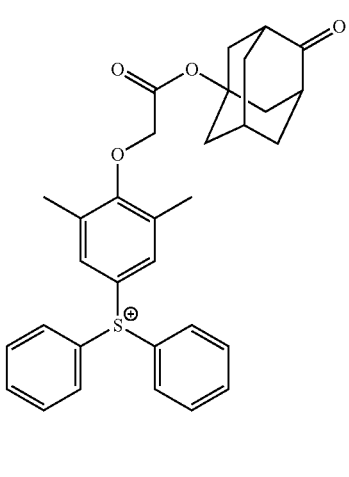
(ca-1-22)
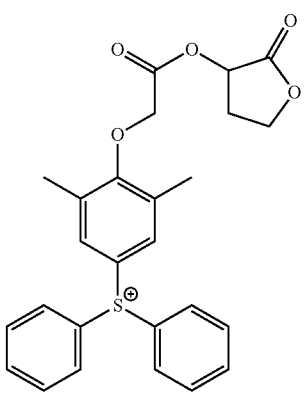

(ca-1-23)
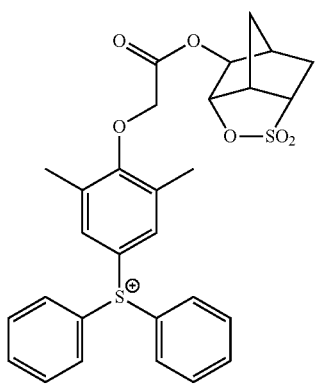
(ca-1-24)
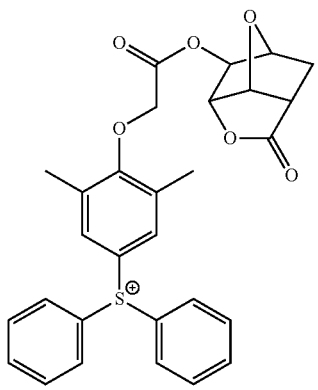
(ca-1-25)
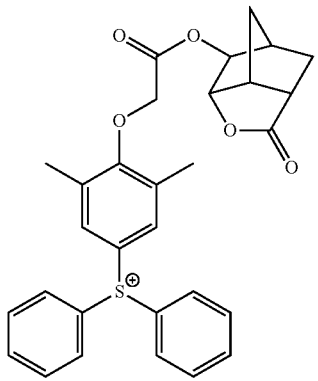
(ca-1-26)
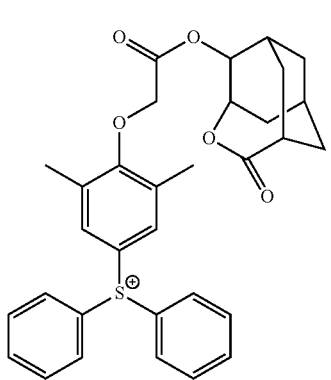
(ca-1-27)
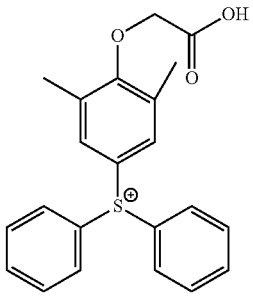
(ca-1-28)
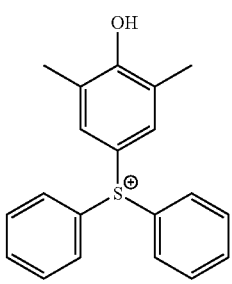
(ca-1-29)
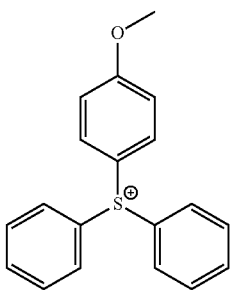
(ca-1-30)
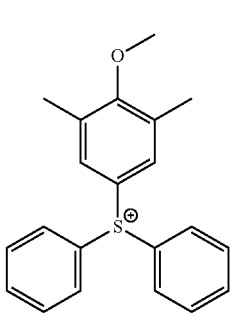
(ca-1-31)
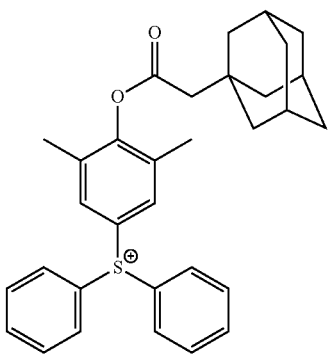

(ca-1-32)
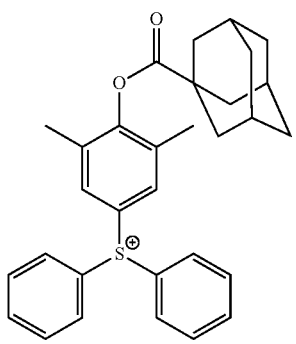
(ca-1-33)
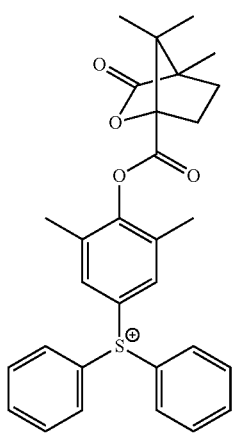
(ca-1-34)
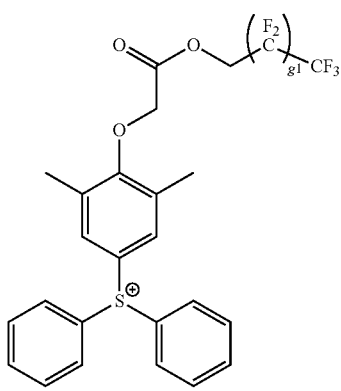
(ca-1-35)
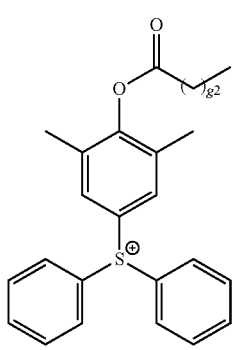
(ca-1-36)
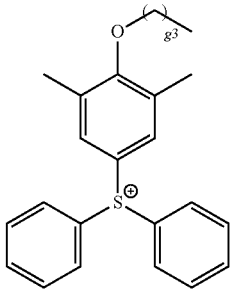
(ca-1-37)
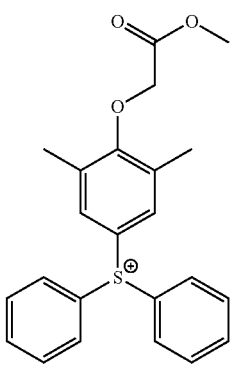
(ca-1-38)
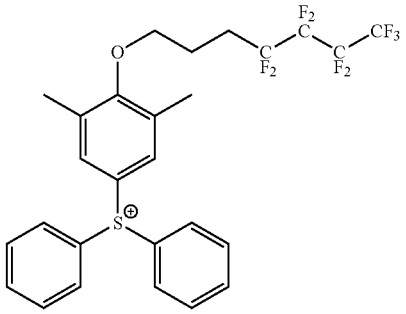
(ca-1-39)
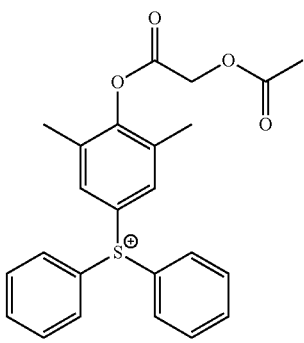

(ca-1-40)
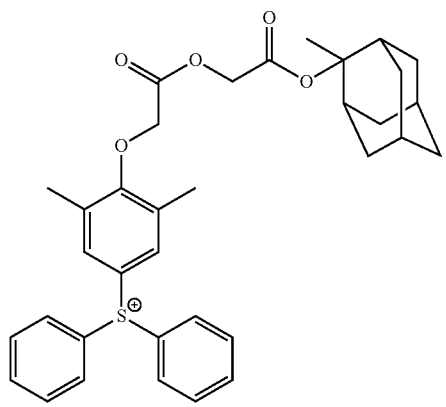
(ca-1-41)
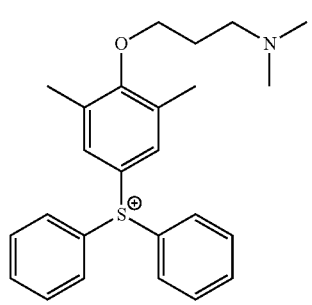
(ca-1-42)
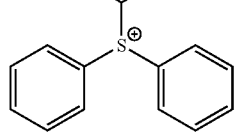
(ca-1-43)
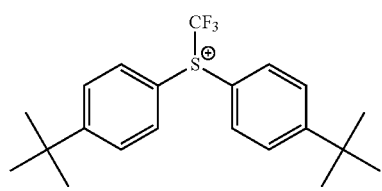
(ca-1-44)
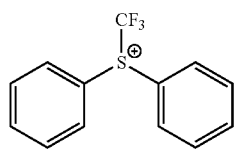
(ca-1-45)
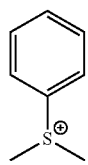
(ca-1-46)
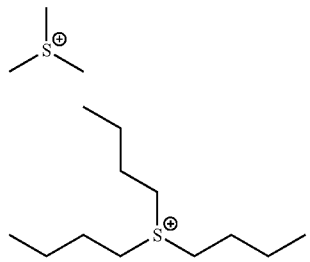
(ca-1-47)
(ca-1-48)
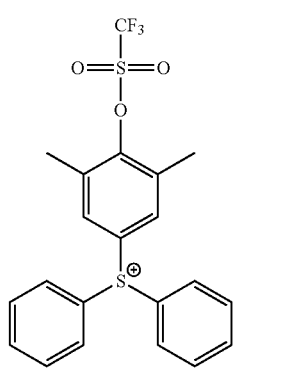
In the formula, g1, g2, and g3 represent repeated numbers; g1 is an integer of 1 to 5, g2 is an integer of 0 to 20, and g3 is an integer of 0 to 20.
(ca-1-49)
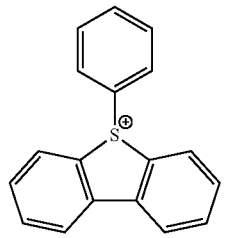
(ca-1-50)
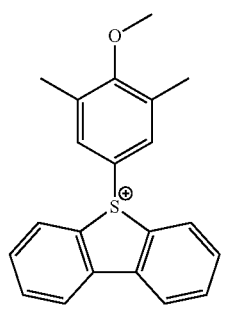
(ca-1-51)
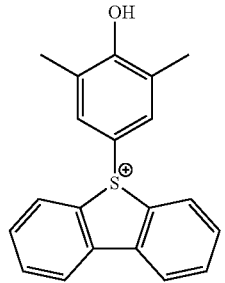

(ca-1-52)
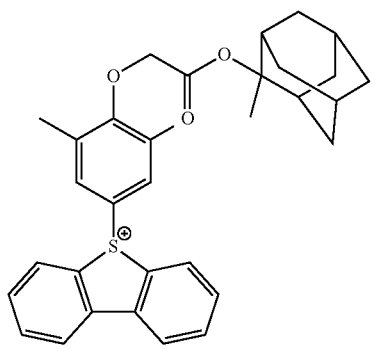
(ca-1-53)
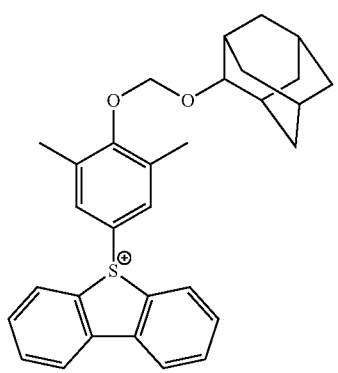
(ca-1-54)
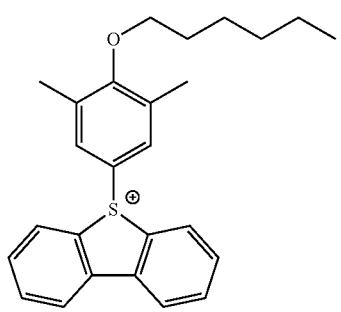
(ca-1-55)
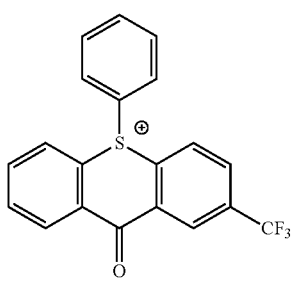
(ca-1-56)
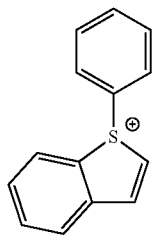
(ca-1-57)
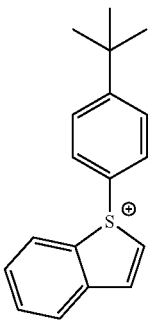
(ca-1-58)
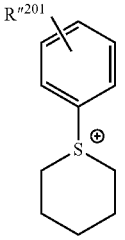
(ca-1-59)
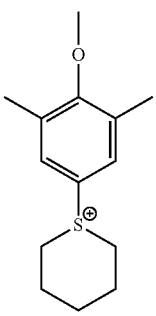
(ca-1-60)
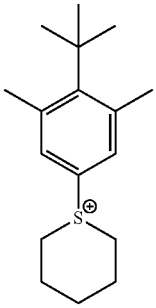
(ca-1-61)
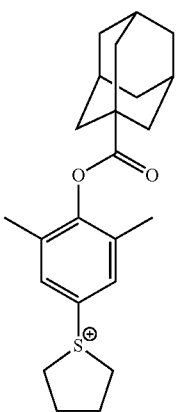

(ca-1-62)

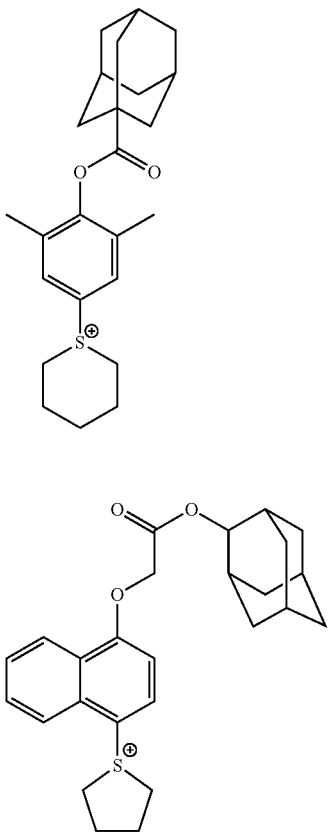

(ca-3-4)

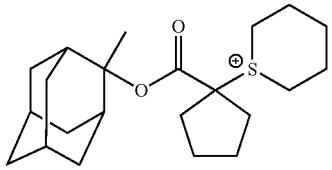

(ca-3-5)

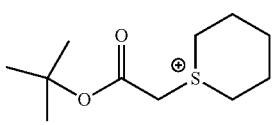

(ca-3-6)

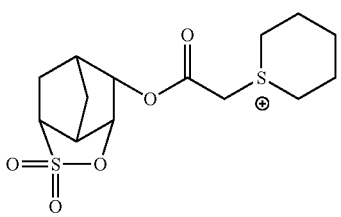

(ca-1-63)

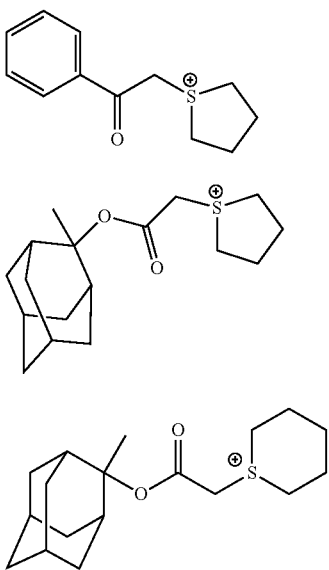

In the formula, $R''^{201}$ is a hydrogen atom or a substituent, and the substituent is the same as a substituent that which $R^{201}$ to $R^{207}$ and $R^{210}$ to $R^{212}$ may have.

Specifically, examples of the preferred cation represented by general formula (ca-3) include cations represented by general formulae (ca-3-1) to (ca-3-6).

(ca-3-1)

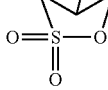

Specifically, examples of the preferred cation represented by general formula (ca-4) include cations represented by general formulae (ca-4-1) and (ca-4-2).

(ca-4-1)

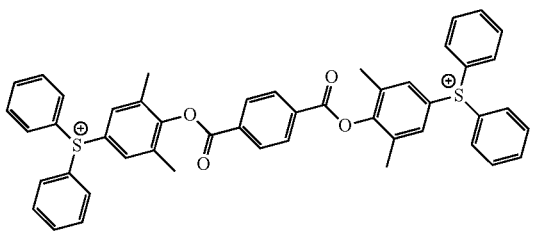

(ca-4-2)

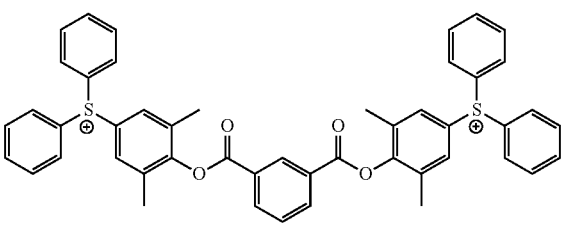

In the (B) component, the acid generator may be used alone, or two or more kinds thereof may be used in combination.

In the present embodiment, in a case where a resist composition contains the (B) component, the content of the (B) component is preferably 0.5 to 60 parts by mass, is further preferably 1 to 50 parts by mass, and is still further preferably 1 to 40 parts by mass, with respect to 100 parts by mass of the (A) component.

When the content of the (B) component is set in the range, it is sufficient to form a pattern. In addition, when the respective components of the resist composition are dissolved in an organic solvent, it is easy to obtain a uniform solution, and the storage stability is improved, and thus the content is preferably within the range.

Other Components

The resist composition of the present embodiment may further contain other components in addition to the (A) component, or the (A) component and the (B) component.

Examples of other components include a (D) component, an (E) component, an (F) component, and an (S) component as described below.

(D) Component:

The resist composition of the present embodiment may contain an acid diffusion controlling agent component (hereinafter, referred to as "(D) component").

The (D) component functions as a quencher (acid diffusion control agent) that traps an acid generated upon exposure from the (B) component or the like.

The (D) component of the present embodiment may be a photodegradable base (D1) (hereinafter, referred to as "(D1) component) which is decomposed upon exposure to lose acid diffusion controllability, or may be a nitrogen-containing organic compound (D2) (hereinafter, referred to as "(D2) component) which does not correspond to the (D1) component.

(D1) Component

With the resist composition containing the (D1) component, it is possible to further improve the contrast between the exposed area and the unexposed area at the time of forming the resist pattern.

The (D1) component is not particularly limited as long as the component which is decomposed upon exposure to lose acid diffusion controllability, and preferred examples thereof include one or more compounds selected from the group consisting of a compound (hereinafter, referred to as "(d1-1) component") represented by general formula (d1-1), a compound (hereinafter, referred to as "(d1-2) component") represented by general formula (d1-2), and a compound (hereinafter, referred to as "(d1-3) component") represented by general formula (d1-3).

Since the (d1-1) to (d1-3) components are decomposed in the exposed area of the resist film, the acid diffusion controllabilities (basicity) are lost. For this reason, the (d1-1) to (d1-3) components do not act as a quencher in the exposed area, but act as a quencher in the unexposed area of the resist film.

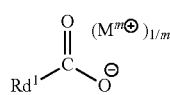

(d1-1)

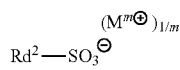

(d1-2)

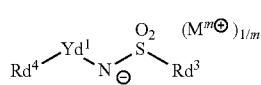

(d1-3)

In the formulae, $Rd^1$ to $Rd^4$ are a cyclic group which may have a substituent, a chain alkyl group which may have a substituent, or a chain alkenyl group which may have a substituent, provided that a fluorine atom is not bonded to the carbon atom adjacent to S atom in $Rd^2$ in general formula (d1-2). $Yd^1$ is a single bond or a divalent linking group. $M^{m+}$'s each independently represent an m-valent organic cation.

(d1-1) Component

Anion Part

In general formula (d1-1), $Rd^1$ is a cyclic group which may have a substituent, a chain alkyl group which may have a substituent, or a chain alkenyl group which may have a substituent, and examples thereof include the same group as that of the $R^{101}$.

Among them, as $Rd^1$, an aromatic hydrocarbon group which may have a substituent, an aliphatic cyclic group which may have a substituent, or a chain hydrocarbon group which may have include a substituent are preferable. Preferred examples of the substituent that the above groups may have include a hydroxyl group, a fluorine atom, and a fluorinated alkyl group.

The aromatic hydrocarbon group is further preferably a phenyl group or a naphthyl group.

As the aliphatic cyclic group, a group obtained by removing one or more hydrogen atoms from polycycloalkane such as adamantane, norbornane, isobornane, tricyclodecane, and tetracyclododecane is preferable.

The chain hydrocarbon group is preferably a chain alkyl group. The number of carbon atoms of a chain alkyl group is preferably 1 to 10, and specific examples include a linear alkyl group such as a methyl group, an ethyl group, a propyl group, a butyl group, a pentyl group, a hexyl group, a heptyl group, an octyl group, a nonyl group, and a decyl group; and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a2-ethylbutyl group, a 1-methylpentyl group, a 2-methylpentyl group, a 3-methylpentyl group, and a 4-methylpentyl group.

In the case where the linear alkyl group is a fluorinated alkyl group having a fluorine atom or a fluorinated alkyl group as a substituent, the number of carbon atoms of the fluorinated alkyl group is preferably 1 to 11, is further preferably 1 to 8, and is still further preferably 1 to 4. The fluorinated alkyl group may contain other atoms in addition to the fluorine atom. Examples of other atoms in addition to the fluorine atom include an oxygen atom, a carbon atom, a hydrogen atom, a sulfur atom, and a nitrogen atom.

$Rd^1$ is preferably a fluorinated alkyl group in which at least one hydrogen atom of a linear alkyl group is substituted with a fluorine atom, and is further preferably a fluorinated alkyl group (a linear perfluoroalkyl group) in which all of the hydrogen atoms of a linear alkyl group are substituted with a fluorine atom.

Hereinafter, preferred examples of the anion part of the (d1-1) component are specifically described.

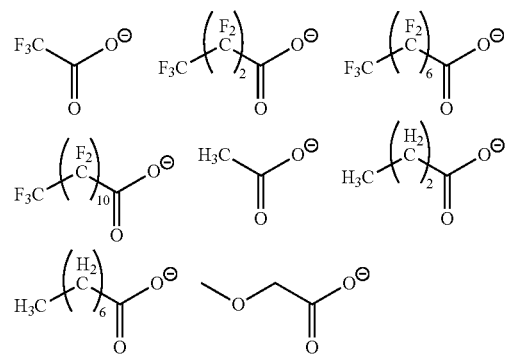

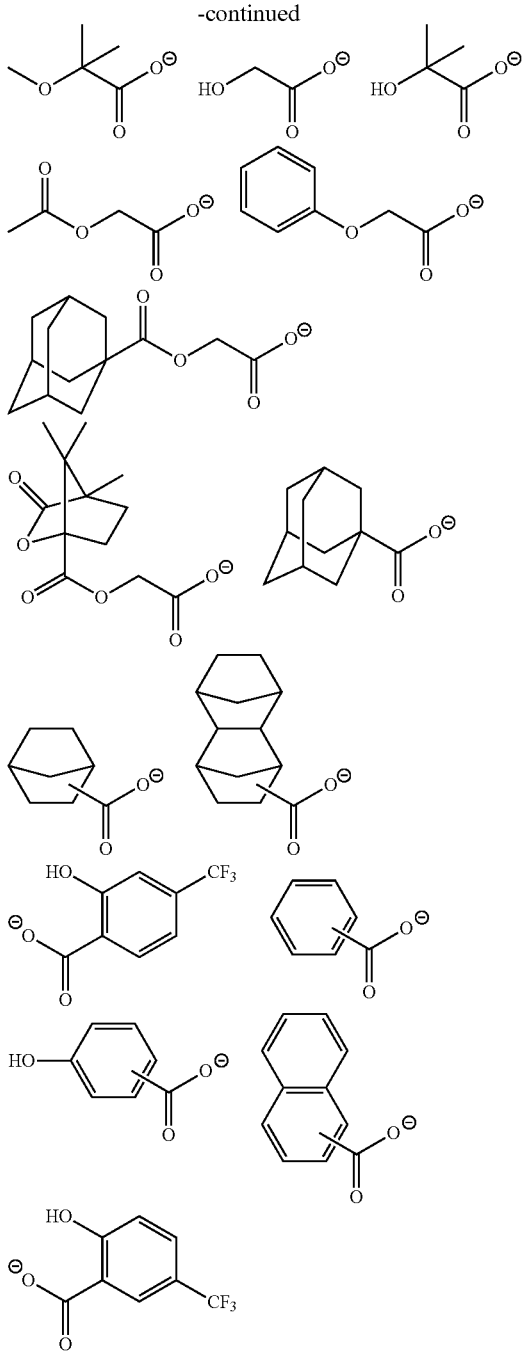

Cation Part

In general formula (d1-1), $M^{m+}$ is an m-valent organic cation.

The organic cation of $M^{m+}$ is not particularly limited, and examples thereof include the same cations as those respectively represented by general formulae (ca-1) to (ca-4), and the cations respectively represented by general formulae (ca-1-1) to (ca-1-63) are preferable.

The (d1-1) component may be used alone, or two or more kinds thereof may be used in combination.

(d1-2) Component
Anion Part

In general formula (d1-2), $Rd^2$ is a cyclic group which may have a substituent, a chain alkyl group which may have a substituent, or a chain alkenyl group which may have a substituent, and examples thereof include the same groups as those for $R^{101}$.

Here, a fluorine atom is not bonded to the carbon atom adjacent to S atom in $Rd^2$ (the carbon atom is not fluorine-substituted). With this, the anion of the (d1-2) component becomes an appropriately weak acid anion, and thus the quenching ability as the (D) component is improved.

$Rd^2$ is preferably an aliphatic cyclic group which may have a substituent. As the aliphatic cyclic group, a group (which may have a substituent) obtained by removing one or more hydrogen atoms from adamantane, norbornane, isobornane, tricyclodecane, or tetracyclododecane, and a group obtained by removing one or more hydrogen atoms from the camphor is preferable.

The hydrocarbon group for $Rd^2$ may have a substituent, and examples of the substituent include a substituent which is the same as the substituent which may be contained in the hydrocarbon group (an aromatic hydrocarbon group, and an aliphatic hydrocarbon group) for $Rd^1$ in general formula (d1-1).

Preferred examples of the anion part of the (d1-2) component are described as follows.

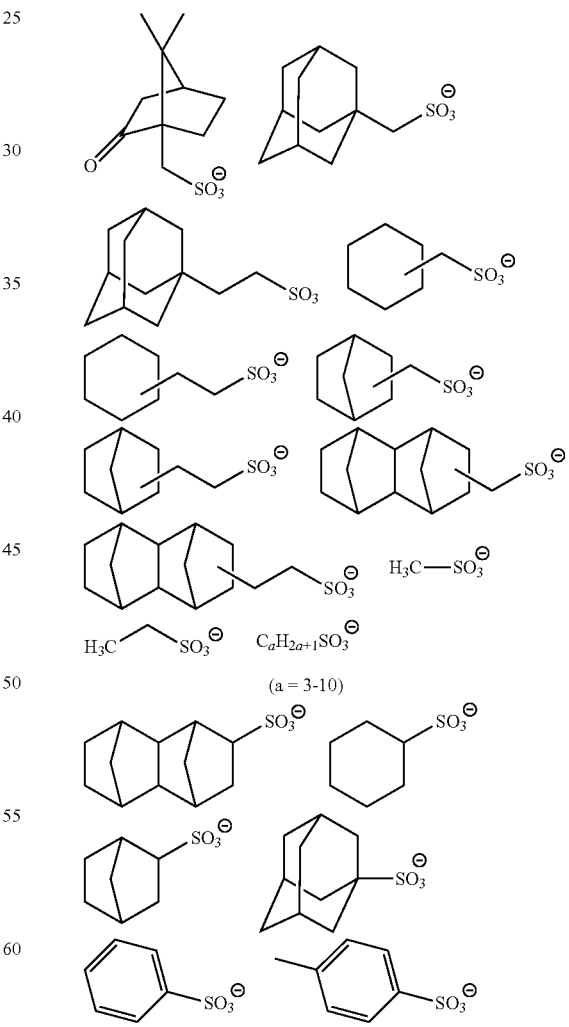

Cation Part

In general formula (d1-2), $M^{m+}$ is an m-valent organic cation, and is the same as $M^{m+}$ in general formula (d1-1).

The (d1-2) component may be used alone, or two or more kinds thereof may be used in combination.

(d1-3) Component
Anion Part

In general formula (d1-3), $Rd^3$ is a cyclic group which may have a substituent, a chain alkyl group which may have a substituent, or a chain alkenyl group which may have a substituent, and examples thereof include the same group as that for $R^{101}$, and a cyclic group containing a fluorine atom, a chain alkyl group, or a chain alkenyl group is preferable. Among them, the fluorinated alkyl group is preferable, and the same group as the fluorinated alkyl group for $Rd^1$ is further preferable.

In general formula (d1-3), $Rd^4$ is a cyclic group which may have a substituent, a chain alkyl group which may have a substituent, or a chain alkenyl group which may have a substituent, and examples thereof include the same group as that of $R^{101}$.

Among them, the alkyl group, the alkoxy group, the alkenyl group, and the cyclic group, which may have a substituent, are preferable.

The alkyl group for $Rd^4$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an iso-pentyl group, and a neopentyl group. At least one hydrogen atom in an alkyl group for $Rd^4$ may be substituted with a hydroxyl group, a cyano group, or the like.

The alkoxy group for $Rd^4$ is preferably an alkoxy group having 1 to 5 carbon atoms, and specific examples of the alkoxy group having 1 to 5 carbon atoms include a methoxy group, an ethoxy group, an n-propoxy group, an iso-propoxy group, an n-butoxy group, and a tert-butoxy group. Among them, the methoxy group and the ethoxy group are preferable.

Examples of the alkenyl group for $Rd^4$ include the same group as those for $R^{101}$, and a vinyl group, a propenyl group (an allyl group), a 1-methyl propenyl group, and a 2-methyl propenyl group are preferable. These groups may further have an alkyl group having 1 to 5 carbon atoms or a halogenated alkyl group having 1 to 5 carbon atoms as a substituent.

Examples of the cyclic group for $Rd^4$ include the same group as those for $R^{101}$, and an alicyclic group which is obtained by removing one or more hydrogen atoms from cycloalkane such as cyclopentane, cyclohexane, adamantane, norbornane, isobornane, tricyclodecane, and tetracyclododecane, or an aromatic group such as a phenyl group and a naphthyl group is preferable. In the case where $Rd^4$ is an alicyclic group, the resist composition is dissolved well in an organic solvent, and thus the lithography properties become excellent. Further, in the case where $Rd^4$ is an aromatic group, in the lithography in which EUV or the like is set as an exposure light source, the resist composition is excellent in the light absorption efficiency, and thus the sensitivity and the lithography properties become excellent.

In general formula (d1-3), $Yd^1$ is a single bond or a divalent linking group.

The divalent linking group for $Yd^1$ is not particularly limited, and examples thereof include a divalent hydrocarbon group which may have a substituent (an aliphatic hydrocarbon group and an aromatic hydrocarbon group), and a divalent linking group containing a heteroatom. The examples are the same as those exemplified in the description of the divalent linking group for $Ya^{21}$ in general formula (a2-1).

$Yd^1$ is preferably a carbonyl group, an ester bond, an amide bond, an alkylene group, or a combination thereof. The alkylene group is preferably a linear or branched alkylene group, and is further preferably a methylene group or an ethylene group.

Specific preferred examples of the anion part of the (d1-3) component are described as follows.

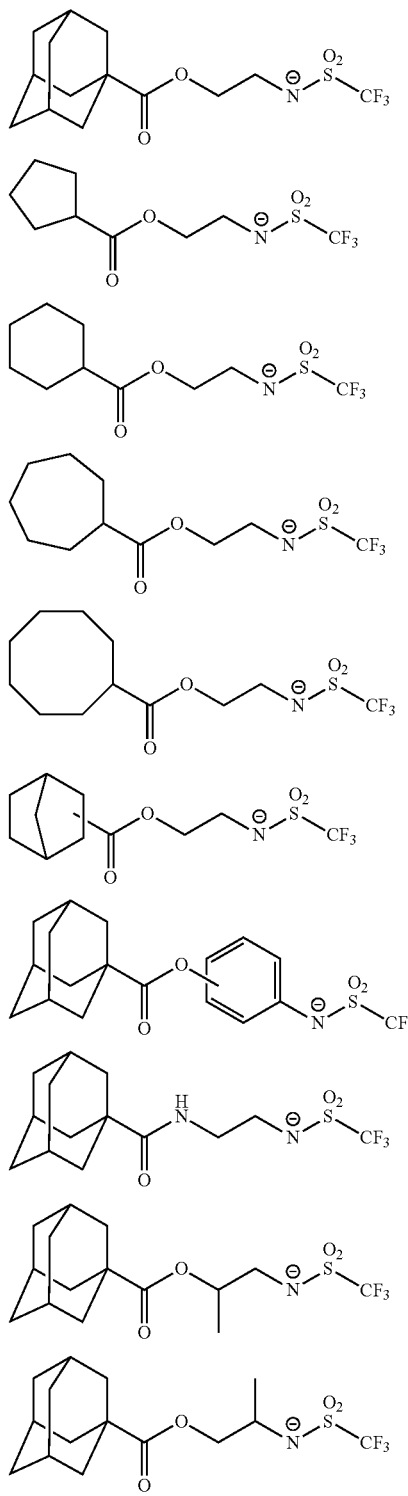

-continued

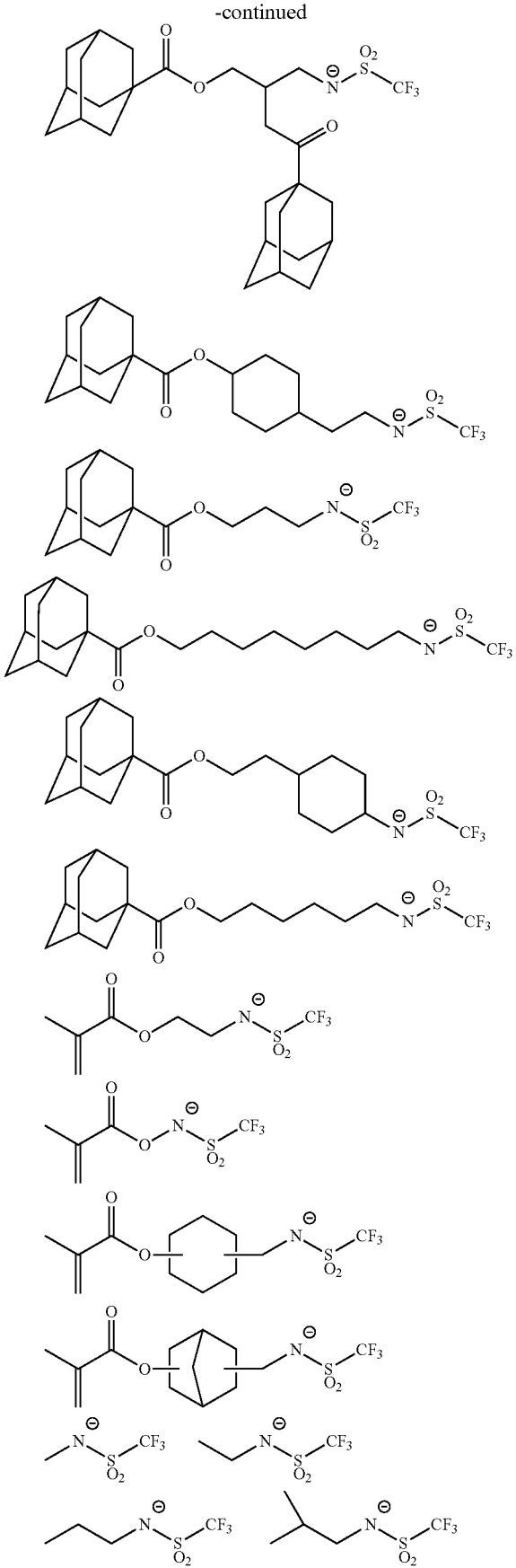

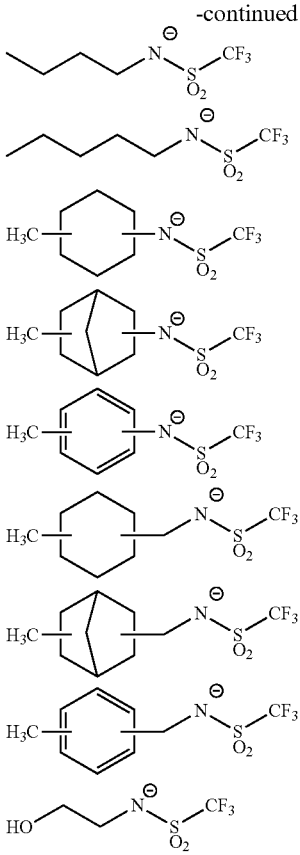

Cation Part

In general formula (d1-3), $M^{m+}$ is an m-valent organic cation, and is the same as $M^{m+}$ in general formula (d1-1).

The (d1-3) component may be used alone, or two or more kinds thereof may be used in combination.

The (D1) component may be obtained by using at least one of the (d1-1) to (d1-3) components, or using two or more kinds of components in combination.

The content of the (D1) component is preferably 0.5 to 10 parts by mass, is further preferably 0.5 to 8 parts by mass, and is still further preferably 1 to 8 parts by mass, with respect to 100 parts by mass of the (A) component.

When the content of the (D1) component is equal to or greater than the preferred lower limit value, it is possible to obtain particularly preferable lithography properties and resist pattern shape. On the other hand, when the (D1) component is equal to or lower than the upper limit value, it is possible to maintain the excellent sensitivity and to obtain excellent throughput.

The method of preparing the (d1-1) component and the (d1-2) component is not particularly limited, and they can be produced according to the conventional well-known methods.

The content of the (D1) component is preferably 0.5 to 10.0 parts by mass, is further preferably 0.5 to 8.0 parts by mass, and is still further preferably 1.0 to 8.0 parts by mass, with respect to 100 parts by mass of the (A) component. When the content of the (D1) component is equal to or greater than the preferred lower limit value, it is possible to obtain particularly preferable lithography properties and resist pattern shape. On the other hand, when the (D1) component is equal to or lower than the upper limit value of the above range, it is possible to maintain the excellent sensitivity and to obtain excellent throughput.

(D2) Component

The (D) component may contain a nitrogen-containing organic compound component (hereinafter, referred to as "(D2) component") which does not correspond to the (D1) component.

The (D2) component is not particularly limited as long as it acts as the acid diffusion control agent and does not correspond to the (D1) component, and may be arbitrarily used from the well-known components. Among them, aliphatic amine is preferable, and particularly, secondary aliphatic amine and tertiary aliphatic amine are further preferable.

The aliphatic amine is an amine having one or more aliphatic groups, and the number of carbon atoms of the aliphatic group is preferably 1 to 12.

Examples of the aliphatic amine include an amine (alkyl amine or alkyl alcohol amine) in which at least one hydrogen atom of ammonia $NH_3$ is substituted with an alkyl group having equal to or less than 12 carbon atoms, or a hydroxyalkyl group, or a cyclic amine.

Specific examples of the alkyl amine and the alkyl alcohol amine include monoalkyl amines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among them, a trialkylamine having 5 to 10 carbon atoms is further preferable, and tri-n-pentylamine or tri-n-octylamine is particularly preferable.

Examples of the cyclic amine include a heterocyclic compound containing a nitrogen atom as a heteroatom. The heterocyclic compound may be a monocyclic compound (aliphatic monocyclic amine) or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo [4.3.0]-5-nonene, 1,8-diazabicyclocyclo [5.4.0]-7-undecene, hexamethylenetetramine, and 1,4-diazabicyclo[2.2.2] octane.

Examples of other aliphatic amines include tris(2-methoxymethoxyethyl) amine, tris{2-(2-methoxyethoxy) ethyl} amine, tris{2-(2-methoxyethoxymethoxy) ethyl} amine, tris{2-(1-methoxyethoxy) ethyl} amine, tris{2-(1-ethoxyethoxy) ethyl} amine, tris{2-(1-ethoxypropoxy) ethyl} amine, tris[2-{2-(2-hydroxyethoxy) ethoxy} ethyl] amine, and triethanolamine triacetate. Among them, triethanolamine triacetate is preferable.

In addition, an aromatic amine may be used as the (D2) component.

Examples of the aromatic amine include aniline, pyridine, 4-dimethylaminopyridine, pyrrole, indole, pyrazole, imidazole, and derivatives thereof, diphenylamine, triphenylamine, tribenzylamine, 2,6-diisopropyl aniline, and N-tert-butoxycarbonyl pyrrolidine.

The (D2) component may be used alone, or two or more kinds thereof may be used in combination.

The content of the (D2) component is generally 0.01 to 5.0 parts by mass with respect to 100 parts by mass of the (A) component. When the content is within the above range, the resist pattern shape, the post exposure stability, and the like are improved.

The (D) component may be used alone or two or more kinds thereof may be used in combination.

In the case where the resist composition contains the (D) component in the present embodiment, the content of the (D) component is preferably 0.1 to 15 parts by mass, is further preferably 0.3 to 12 parts by mass, is still further preferably 0.5 to 12 parts by mass with respect to 100 parts by mass of the (A) component.

When the content of the (D) component is equal to or greater than the lower limit value of the above range, in the forming of the resist composition, the lithography properties such as LWR is further improved. In addition, it is possible to obtain a resist pattern having more excellent shape. When the content of the (D) component is equal to or lower than the upper limit value of the above range, it is possible to maintain the excellent sensitivity and to obtain excellent throughput.

(E) Component:

In the resist composition of the present embodiment, in order to prevent the sensitivity from being deteriorated and to improve the resist pattern shape and the post exposure stability, at least one compound (E) (hereinafter, referred to as "(E) component") selected from the group consisting of an organic carboxylic acid and an oxo acid of phosphorus, and derivatives thereof can be contained as an optional component.

As the organic carboxylic acid, for example, acetic acid, malonic acid, citric acid, malic acid, succinic acid, benzoic acid, and salicylic acid are preferable.

Examples of the oxo acid of phosphorus include phosphoric acid, phosphonic acid, and phosphinic acid, and among them, phosphonic acid is particularly preferable.

Examples of the derivative of the oxo acid of phosphorus include an ester obtained by substituting the hydrogen atom of the oxo acid with a hydrocarbon group, and examples of the hydrocarbon group include an alkyl group having 1 to 5 carbon atoms, and an aryl group having 6 to 15 carbon atoms.

Examples of the derivative of the phosphoric acid include a phosphate ester such as phosphoric acid di-n-butyl ester and phosphoric acid diphenyl ester.

Examples of the derivative of the phosphonic acid include a phosphonic acid ester such as phosphonic acid dimethyl ester, phosphonic acid-di-n-butyl ester, phenyl phosphonic acid, phosphonic acid diphenyl ester, and phosphonic acid dibenzyl ester.

Examples of the derivative of the phosphinic acid include phosphinic acid ester and a phenyl phosphinic acid.

The (E) component may be used alone, or two or more kinds thereof may be used in combination.

The content of the (E) component is generally 0.01 to 5.0 parts by mass with respect to 100 parts by mass of the (A) component.

(S) Component:

The resist composition of the present embodiment can be prepared by dissolving a resist material into an organic solvent component (hereinafter, referred to as "(S) component").

The (S) component may be a component which can form a homogeneous solution by dissolving the respective components to be used, and one or two or more kinds of well-known conventional solvents of the chemically amplified resist composition is properly selected so as to be used as the (S) component.

Examples of the (S) component include lactones such as γ-butyrolactone; ketones such as acetone, methyl ethyl ketone (MEK), cyclohexanone, methyl-n-pentyl ketone (2-heptanone), and methyl isopentyl ketone; polyhydric alcohols such as ethylene glycol, diethylene glycol, propylene glycol, and dipropylene glycol; derivatives of polyhydric alcohols such as a compound having an ester bond such as ethylene glycol monoacetate, diethylene glycol monoacetate, propylene glycol monoacetate, or dipropylene glycol monoacetate, and a compound having an etter bond such as monoalkyl ether or monophenyl ether such as monomethyl ether, monoethyl ether, monopropyl ether, and monobutyl ether of the compound having the polyhydric alcohol or the ester bond [among them, propylene glycol monomethyl ether acetate (PGMEA), and propylene glycol monomethyl ether (PGME), are preferable]; cyclic ethers such as dioxane, esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethyl benzyl ether, cresyl methyl ether, diphenyl ether, dibenzyl ether, phenetole, butyl phenyl ether, ethyl benzene, diethyl benzene, pentyl benzene, isopropyl benzene, toluene, xylene, cymene, and mesitylene; and dimethyl sulfoxide (DMSO).

The organic solvent may be used alone or may be used as a mixed solvent of two or more kinds thereof.

Among them, PGMEA, PGME, γ-butyrolactone, and EL are preferable.

In addition, a mixed solvent obtained by mixing PGMEA and a polar solvent is also preferable. The mixing ratio (mass ratio) may be properly determined in consideration of the compatibility of the PGMEA with the polar solvent, and the ratio is preferably 1:9 to 9:1, and is further preferably 2:8 to 8:2.

More specifically, in the case of mixing EL or cyclohexanone as the polar solvent, the mass ratio of PGMEA to EL or cyclohexanone is preferably 1:9 to 9:1, and is further preferably 2:8 to 8:2. In addition, in the case of mixing PGME as a polar solvent, the mass ratio of PGMEA to PGME is preferably 1:9 to 9:1, is further preferably 2:8 to 8:2, and still further preferably 3:7 to 7:3.

Further, as the (S) component, a mixed solvent obtained by mixing at least one selected from PGMEA and EL with 1-butyrolactone is also preferable. In this case, as the mixing ratio, the mass ratio of the former to the latter is preferably set to be 70:30 to 95:5.

The content of the (S) component used is not particularly limited, and is properly set in accordance with the coated film thickness at a concentration that can be applied to a substrate or the like. Generally, the (S) component is used such that the concentration of solid contents of the resist composition is 1 to 20% by mass, and is preferably 2 to 15% by mass.

It is possible to incorporate a miscible additive to the resist composition of the present invention as necessary, and for example, an additional resin for improving the performance of the resist film, a dissolution inhibitor, a plasticizer, a stabilizer, a colorant, a halation inhibitor, or a dye may be added.

Method for Forming Resist Pattern

A method for forming a resist pattern according to the present embodiment of the present invention includes a step of forming a resist film on a support by using the resist composition according to the present embodiment, a step of exposing the resist film, and a step of developing the exposed resist film to form a resist pattern.

The method for forming a resist pattern of the present embodiment can be performed in the following manner.

First, the support is coated with the resist composition according to the present embodiment with a spinner, and the coated film is subjected to a bake (Post Applied Bake (PAB)) treatment at a temperature of 80° C. to 150° C. for 40 to 120 seconds, preferably for 60 to 90 seconds, so as to form a resist film.

Then, the resist film is exposed via a mask (a mask pattern) on which a predetermined pattern is formed by using an exposure apparatus such as an electron beam lithography apparatus, and an EUV exposure apparatus, or is selectively exposed by lithography or the like due to direct irradiation of an electron beam without the mask pattern, and then is subjected to a bake (Post Exposure Bake (PEB)) treatment at a temperature of 80° C. to 150° C. for 40 to 120 seconds (preferably for 60 to 90 seconds).

Subsequently, the resist film is subjected to the developing treatment. In the developing treatment, an alkali developing solution is used in the case of the alkali developing process, and a developing solution (organic developing solution) containing an organic solvent is used in the case of the solvent developing process.

After the developing treatment, a rinse treatment is preferably performed. In the rinse treatment, water rinsing is preferably performed by using pure water in the case of the alkali developing process, and a rinsing liquid containing an organic solvent is preferably used in the case of the solvent developing process.

In the case of the solvent developing process, a treatment of removing the developing solution or the rinsing liquid which is attached on the pattern by a supercritical fluid may be performed after the developing treatment or the rinse treatment.

Drying is performed after the developing treatment or the rinse treatment. In addition, in some cases, a bake (post bake) treatment may be performed after the developing treatment.

In this way, it is possible to form a resist pattern.

The support is not particularly limited, and it is possible to use conventionally well-known supports. Examples thereof include a substrate for electronic parts and a substrate on which a prescribed wiring pattern is formed. More specifically, examples of the support include a metallic substrate such as a silicon wafer, copper, chromium, iron, and aluminum, and a glass substrate. As the wire pattern material, for example, it is possible to use copper, aluminum, nickel, and gold.

In addition, one obtained by providing an inorganic and/or organic film on the substrate may be used as the support. Examples of the inorganic film include an inorganic antireflection film (inorganic BARC). Examples of the organic film include an organic antireflection film (organic BARC) or a lower layer organic film obtained by using a multilayer resist method.

Here, the multilayer resist method is a method of providing at least a single layer of organic film (lower layer organic film) and at least single layer of resist film (upper layer resist film) on the substrate, and then performing the patterning of the lower layer organic film by setting the resist pattern formed on the upper layer resist film as a mask. With such a method, it is possible to form a pattern with a high aspect ratio. That is, according to the multilayer resist method, since the required thickness can be secured by the lower layer organic film, the resist film can be thinned and a fine pattern with the high aspect ratio can be formed.

The multilayer resist method basically includes a method (two-layer resist method) of setting a two-layer structure of an upper layer resist film and a lower layer organic film, and a method (three-layer resist method) of setting a multilayer (three or more layers) structure of providing one or more intermediate layers (thin metal film and the like) between the upper layer resist film and the lower layer organic film.

The wavelength used in the exposure is not particularly limited, and the exposure can be performed with radiations such as ArF excimer laser, KrF excimer laser, $F_2$ excimer laser, extreme ultraviolet rays (EUV), vacuum ultraviolet rays (VUV), electron beams (EB), X rays, and soft X rays. The resist composition is highly useful when being used for KrF excimer laser, ArF excimer laser, EB or EUV, is further useful when being used for ArF excimer laser, EB or EUV, and is particularly useful when being used for EB or EUV.

As a method for exposing a resist film, a typical exposure (dry exposure) performed in an inert gas such as air or nitrogen, or liquid immersion lithography may be employed.

The liquid immersion lithography is an exposing method performed in such a manner that a space between a resist film and a lens at the lowermost position of an exposure apparatus is filled in advance with a solvent (liquid immersion medium) having a refractive index larger than the refractive index of air, and exposure (immersion exposure) is performed in that state.

The liquid immersion medium is preferably a solvent having a refractive index which is larger than refractive index of air, and is smaller than the refractive index of the resist film to be exposed. The refractive index of the solvent is not particularly limited as long as it is within the range.

Examples of the solvent having a refractive index which is larger than refractive index of air, and is smaller than the refractive index of the resist film include water, a fluorinated inert liquid, a silicon solvent, and a hydrocarbon solvent.

Specific examples of the fluorinated inert liquid include a liquid having a fluorine compound as a main component, such as $C_3HCl_2F_5$, $C_4F_9OCH_3$, $C_4F_9OC_2H_5$, and $C_5H_3F_7$, and the boiling point thereof is preferably 70° C. to 180° C., and is further preferably 80° C. to 160° C. When the fluorinated inert liquid has the boiling point within the range, after completion of the exposure, the medium used for the liquid immersion can be removed by a simple method.

The fluorinated inert liquid is particularly preferably a perfluoroalkyl compound in which all hydrogen atoms of an alkyl group are substituted with a fluorine atom. Specific examples of the perfluoroalkyl compound include a perfluoroalkyl ether compound and a perfluoroalkylamine compound.

Further, specifically, examples of the perfluoroalkyl ether compound include perfluoro (2-butyl-tetrahydrofuran) (boiling point 102° C.), and examples of the perfluoroalkylamine compound include perfluorotributylamine (boiling point of 174° C.)

As the liquid immersion medium, water is preferably used in terms of cost, safety, environmental problems, and versatility.

Examples of an alkali developing solution used for the developing treatment in the alkali developing process include 0.1 to 10% by mass of tetramethyl ammonium hydroxide (TMAH) aqueous solution.

The organic solvent contained in an organic developing solution used for the developing treatment in the solvent developing process may be a solvent in which the (A) component ((A) component before exposure) can be dissolved, and can be appropriately selected from well-known organic solvents. Specific examples thereof include a polar solvent such as a ketone-based solvent, an ester-based solvent, an alcohol-based solvent, a nitrile-based solvent, an amide-based solvent, and an ether-based solvent, and a hydrocarbon solvent.

The ketone-based solvent is an organic solvent containing C—C(=O)—C in the structure. The ester-based solvent is an organic solvent containing C—C(=O)—O—C in the structure. The alcohol-based solvent is an organic solvent containing an alcoholic hydroxyl group in the structure. The "alcoholic hydroxyl group" means a hydroxyl group which is bonded to a carbon atom of an aliphatic hydrocarbon group. The nitrile-based solvent is an organic solvent containing a nitrile group in the structure. The amide-based solvent is an organic solvent containing an amide group in the structure. The ether-based solvent is an organic solvent containing C—O—C in the structure.

In the organic solvent, an organic solvent which contains various kinds of functional groups characterizing each solvent in the structure is also present. In this case, the organic solvent is regarded to correspond to all of the respective organic solvents which contain each of the functional groups that the organic solvent has. For example, diethylene glycol monomethyl ether corresponds to any one of the alcohol-based solvent and the ether-based solvent in the solvent kinds.

The hydrocarbon solvent composed of hydrocarbons which may be halogenated, and does not contain a substituent except for a halogen atom. Examples of the halogen atom include a fluorine atom, a chlorine atom, a bromine atom, and an iodine atom, and among them, the fluorine atom is preferable.

Among the above examples, the organic solvent which in an organic developing solution contains is preferably a polar solvent, and the ketone-based solvent, the ester-based solvent, and the nitrile-based solvent are preferable.

Examples of the ketone-based solvent include 1-octanone, 2-octanone, 1-nonanone, 2-nonanone, acetone, 4-heptanone, 1-hexanone, 2-hexanone, diisobutyl ketone, cyclohexanone, methyl cyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, propylene carbonate, γ-butyrolactone, and methyl amyl ketone (2-heptanone). Among them, the ketone-based solvent is preferably methyl amyl ketone (2-heptanone).

Examples of the ester-based solvent include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate, and propyl-3-methoxypropionate. Among them, the ester-based solvent is preferably butyl acetate.

Examples of the nitrile-based solvent include acetonitrile, propionitrile, valeronitrile, and butyronitrile.

In the organic developing solution, well-known additives can be mixed as necessary. Examples of the additives include a surfactant. The surfactant is not particularly limited, and examples thereof include an ionic or nonionic fluorine-based and/or silicon-based surfactant.

The surfactant is preferably a nonionic surfactant, and is further preferably a nonionic fluorine-based surfactant or a nonionic silicon-based surfactant.

In the case of mixing the surfactant, the mixing content is generally 0.001 to 5% by mass, is preferably 0.005 to 2% by mass, and is further preferably 0.01 to 0.5% by mass, with respect to the entire content of the organic developing solution.

The developing treatment can be performed according to a well-known developing method, and examples thereof include a method of dipping the support into the developing solution for a certain period of time (a dipping method), a method of placing a puddle of the developing solution on the surface of the support by surface tension and standing as it is for a certain period of time (a puddle method), a method of spraying the developing solution on the surface of the support (a spray method), and a method of continuously coating a support which rotates at a constant speed with the developing solution while scanning a coating nozzle (a dynamic dispense method).

As the organic solvent contained in a rinsing liquid used in the rinse treatment after the developing treatment in the solvent developing process, an organic solvent in which a resist pattern is not easily dissolved can be appropriately selected from the organic solvents exemplified as the organic solvent used in the organic developing solution. Typically, at least one solvent selected from a hydrocarbon solvent, a ketone-based solvent, an ester-based solvent, an alcohol-based solvent, an amide-based solvent, and an ether-based solvent is used. Among them, at least one selected from the hydrocarbon solvent, the ketone-based solvent, the ester-based solvent, the alcohol-based solvent, and the amide-based solvent is preferably used, at least one selected from the alcohol-based solvent and the ester-based solvent is further preferably used, and the alcohol-based solvent is particularly preferable.

The alcohol-based solvent used in the rinsing liquid is preferably monohydric alcohol having 6 to 8 carbon atoms, or the monohydric alcohol may be linear, branched, or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol, and benzyl alcohol.

Among them, 1-hexanol, 2-heptanol, and 2-hexanol are preferable, and 1-hexanol and 2-hexanol are further preferable.

These organic solvents may be used alone, or two or more kinds thereof may be used in combination. In addition, an organic solvent other than the organic solvents or water may be mixed and used. Here, when considering the developing property, the mixing content of water in the rinsing liquid is preferably 30% by mass or less, is further preferably 10% by mass or less, is still further preferably 5% by mass or less, and is particularly preferably equal to or less than 3% by mass with respect to the total content of the rinsing liquid.

In the rinsing liquid, well-known additives can be mixed as necessary. Examples of the additives include a surfactant. Examples of the surfactant include the same surfactant as described above, and a nonionic surfactant is preferable, a nonionic fluorine-based surfactant or a nonionic silicon-based surfactant is further preferable.

In the case of mixing the surfactant, the mixing content is generally 0.001 to 5% by mass, is preferably 0.005 to 2% by mass, and is further preferably 0.01 to 0.5% by mass, with respect to the entire content of the rinsing liquid.

The rinse treatment (washing treatment) using a rinsing liquid can be performed according to a well-known rinsing method. Examples of a method of the rinse treatment include a method of continuously coating a support which rotates at a constant speed with the rinsing liquid (a rotary coating method), a method of dipping the support into the rinsing liquid (a dip method) for a certain period of time, and a method of spraying the rinsing liquid to the surface of the support (a spray method).

The resist composition of the present embodiment contains a base material component (A) and a fluorine additive component (F).

The (A) component contains a resin component (A1) having a structural unit (a10) of equal to or greater than 10 mol %, and a structural unit (a1) of equal to or greater than 30 mol %. For this reason, the resist composition of the present embodiment is particularly suitable for extreme ultraviolet rays (EUV) lithography or electron beam (EB) lithography.

In addition, the (F) component contains a fluororesin component (F1) having a structural unit (f1). In the EUV lithography or the EB lithography, it is required to improve various lithography properties, and to suppress the generation of defects. One of the cause of the generation of defects is considered to be that precipitates (for example, hardly soluble substances with respect to an alkali developing solution) adhere to the surface of the resist pattern in the developing process. Since the (F1) component contains a fluorine atom, it is presumed that the (F1) component segregates on the resist pattern surface. The (F1) component which segregates on the resist pattern surface is decomposed under the action of a base (for example, an alkali developing solution), thereby generating a hydrophilic group. For this reason, with the (F1) component the surface of the resist pattern can be rendered hydrophilic at the time of development, and thus adhesion of precipitates and the like can be suppressed, and generation of defects can be reduced.

EXAMPLES

Hereinafter, the present invention will be more specifically described with reference to examples; however, the invention is not limited thereto.

Polymer Synthesis Example

Polymers (A)-1 to (A)-18 were obtained by performing the radical polymerization of the following monomers (02), (10), (01), and (03).

Regarding the polymers (A)-1 to (A)-18, a copolymer composition ratio (the ratio (molar ratio) of each structural unit in the polymer compound) of the polymer compound obtained by using $^{13}$C-NMR, a mass average molecular weight (Mw), and a molecular weight dispersivity (Mw/Mn), which are obtained by GPC measurement in terms of standard polystyrene, were indicated in Table 1.

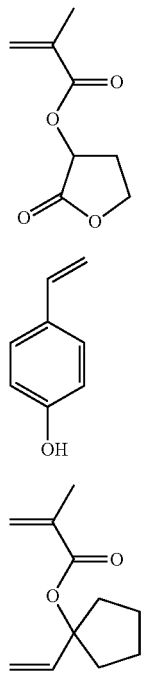

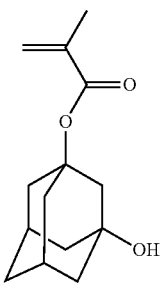

TABLE 1

| Polymer | Monomer (02) | Monomer (10) | Monomer (01) | Monomer (03) | Mw | Mw/Mn |
|---|---|---|---|---|---|---|
| (A)-1 | 20 | 20 | 50 | 10 | 7000 | 1.6 |
| (A)-2 | 30 | 20 | 40 | 10 | 7000 | 1.6 |
| (A)-3 | 40 | 20 | 30 | 10 | 7000 | 1.6 |
| (A)-4 | 40 | 10 | 40 | 10 | 7000 | 1.6 |
| (A)-5 | 30 | 20 | 40 | 10 | 7000 | 1.6 |
| (A)-6 | 30 | 20 | 40 | 10 | 7000 | 1.6 |
| (A)-7 | 30 | 20 | 40 | 10 | 7000 | 1.6 |
| (A)-8 | 30 | 20 | 40 | 10 | 7000 | 1.6 |
| (A)-9 | 30 | 20 | 40 | 10 | 7000 | 1.6 |
| (A)-10 | 30 | 20 | 40 | 10 | 7000 | 1.6 |
| (A)-11 | 30 | 20 | 40 | 10 | 7000 | 1.6 |
| (A)-12 | 30 | 20 | 40 | 10 | 7000 | 1.6 |
| (A)-13 | 20 | 20 | 50 | 10 | 7000 | 1.6 |
| (A)-14 | 30 | 20 | 40 | 10 | 7000 | 1.6 |
| (A)-15 | 40 | 20 | 30 | 10 | 7000 | 1.6 |
| (A)-16 | 40 | 10 | 40 | 10 | 7000 | 1.6 |
| (A)-17 | 50 | 0 | 40 | 10 | 7000 | 1.6 |
| (A)-18 | 30 | 20 | 40 | 10 | 7000 | 1.6 |

Preparation of Resist Composition

The components indicated in Table 2 were mixed and dissolved to prepare resist compositions of the respective examples.

TABLE 2

| | (A) component | (B) component | (D) component | (E) component | (F) component | (S) component |
|---|---|---|---|---|---|---|
| Example 1 | (A)-1 [100] | (B)-1 [14] | (D)-1 [3.0] | — | (F)-1 [3] | (S)-1 [70] |
| Example 2 | (A)-2 [100] | (B)-1 [14] | (D)-1 [3.0] | — | (F)-1 [3] | (S)-1 [70] |
| Example 3 | (A)-3 [100] | (B)-1 [14] | (D)-1 [3.0] | — | (F)-1 [3] | (S)-1 [70] |
| Example 4 | (A)-4 [100] | (B)-1 [14] | (D)-1 [3.0] | — | (F)-1 [3] | (S)-1 [70] |
| Example 5 | (A)-5 [100] | (B)-1 [14] | (D)-2 [1.5] | (E)-1 [0.64] | (F)-1 [3] | (S)-1 [70] |
| Example 6 | (A)-6 [100] | (B)-1 [14] | (D)-1 [3.0] | — | (F)-2 [3] | (S)-1 [70] |
| Example 7 | (A)-7 [100] | (B)-1 [14] | (D)-1 [3.0] | — | (F)-3 [3] | (S)-1 [70] |
| Example 8 | (A)-8 [100] | (B)-1 [14] | (D)-1 [3.0] | — | (F)-4 [3] | (S)-1 [70] |
| Example 9 | (A)-9 [100] | (B)-1 [14] | (D)-1 [3.0] | — | (F)-5 [3] | (S)-1 [70] |

TABLE 2-continued

|  | (A) component | (B) component | (D) component | (E) component | (F) component | (S) component |
|---|---|---|---|---|---|---|
| Example 10 | (A)-10 [100] | (B)-1 [14] | (D)-1 [3.0] | — | (F)-6 [3] | (S)-1 [70] |
| Example 11 | (A)-11 [100] | (B)-1 [14] | (D)-1 [3.0] | — | (F)-7 [3] | (S)-1 [70] |
| Example 12 | (A)-12 [100] | (B)-1 [14] | (D)-1 [3.0] | — | (F)-8 [3] | (S)-1 [70] |
| Comparative Example 1 | (A)-13 [100] | (B)-1 [14] | (D)-1 [3.0] | — | — | (S)-1 [70] |
| Comparative Example 2 | (A)-14 [100] | (B)-1 [14] | (D)-1 [3.0] | — | — | (S)-1 [70] |
| Comparative Example 3 | (A)-15 [100] | (B)-1 [14] | (D)-1 [3.0] | — | — | (S)-1 [70] |
| Comparative Example 4 | (A)-16 [100] | (B)-1 [14] | (D)-1 [3.0] | — | — | (S)-1 [70] |
| Comparative Example 5 | (A)-17 [100] | (B)-1 [14] | (D)-1 [3.0] | — | — | (S)-1 [70] |
| Comparative Example 6 | (A)-18 [100] | (B)-1 [14] | (D)-2 [1.5] | (E)-1 [0.64] | — | (S)-1 [70] |

In Table 2, each abbreviation has the following meaning. Each numerical value in the brackets is the compounding amount (parts by mass).

(A)-1 to (A)-18: polymers (A)-1 to (A)-18

(B)-1: acid generator represented by general formula (B)-1

(D)-1: acid diffusion controlling agent represented by general formula (D)-1

(D)-2: tri-n-octylamine (E)-1: salicylic acid (F)-1: fluorine-containing polymer compound represented by general formula (F)-1; the mass average molecular weight (Mw), which is obtained by GPC measurement in terms of standard polystyrene, is 20,000, the molecular weight dispersivity (Mw/Mn) is 1.6; and the copolymer composition ratio (the ratio (molar ratio) of each structural unit in the structural formula) obtained by using $^{13}$C-NMR is l/m=80/20.

(F)-2: fluorine-containing polymer compound represented by general formula (F)-2; the mass average molecular weight (Mw), which is obtained by GPC measurement in terms of standard polystyrene, is 20,000, the molecular weight dispersivity (Mw/Mn) is 1.6; and the copolymer composition ratio (the ratio (molar ratio) of each structural unit in the structural formula) obtained by using $^{13}$C-NMR is l/m=80/20.

(F)-3: fluorine-containing polymer compound represented by general formula (F)-3; the mass average molecular weight (Mw), which is obtained by GPC measurement in terms of standard polystyrene, is 20,000, the molecular weight dispersivity (Mw/Mn) is 1.6; and the copolymer composition ratio (the ratio (molar ratio) of each structural unit in the structural formula) obtained by using $^{13}$C-NMR is l/m=60/40.

(F)-4: fluorine-containing polymer compound (homopolymer) represented by general formula (F)-4; the mass average molecular weight (Mw), which is obtained by GPC measurement in terms of standard polystyrene, is 20,000, the molecular weight dispersivity (Mw/Mn) is 1.6.

(F)-5: fluorine-containing polymer compound represented by general formula (F)-5; the mass average molecular weight (Mw), which is obtained by GPC measurement in terms of standard polystyrene, is 20,000, the molecular weight dispersivity (Mw/Mn) is 1.6; and the copolymer composition ratio (the ratio (molar ratio) of each structural unit in the structural formula) obtained by using $^{13}$C-NMR is l/m/n=70/20/10.

(F)-6: fluorine-containing polymer compound represented by general formula (F)-6; the mass average molecular weight (Mw), which is obtained by GPC measurement in terms of standard polystyrene, is 20,000, the molecular weight dispersivity (Mw/Mn) is 1.6; and the copolymer composition ratio (the ratio (molar ratio) of each structural unit in the structural formula) obtained by using $^{13}$C-NMR is l/m=70/30.

(F)-7: fluorine-containing polymer compound represented by general formula (F)-7; the mass average molecular weight (Mw), which is obtained by GPC measurement in terms of standard polystyrene, is 20,000, the molecular weight dispersivity (Mw/Mn) is 1.6; and the copolymer composition ratio (the ratio (molar ratio) of each structural unit in the structural formula) obtained by using $^{13}$C-NMR is l/m=80/20.

(F)-8: fluorine-containing polymer compound represented by general formula (F)-8; the mass average molecular weight (Mw), which is obtained by GPC measurement in terms of standard polystyrene, is 20,000, the molecular weight dispersivity (Mw/Mn) is 1.6; and the copolymer composition ratio (the ratio (molar ratio) of each structural unit in the structural formula) obtained by using $^{13}$C-NMR is l/m=80/20.

(S)-1: mixed solvent of propylene glycol monomethyl ether acetate/propylene glycol monomethyl ether=60/40 (mass ratio)

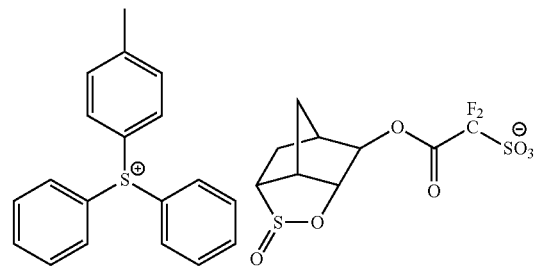

(B)-1

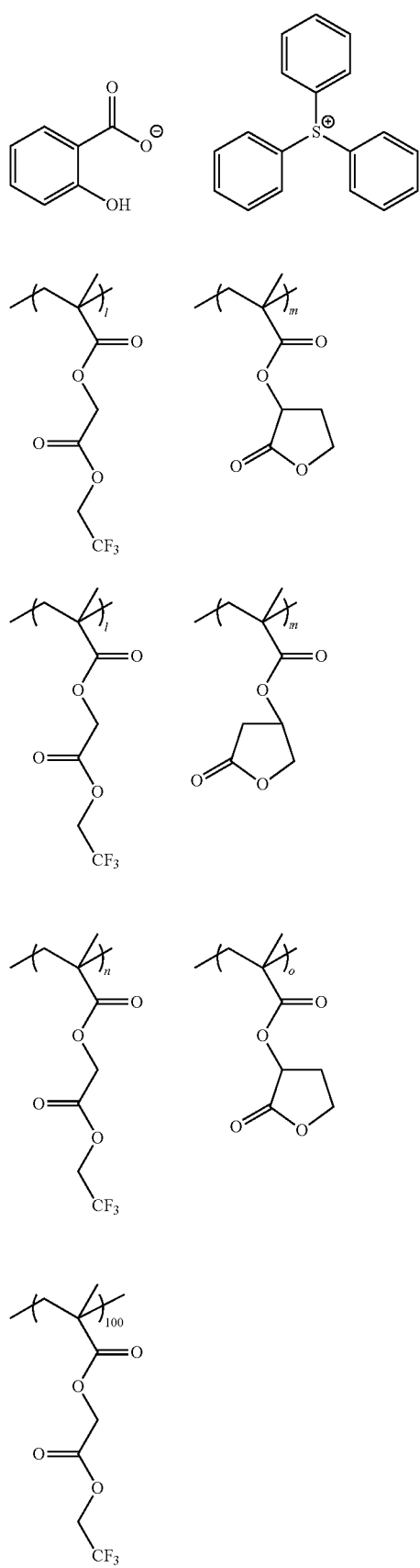
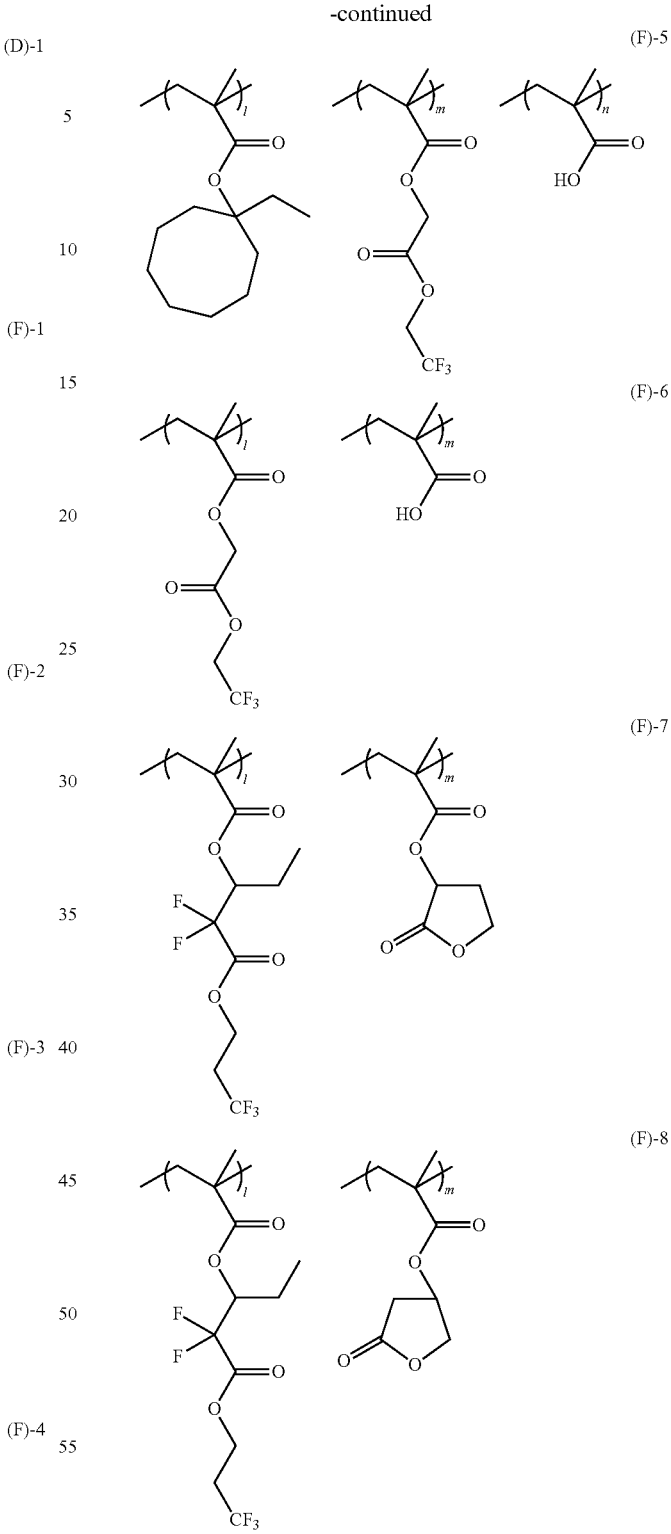
Formation of Resist Pattern (1)
A 12-inch silicon substrate treated with hexamethyldisilazane (HMDS) was coated with the resist composition of each example with a spinner, was subjected to a pre-baking (PAB) treatment at 130° C. for 60 seconds on a hot plate, and was dried to thereby form a resist film having a film thickness of 50 nm.

Next, on the resist film, the resist film was selectively irradiated with ArF excimer laser (193 nm) via a mask using an ArF exposure apparatus, NSR-S308F (manufactured by Nikon Corporation; NA (number of opening)=0.92). Thereafter, a post exposure bake (PEB) treatment was performed at 130° C. for 60 seconds Then, the resist film was subjected to an alkali developing at 23° C. for 10 seconds with an aqueous solution containing 2.38% by mass of tetramethyl ammoniumhydroxide (TMAH) "NMD-3" (product name, prepared by Tokyo Ohka Kogyo Co., Ltd).

Thereafter, water rinsing was performed for 15 seconds with pure water.

As a result, a 1:1 LS pattern having a line width of 65 nm was formed. This is performed in order to pseudo-form an exposed portion by EB or EUV exposure.

Evaluation of Defects

Regarding the large-area unexposed area located next to the pattern area obtained in Formation of resist pattern (1), the total number of defects (total number of defects/number) in the wafer was measured by using a surface defect observing apparatus (product name: KLA2371, manufactured by KLA-Tencor Corporation). This result is indicated in Table 3.

Formation of Resist Pattern (2)

A 12-inch silicon substrate treated with hexamethyldisilazane (HMDS) was coated with the resist composition of each example with a spinner, was subjected to a pre-baking (PAB) treatment at 110° C. for 60 seconds on a hot plate, and was dried to thereby form a resist film having a film thickness of 30 nm.

Next, on the resist film, lithography (exposure) was performed using an electron beam drawing apparatus JEOL-JBX-9300FS (manufactured by JEOL Ltd.) at an acceleration voltage of 100 kV setting a 1:1 line and space pattern (hereinafter, referred to as an "LS pattern") having a line width of 50 to 26 nm as a target size. Thereafter, a post exposure bake (PEB) treatment was performed at 110° C. for 60 seconds.

Then, the resist film was subjected to an alkali developing at 23° C. for 60 seconds with an aqueous solution containing 2.38% by mass of tetramethyl ammonium hydroxide (TMAH) "NMD-3" (product name, prepared by Tokyo Ohka Kogyo Co., Ltd).

Thereafter, water rinsing was performed for 15 seconds with pure water.

As a result, a 1:1 LS pattern having a line width of 50 to 26 nm was formed.

Evaluation of Resolution

The limit resolution at the Eop, specifically, when the LS pattern is formed by gradually increasing the exposure amount from the optimum exposure amount Eop, the minimum dimension of the pattern resolved without collapse was measured by a scanning electron microscope S-9380 (manufactured by Hitachi High-Technologies Corporation), and was shown as "resolution performance (nm)" in Table 3.

Evaluation of Line-Width Roughness (LWR)

Regarding the LS pattern formed by the above "Forming of resist pattern (2)", 3σ which is a scale indicating LWR was obtained, and was shown as "LWR (nm)" in Table 3.

"3σ" (unit: nm) indicates three times the value of the standard deviation (σ) obtained from the result of the measurement performed by measuring a line width at each of 400 positions in the longitudinal direction of the line with a scanning electron microscope (acceleration voltage of 800V, product name: S-9380, manufactured by Hitachi High-Technologies Corporation).

It means that as the value of 3σ is small, the roughness of the line side wall is small, thereby obtaining the LS pattern having more uniform width.

TABLE 3

|  | Defect | Resolution performance (nm) | LWR (nm) |
| --- | --- | --- | --- |
| Example 1 | 1300 | 32 | 7.2 |
| Example 2 | 1000 | 35 | 7.4 |
| Example 3 | 800 | 35 | 8.2 |
| Example 4 | 900 | 35 | 7.8 |
| Example 5 | 1000 | 40 | 10.0 |
| Example 6 | 300 | 32 | 6.9 |
| Example 7 | 900 | 35 | 7.4 |
| Example 8 | 2100 | 35 | 7.5 |
| Example 9 | 1500 | 35 | 7.6 |
| Example 10 | 100 | 35 | 7.6 |
| Example 11 | 1200 | 35 | 7.4 |
| Example 12 | 800 | 32 | 7.1 |
| Comparative Example 1 | 9500 | 32 | 7.1 |
| Comparative Example 2 | 7700 | 35 | 7.5 |
| Comparative Example 3 | 7000 | 35 | 8.2 |
| Comparative Example 4 | 7100 | 35 | 7.7 |
| Comparative Example 5 | 6300 | 40 | 9.5 |
| Comparative Example 6 | 7600 | 40 | 10.1 |

From the results shown in Table 3, according to the resist compositions of Examples 1 to 12 to which the present invention is applied, it was confirmed that defects are reduced, and the lithography properties are excellent.

What is claimed is:

1. A resist composition which generates an acid upon exposure and whose solubility in a developing solution changes under the action of the acid, the resist composition comprising:

a base material component (A) whose solubility in the developing solution changes under the action of an acid, and which comprises a resin component (A1) having a structural unit (a10) represented by general formula (a10-1) in an amount of 10 mol % or more and a structural unit (a1) represented by general formula (a1-1-1) in an amount of 30 mol % or more;

an acid generator component (B) which generates an acid upon exposure; and a fluorine additive component (F) which exhibits the decomposability with respect to an alkali developing solution and comprises a fluororesin component (F1) having a structural unit (f1) containing a base dissociable group:

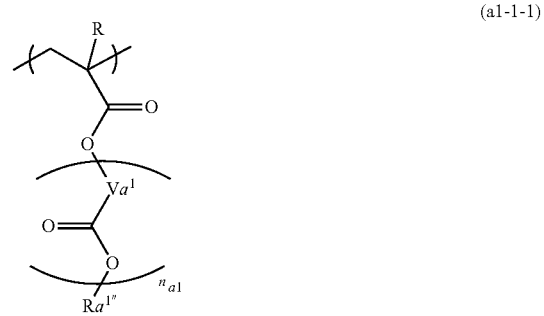

(a1-1-1)

-continued (a1-r2-2)

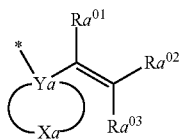

wherein R is a hydrogen atom, an alkyl group having 1 to 5 carbon atoms, or a halogenated alkyl group having 1 to 5 carbon atoms; $Va^1$ is a divalent hydrocarbon group which may have an ether bond; $n_{a1}$ is an integer of 0 to 2; $Ra^{1'''}$ is an acid dissociable group represented by general formula (a1-r2-2); Ya is a carbon atom; Xa is a group forming a cyclic hydrocarbon group together with Ya, provided that at least one hydrogen atom contained in the cyclic hydrocarbon group may be substituted; $Ra^{01}$ to $Ra^{03}$ each independently represent, a hydrogen atom, a monovalent chain saturated hydrocarbon group having 1 to 10 carbon atoms, or a monovalent aliphatic cyclic saturated hydrocarbon group having 3 to 20 carbon atoms, provided that at least one hydrogen atom contained in the chain saturated hydrocarbon group and the aliphatic cyclic saturated hydrocarbon group may be substituted; two or more of $Ra^{01}$ to $Ra^{03}$ may be bonded to each other to form a cyclic structure; * represents a bond;

(a10-1)

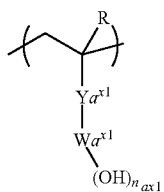

wherein R is a hydrogen atom, an alkyl group having 1 to 5 carbon atoms, or a halogenated alkyl group having 1 to 5 carbon atoms, $Ya^{x1}$ is a single bond, $Wa^{x1}$ is a group obtained by removing $(n_{ax1}+1)$ hydrogen atoms from benzene, naphthalene, anthracene, phenanthrene, pyridine or thiophene, and $na_{x1}$ is an integer of 1 to 3.

2. The resist composition according to claim 1, wherein the fluororesin component (F1) comprises a structural unit represented by general formula (f1-1) or a structural unit represented by general formula (f1-2):

(f1-1)

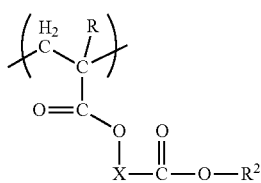

(f1-2)

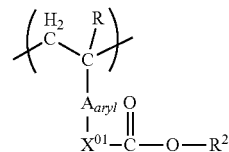

wherein R each independently is a hydrogen atom, an alkyl group having 1 to 5 carbon atoms, or a halogenated alkyl group having 1 to 5 carbon atoms, X is a divalent linking group having no acid dissociable moiety, $A_{aryl}$ is a divalent aromatic cyclic group which may have a substituent, $X_{01}$ is a single bond or a divalent linking group, and $R^2$'s are each independently an organic group having a fluorine atom.

3. The resist composition according to claim 1, wherein the fluororesin component (F1) further comprises a structural unit (f2) containing a lactone-containing cyclic group.

4. The resist composition according to claim 1, wherein the fluororesin component (F1) further comprises a structural unit (f3) represented by general formula (f3-1):

(f3-1)

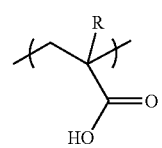

wherein R is a hydrogen atom, an alkyl group having 1 to 5 carbon atoms, or a halogenated alkyl group having 1 to 5 carbon atoms.

5. A method for forming a resist pattern, comprising:

forming a resist film on a support by using the resist composition according to claim 1;

exposing the resist film; and developing the exposed resist film to form a resist pattern.

6. The method for forming a resist pattern according to claim 5, wherein the resist film is exposed to extreme ultraviolet ray (EUV) or an electron beam (EB).

* * * * *